(12) United States Patent
Jung et al.

(10) Patent No.: US 11,706,970 B2
(45) Date of Patent: Jul. 18, 2023

(54) POLYMER, COATING COMPOSITION COMPRISING SAME, AND ORGANIC LIGHT EMITTING DEVICE USING SAME

(71) Applicant: LG Chem, Ltd., Seoul (KR)

(72) Inventors: Min Suk Jung, Daejeon (KR); Esder Kang, Daejeon (KR); Beomgoo Kang, Daejeon (KR); Jaesoon Bae, Daejeon (KR); Jaechol Lee, Daejeon (KR); Jiyeon Shin, Daejeon (KR); Seog Jae Seo, Daejeon (KR); Hyungil Park, Daejeon (KR); Byeong Yun Lim, Daejeon (KR); Dowon Lim, Daejeon (KR)

(73) Assignee: LG Chem, Ltd.

( * ) Notice: Subject to any disclaimer, the term of this patent is extended or adjusted under 35 U.S.C. 154(b) by 416 days.

(21) Appl. No.: 17/047,261

(22) PCT Filed: Aug. 16, 2019

(86) PCT No.: PCT/KR2019/010424
§ 371 (c)(1),
(2) Date: Oct. 13, 2020

(87) PCT Pub. No.: WO2020/036459
PCT Pub. Date: Feb. 20, 2020

(65) Prior Publication Data
US 2021/0175427 A1    Jun. 10, 2021

(30) Foreign Application Priority Data
Aug. 17, 2018    (KR) .................. 10-2018-0095968

(51) Int. Cl.
  *H01L 51/00*    (2006.01)
  *C07C 211/61*    (2006.01)
  (Continued)

(52) U.S. Cl.
  CPC .......... *H10K 85/115* (2023.02); *C07C 211/54* (2013.01); *C07C 211/61* (2013.01);
  (Continued)

(58) Field of Classification Search
  CPC .... C07C 211/54; C07C 211/61; H10K 85/115
  See application file for complete search history.

(56) References Cited

U.S. PATENT DOCUMENTS

2004/0067387 A1    4/2004    Kim et al.
2006/0234059 A1    10/2006    Celia et al.
(Continued)

FOREIGN PATENT DOCUMENTS

CN    102449799 A    5/2012
CN    104144909 A    11/2014
(Continued)

OTHER PUBLICATIONS

Nara Cho et al., "Novel organic sensitizers containing a bulky spirobifluorene unit for solar cell", Tetrahedron, available online May 2009, pp. 6236-6243, vol. 65, No. 31, Elsevier, Amsterdam.
(Continued)

*Primary Examiner* — Vu A Nguyen
(74) *Attorney, Agent, or Firm* — Lerner David LLP

(57) ABSTRACT

The present specification relates to a polymer including a unit represented by Chemical Formula 1, a coating compo-
(Continued)

sition including the same, and an organic light emitting device formed using the same:

[Chemical Formula 1]

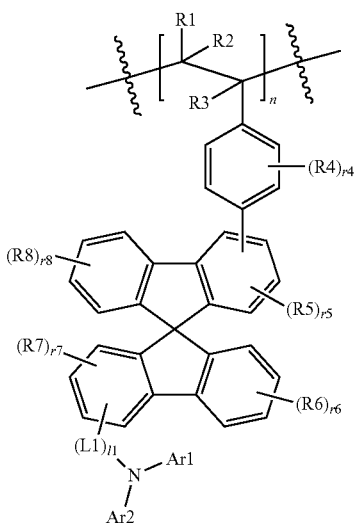

wherein all the variables are described herein.

19 Claims, 3 Drawing Sheets

(51) Int. Cl.

| | | |
|---|---|---|
| C07C 211/54 | (2006.01) |
| C09D 125/18 | (2006.01) |
| C08F 12/28 | (2006.01) |
| C08F 12/32 | (2006.01) |
| C07D 209/86 | (2006.01) |
| C07D 209/88 | (2006.01) |
| H10K 85/10 | (2023.01) |
| C07D 307/91 | (2006.01) |
| H10K 50/15 | (2023.01) |
| H10K 50/17 | (2023.01) |
| H10K 71/12 | (2023.01) |

(52) U.S. Cl.
CPC ......... *C07D 209/86* (2013.01); *C07D 209/88* (2013.01); *C07D 307/91* (2013.01); *C08F 12/28* (2013.01); *C08F 12/32* (2013.01); *C09D 125/18* (2013.01); *C07C 2603/18* (2017.05); *C07C 2603/97* (2017.05); *H10K 50/15* (2023.02); *H10K 50/17* (2023.02); *H10K 71/12* (2023.02)

(56) References Cited

U.S. PATENT DOCUMENTS

| | | |
|---|---|---|
| 2015/0094437 A1 | 4/2015 | Caille et al. |
| 2015/0263288 A1 | 9/2015 | Funyuu et al. |
| 2016/0181535 A1 | 6/2016 | Tsuji et al. |
| 2016/0225998 A1 | 8/2016 | Kato et al. |
| 2017/0125677 A1 | 5/2017 | Kim et al. |
| 2017/0358751 A1 | 12/2017 | Pan et al. |
| 2018/0182967 A1 | 6/2018 | Ito et al. |
| 2019/0040034 A1 | 2/2019 | Voges et al. |

FOREIGN PATENT DOCUMENTS

| | | | |
|---|---|---|---|
| JP | H11273863 A | | 10/1999 |
| JP | 2004303490 A | * | 10/2004 |
| JP | 2004303490 A | | 10/2004 |
| KR | 20040028954 A | | 4/2004 |
| KR | 20080005366 A | | 1/2008 |
| KR | 20160074382 A | | 6/2016 |
| KR | 20160093531 A | | 8/2016 |
| KR | 20170015847 A | | 2/2017 |
| KR | 20180076294 A | | 7/2018 |
| WO | 2017107117 A1 | | 6/2017 |
| WO | 2017133829 A1 | | 8/2017 |
| WO | 2018005318 A1 | | 1/2018 |
| WO | WO-2018005318 A1 | * | 1/2018 ......... H01L 51/0039 |

OTHER PUBLICATIONS

Supplemental European Search Report for Application No. 19850418.5 dated Apr. 29, 2021, 2 pages.
Search Report dated Sep. 16, 2022 from the Office Action for Chinese Application No. 201980023257.X dated Sep. 27, 2022, 2 pages.
International Search Report for Application No. PCT/KR2019/010424 dated Nov. 19, 2019, 2 pages.
Janietz, et al., "Concepts for the material development of phosphorescent organic materials processable from solution and their application in OLEDs," Proc. of SPIE, Oct. 8, 2014, pp. 918303-1-918303-08, vol. 9183.

* cited by examiner

[FIG. 1]
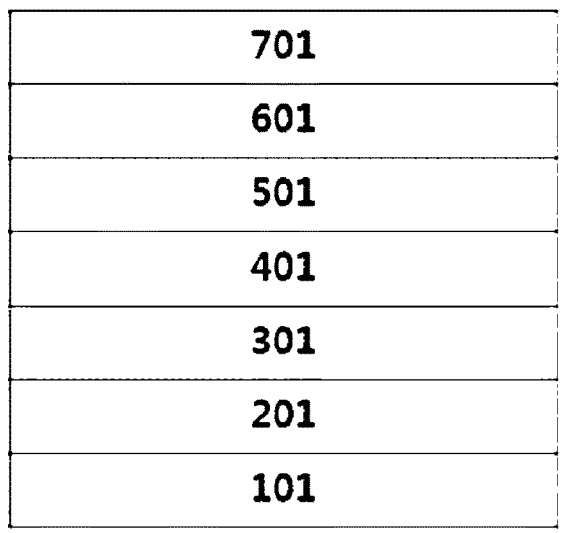
[FIG. 2]
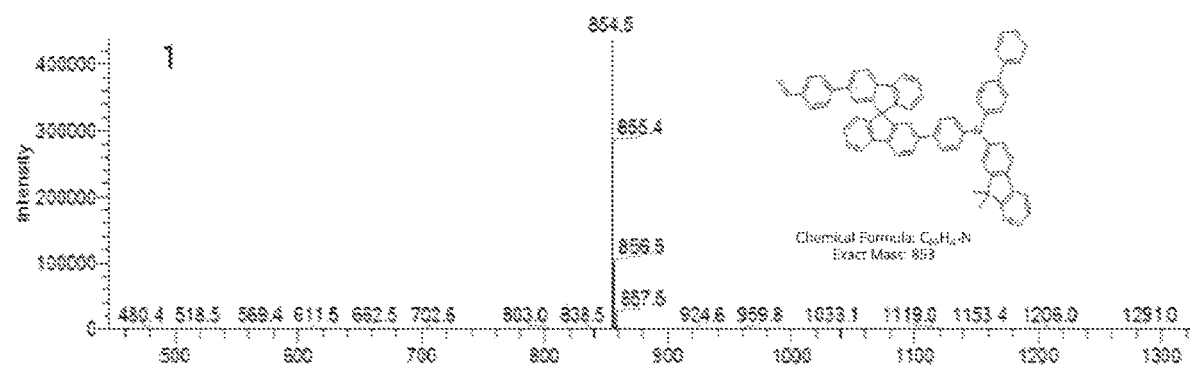

[FIG. 3]
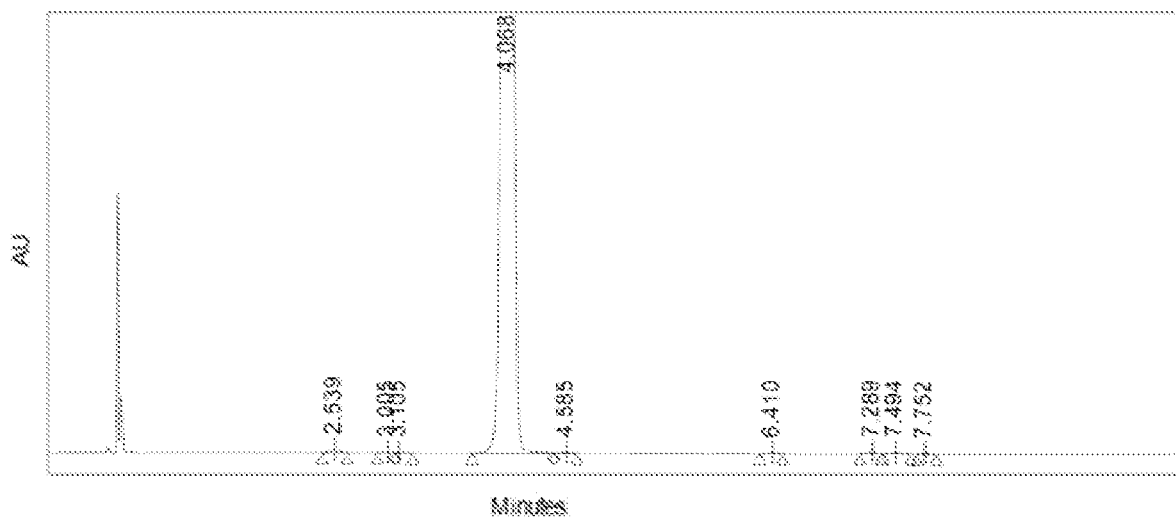
[FIG. 4]
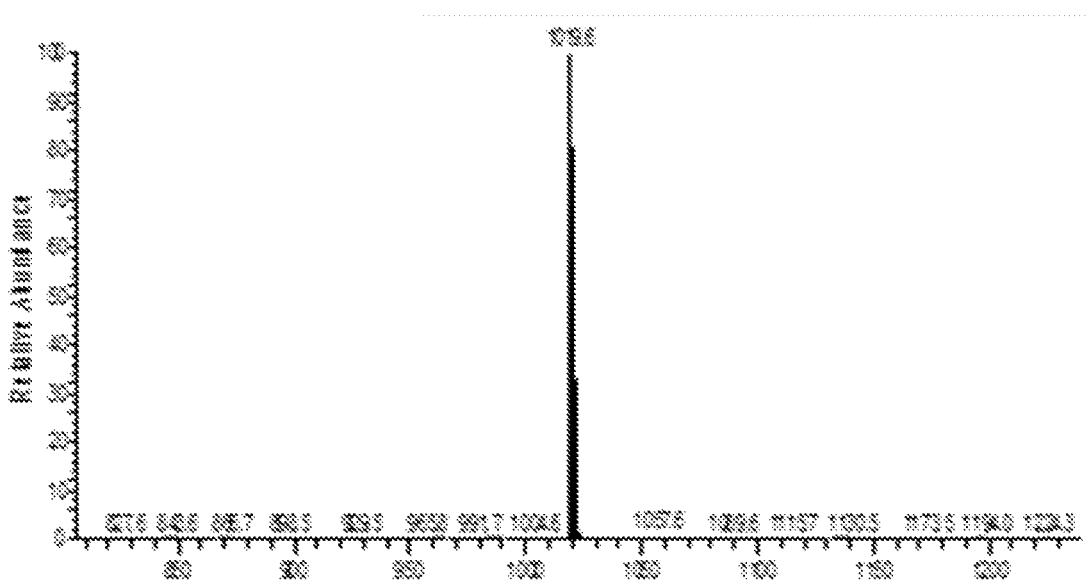

[FIG. 5]
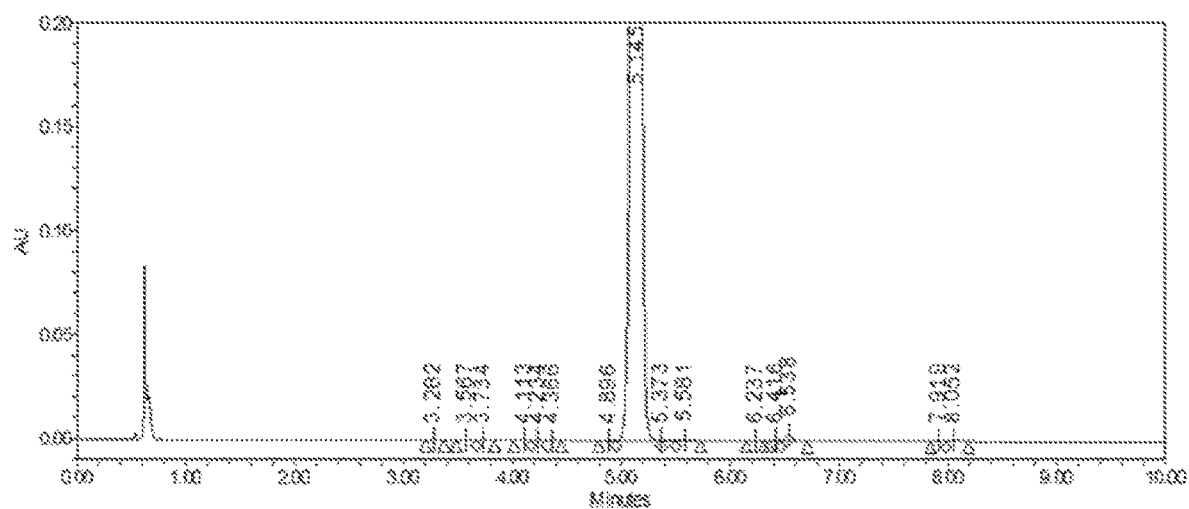

POLYMER, COATING COMPOSITION COMPRISING SAME, AND ORGANIC LIGHT EMITTING DEVICE USING SAME

CROSS-REFERENCE TO RELATED APPLICATIONS

This application is a national phase entry under 35 U.S.C. § 371 of International Application No. PCT/KR2019/010424 filed Aug. 16, 2019, which claims priority from Korean Patent Application No. 10-2018-0095968 filed Aug. 17, 2018, all of which are incorporated herein by reference.

TECHNICAL FIELD

The present specification relates to a polymer, a coating composition including the same, and an organic light emitting device formed using the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic electroluminescent device using such a principle may be generally formed with a cathode, an anode, and an organic material layer placed therebetween, for example, an organic material layer including a hole injection layer, a hole transfer layer, a light emitting layer, an electron transfer layer and an electron injection layer.

Materials used in an organic light emitting device are mostly pure organic materials or complex compounds in which organic materials and metals form complexes, and may be divided into hole injection materials, hole transfer materials, light emitting materials, electron transfer materials, electron injection materials and the like depending on the application. Herein, as the hole injection material or the hole transfer material, organic materials having a p-type property, that is, organic materials readily oxidized and having an electrochemically stable state when oxidized, are generally used. Meanwhile, as the electron injection material or the electron transfer material, organic materials having an n-type property, that is, organic materials readily reduced and having an electrochemically stable state when reduced, are generally used. As the light emitting material, materials having both a p-type property and an n-type property, that is, materials having a stable form in both oxidized and reduced states, are preferred, and materials having high light emission efficiency converting, when excitons are formed, the excitons to light are preferred.

In addition to the properties described above, it is preferred that materials used in an organic light emitting device additionally have properties as follows.

First, materials used in an organic light emitting device preferably have excellent thermal stability. This is due to joule heating produced by charge migration in the organic light emitting device. N,N'-di(1-naphthyl)-N,N'-diphenyl-(1,1'-biphenyl)-4,4'-diamine (NPB) normally used as a hole transfer layer material currently has a glass transition temperature of 100° C. or lower, and has a problem in that it is difficult to use in organic light emitting devices requiring a high current.

Second, in order to obtain a highly efficient organic light emitting device capable of low voltage driving, holes or electrons injected into the organic light emitting device need to be smoothly transferred to a light emitting layer, and at the same time, the injected holes and electrons need to be kept from escaping out of the light emitting layer. For this, materials used in the organic light emitting device need to have a proper band gap and a highest occupied molecular orbital (HOMO) or lowest unoccupied molecular orbital (LUMO) energy level. Poly(3,4-ethylenedioxythiophene) doped:poly(styrenesulfonic acid) (PEDOT:PSS) currently used as a hole transfer material in an organic light emitting device manufactured using a solution coating method has a lower LUMO energy level compared to a LUMO energy level of organic materials used as a light emitting layer material, and therefore, has a problem in manufacturing an organic light emitting device with high efficiency and long lifetime.

In addition thereto, materials used in an organic light emitting device need to have excellent chemical stability, charge mobility, and interface property with electrodes or adjacent layers. In other words, materials used in an organic light emitting device need to undergo less material deformation caused by moisture or oxygen. In addition, by having proper hole or electron mobility, the materials need to maximize exciton formation through balancing hole and electron density in a light emitting layer of the organic light emitting device. For device stability, the materials also need to improve an interface with electrodes including metals or metal oxides.

In addition to the properties described above, materials used in an organic light emitting device for a solution process additionally need to have properties as follows.

First, a storable homogeneous solution needs to be formed. Commercialized materials for a deposition process have favorable crystallinity, so are not well-dissolved in a solution, or crystals are readily caught when forming a solution. Therefore, a concentration gradient of the solution may change depending on the storage time or possibility of forming a defective device is high.

Second, layers going through a solution process need to have solvent and material tolerance for other layers. For this, materials capable of forming a self-crosslinked polymer on a substrate through heat treatment or ultraviolet (UV) irradiation after introducing a curing group and solution coating such as N4,N4'-di(naphthalen-1-yl)-N4,N4'-bis(4-vinylphenyl)biphenyl-4,4'-diamine (VNPB) or forming a polymer having sufficient tolerance for a next process are preferred, and materials capable of having solvent tolerance by itself such as hexaazatriphenylene hexacarbonitrile (HATCN) are also preferred. Arylamine-based monomers generally used in an organic light emitting device (OLED) do not have tolerance for a solvent of a next process by themselves, and therefore, arylamine-based monomer compounds usable in an OLED for a solution process need to have a curing group introduced thereto.

Accordingly, development of organic materials fulfilling such requirements has been required in the art.

PRIOR ART DOCUMENTS

Patent Documents

Korean Patent Application Laid-Open Publication No. 10-2004-0028954

DISCLOSURE

Technical Problem

The present specification is directed to providing a polymer, a coating composition including the same, and an organic light emitting device formed using the same.

Technical Solution

One embodiment of the present specification provides a polymer including a unit represented by the following Chemical Formula 1.

[Chemical Formula 1]

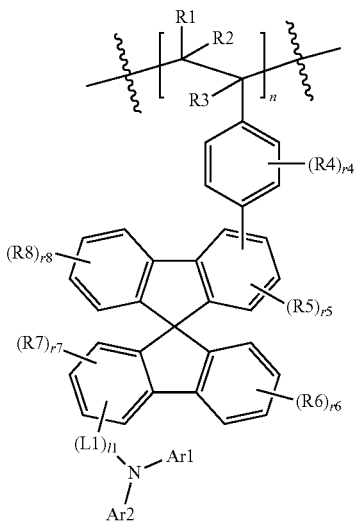

In Chemical Formula 1,

L1 is a direct bond; a substituted or unsubstituted phenylene group; a substituted or unsubstituted naphthylene group; a substituted or unsubstituted biphenylene group; a substituted or unsubstituted divalent fluorenyl group; or a substituted or unsubstituted divalent carbazolyl group, l1 is an integer of 1 to 10, Ar1 and Ar2 are the same as or different from each other, and each independently a substituted or unsubstituted aryl group; or a substituted or unsubstituted heteroaryl group, R1 to R8 are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group, r4, r6 and r8 are each an integer of 1 to 4, r5 and r7 are each an integer of 1 to 3, when r4 is 2 or greater, the two or more R4s are the same as or different from each other, when r5 is 2 or greater, the two or more R5s are the same as or different from each other, when r6 is 2 or greater, the two or more R6s are the same as or different from each other, when r7 is 2 or greater, the two or more R7s are the same as or different from each other, when r8 is 2 or greater, the two or more R8s are the same as or different from each other, when l1 is 2 or greater, the two or more Lis are the same as or different from each other, and n is, as a repetition number of the unit, an integer of 1 to 10,000.

Another embodiment of the present specification provides a monomer represented by the following Chemical Formula 2.

[Chemical Formula 2]

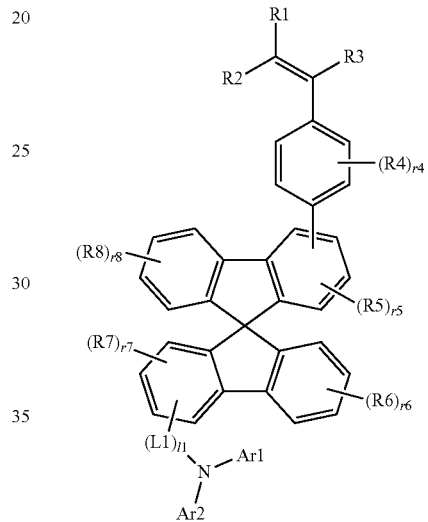

In Chemical Formula 2,

L1 is a direct bond; a substituted or unsubstituted phenylene group; a substituted or unsubstituted naphthylene group; a substituted or unsubstituted biphenylene group; a substituted or unsubstituted divalent fluorenyl group; or a substituted or unsubstituted divalent carbazolyl group, l1 is an integer of 1 to 10, Ar1 and Ar2 are the same as or different from each other, and each independently a substituted or unsubstituted aryl group; or a substituted or unsubstituted heteroaryl group, R1 to R8 are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group, r4, r6 and r8 are each independently an integer of 1 to 4, r5 and r7 are each independently an integer of 1 to 3, when r4 is 2 or greater, the two or more R4s are the same as or different from each other, when r5 is 2 or greater, the two or more R5s are the same as or different from each other, when r6 is 2 or greater, the two or more R6s are the same as or different from each other, when r7 is 2 or greater, the two or more R7s are the same as or different from each other, when r8 is 2 or greater, the two or more R8s are the same as or different from each other, and when l1 is 2 or greater, the two or more Lis are the same as or different from each other.

Another embodiment of the present specification provides a coating composition including the polymer including the unit represented by Chemical Formula 1.

Another embodiment of the present specification provides a coating composition including the monomer represented by Chemical Formula 2.

One embodiment of the present specification provides an organic light emitting device including a first electrode; a second electrode provided opposite to the first electrode; and one or more organic material layers provided between the first electrode and the second electrode, wherein one or more layers of the organic material layers include the polymer including the unit represented by Chemical Formula 1.

In addition, one embodiment of the present disclosure provides a method for manufacturing an organic light emitting device, the method including preparing a first electrode; forming one or more organic material layers on the first electrode; and forming a second electrode on the organic material layer, wherein the forming of one or more organic material layers includes forming an organic material layer using the coating composition including the polymer including the unit represented by Chemical Formula 1 described above or the coating composition including the monomer represented by Chemical Formula 2 described above, and the forming of an organic material layer using the coating composition includes coating the coating composition on the first electrode; and heat treating or light treating the coated coating composition.

Advantageous Effects

An organic material layer formed using a polymer including a unit represented by Chemical Formula 1 according to one embodiment of the present specification has very low solubility for some solvents, and therefore, a lamination process can be conducted on the organic material layer formed using the polymer through a solution process.

The polymer including the unit represented by Chemical Formula 1 according to one embodiment of the present specification has a high glass transition temperature due to specificity of the spirobifluorene structure, and in addition thereto, has low crystallinity due to low π-π stacking, and has excellent solubility for solvents.

In addition, the polymer according to one embodiment of the present specification can be used as a material of an organic material layer of an organic light emitting device to lower a driving voltage of the organic light emitting device.

In addition, the polymer according to one embodiment of the present specification can be used as a material of an organic material layer of an organic light emitting device to enhance light efficiency.

In addition, the polymer according to one embodiment of the present specification can be used as a material of an organic material layer of an organic light emitting device to enhance lifetime properties of the device.

DESCRIPTION OF DRAWINGS

FIG. 1 illustrates an example of an organic light emitting device according to one embodiment of the present specification.

FIG. 2 is a diagram presenting LC-MS data of Monomer 1.

FIG. 3 is a diagram presenting an HPLC analysis graph of Monomer 1.

FIG. 4 is a diagram presenting LC-MS data of Monomer 2.

FIG. 5 is a diagram presenting an HPLC analysis graph of Monomer 2.

REFERENCE NUMERAL

101: Substrate
201: First Electrode
301: Hole Injection Layer
401: Hole Transfer Layer
501: Light Emitting Layer
601: Electron Transfer Layer
701: Second Electrode

MODE FOR DISCLOSURE

Hereinafter, the present specification will be described in more detail.

One embodiment of the present specification provides a polymer including a unit represented by Chemical Formula 1.

One embodiment of the present specification also provides a monomer represented by Chemical Formula 2.

In one embodiment of the present specification, the polymer including the unit represented by Chemical Formula 1 is a random polymer or a block polymer.

In the present specification, a "unit" is a structure of a monomer being included and repeated in a polymer, and means a structure of a monomer bonding in a polymer by polymerization.

In the present specification, the meaning of "including a unit" means the corresponding unit being included in a main chain in a polymer.

In the present specification, the "monomer" means a monomer or a unit structure becoming a unit forming the polymer.

In one embodiment of the present specification, the unit represented by Chemical Formula 1 includes spirobifluorene, and thereby minimizes steric hindrance compared to units including fluorene or carbazole used in the art, and as a result, a degree of curing of a polymer including the same may increase.

In addition, the polymer including the unit represented by Chemical Formula 1 has solvent tolerance (solvent orthogonality) for some solvents, and therefore, other organic material layers may be formed on the organic material layer formed using the polymer including the unit represented by Chemical Formula 1 using a solution process.

When using the polymer including the unit represented by Chemical Formula 1 in a hole transfer layer, a hole injection layer, or a layer carrying out hole transfer and injection at the same time of an organic light emitting device, the prepared hole transfer layer, hole injection layer, or layer carrying out hole transfer and injection at the same time has excellent uniformity and surface properties as well, and therefore, device performance and lifetime properties may be enhanced.

In addition, the polymer including the unit represented by Chemical Formula 1 may have its molecular weight readily controlled compared to monomolecular compounds including spirobifluorene, and viscosity of a solution including the same may also be readily controlled.

An organic material layer may be formed using a solution process when using the polymer according to one embodiment of the present specification. In one embodiment, the polymer including the unit represented by Chemical Formula 1 according to the present disclosure may be dissolved in solvents such as tetrahydrofuran (THF); or toluene, however, the solvent is not limited thereto.

The polymer including the unit represented by Chemical Formula 1 according to one embodiment of the present specification has solvent orthogonality for solvents such as cycloketone; cycloalkane; or dioxane.

In one embodiment, the organic material layer including the polymer including the unit represented by Chemical Formula 1 has solubility of 0.05 wt % or less for cyclohexanone.

In one embodiment, the organic material layer including the polymer including the unit represented by Chemical Formula 1 has solubility of 0.05 wt % or less for dioxane.

In one embodiment, the organic material layer including the polymer including the unit represented by Chemical Formula 1 has solubility of 0.05 wt % or less for cyclohexane. In one embodiment, the organic material layer including the polymer including the unit represented by Chemical Formula has solubility of 0 wt % or greater for cyclohexane; cyclohexanone; or dioxane.

In one embodiment, whether the organic material layer is dissolved in a specific solvent may be identified by immersing the corresponding organic material layer in a solvent to measure the solubility, taking out the organic material layer, and measuring a difference in the UV absorption values of the organic material layer before and after being exposed to the specific solvent. Herein, the organic material layer exposed to the solvent may have a form of a single layer of the organic material layer, or may be a laminate having a form of providing the corresponding organic material layer on an outermost layer. A laminate having a form of providing the organic material layer on an outermost layer means, in a laminate in which two or more layers are consecutively laminated, a structure having a form of providing the corresponding organic material layer as the last layer in a laminated direction of the layers.

More specifically, when UV absorption intensity of an organic material layer in a maximum absorption wavelength before being exposed to a specific solvent is employed as a, and UV absorption intensity of the organic material layer in a maximum absorption wavelength after being exposed to the specific solvent is employed as b, b/a*100 is 97% or greater. When b/a*100 is greater than or equal to 97% and less than or equal to 100%, it may be understood to have solvent orthogonality for the specific solvent.

In one embodiment, materials forming a specific organic material layer of an organic light emitting device may be analyzed through MS and NMR analyses after extracting the corresponding organic material layer from the organic light emitting device.

In one embodiment, when forming an organic material layer having a thickness of 20 nm by spin coating a composition obtained by dissolving the polymer including the unit represented by Chemical Formula 1 in toluene in 2 wt % on a glass plate and heat treating the result for 30 minutes at 230° C., solubility of the organic material layer for cyclohexanone is 0.05 wt % or less.

In one embodiment, when forming an organic material layer having a thickness of 20 nm by spin coating a composition obtained by dissolving the polymer including the unit represented by Chemical Formula 1 in toluene in 2 wt % on a glass plate and heat treating the result for 30 minutes at 230° C., solubility of the organic material layer for dioxane is 0.05 wt % or less.

In one embodiment, when forming an organic material layer having a thickness of 20 nm by spin coating a composition obtained by dissolving the polymer including the unit represented by Chemical Formula 1 in toluene in 2 wt % on a glass plate and heat treating the result for 30 minutes at 230° C., solubility of the organic material layer for cyclohexane is 0.05 wt % or less.

In the present specification,

means a site bonding to other substituents or bonding sites.

In the present specification, a description of a certain member being placed "on" another member includes not only a case of the one member adjoining the another member but a case of still another member being present between the two members.

In the present specification, a description of a certain part "including" certain constituents means capable of further including other constituents, and does not exclude other constituents unless particularly stated on the contrary.

Examples of substituents in the present specification will be described below in detail, however, the substituents are not limited thereto.

The term "substitution" means a hydrogen atom bonding to a carbon atom of a compound is changed to another substituent. The position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one or more substituents selected from the group consisting of deuterium; a halogen group; a hydroxyl group; a cyano group; an alkyl group; a cycloalkyl group; an alkenyl group; an alkoxy group; an aryloxy group; an amine group; an aryl group; and a heteroaryl group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification, examples of the halogen group may include fluorine, chlorine, bromine or iodine.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthrenyl group, a triphenylenyl group, a pyrenyl group, a phenalenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted, the substituted fluorenyl group may be, for example, any one selected from among the following compounds, but is not limited thereto.

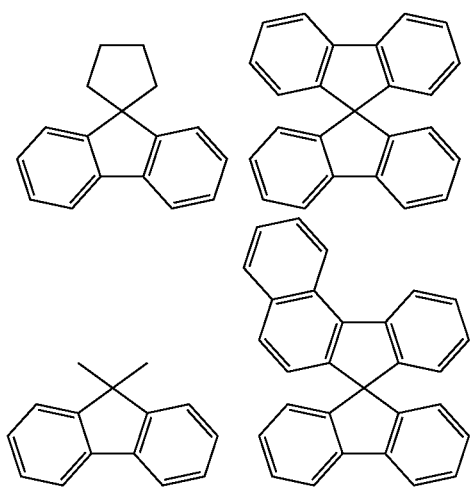

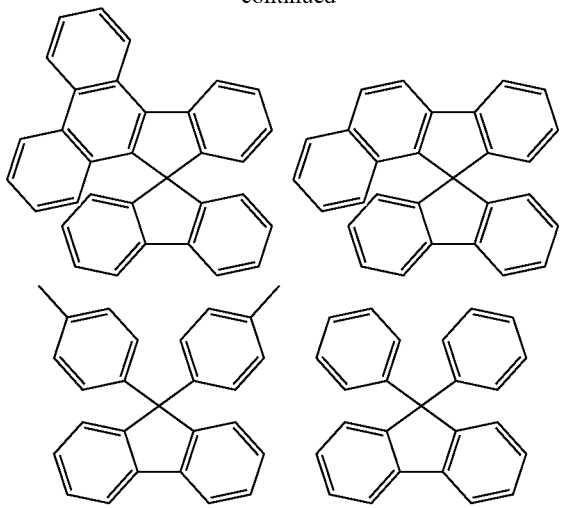

In the present specification, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the heteroaryl group includes one or more atoms that are not carbon, that is, heteroatoms, and specifically, the heteroatom may include one or more atoms selected from the group consisting of O, N, Se and S. The number of carbon atoms is not particularly limited, but is preferably from 2 to 30, and the heteroaryl group may be monocyclic or polycyclic. Examples of the heterocyclic group may include a thiophenyl group, a furanyl group, a pyrrolyl group, an imidazolyl group, a triazolyl group, an oxazolyl group, an oxadiazolyl group, a pyridinyl group, a bipyridinyl group, a pyrimidinyl group, a triazinyl group, a triazolyl group, an acridinyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthridinyl group, a phenanthrolinyl group, an isoxazolyl group, a thiadiazolyl group, a phenothiazinyl group, a dibenzofuranyl group and the like, but are not limited thereto.

In the present specification, the aryl group in the aryloxy group is the same as the examples of the aryl group described above. Specific examples of the aryloxy group may include a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthryloxy group, a 1-phenanthrenyloxy group, a 3-phenanthrenyloxy group, a 9-phenanthrenyloxy group and the like, but are not limited thereto.

In the present specification, the amine group may be selected from the group consisting of —NH$_2$, an alkylamine group, an N-alkylarylamine group, an arylamine group, an N-arylheteroarylamine group, an N-alkylheteroarylamine group and a heteroarylamine group, and although not particularly limited thereto, the number of carbon atoms is preferably from 1 to 30.

Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group and the like, but are not limited thereto.

In the present specification, the N-alkylarylamine group means an amine group in which N of the amine group is substituted with an alkyl group and an aryl group. The alkyl group and the aryl group in the N-alkylarylamine group are the same as the examples of the alkyl group and the aryl group described above.

In the present specification, the N-arylheteroarylamine group means an amine group in which N of the amine group is substituted with an aryl group and a heteroaryl group. The aryl group and the heteroaryl in the N-arylheteroarylamine group are the same as the examples of the aryl group and the heteroaryl group described above.

In the present specification, the N-alkylheteroarylamine group means an amine group in which N of the amine group is substituted with an alkyl group and a heteroaryl group. The alkyl group and the heteroaryl in the N-alkylheteroarylamine group are the same as the examples of the alkyl group and the heteroaryl group described above.

In the present specification, examples of the alkylamine group include a substituted or unsubstituted monoalkylamine group, or a substituted or unsubstituted dialkylamine group. The alkyl group in the alkylamine group may be a linear or branched alkyl group. The alkylamine group including two or more alkyl groups may include linear alkyl groups, branched alkyl groups, or both linear alkyl groups and branched alkyl groups. For example, the alkyl group in the alkylamine group may be selected from among the examples of the alkyl group described above.

In the present specification, examples of the arylamine group include a substituted or unsubstituted arylamine group, or a substituted or unsubstituted diarylamine group. The diarylamine group may include monocyclic aryl groups, polycyclic aryl groups, or both a monocyclic aryl group and a polycyclic aryl group. For example, the aryl group in the arylamine group may be selected from among the examples of the aryl group described above.

In the present specification, examples of the heteroarylamine group include a substituted or unsubstituted monoheteroarylamine group, or a substituted or unsubstituted diheteroarylamine group. The diheteroarylamine group may include monocyclic heteroaryl groups, polycyclic heteroaryl groups, or both a monocyclic heteroaryl group and a polycyclic heteroaryl group. For example, the heteroaryl group in the heteroarylamine group may be selected from among the examples of the heteroaryl group described above.

In the present specification, the arylene group means an aryl group having two bonding sites, that is, a divalent group. Descriptions on the aryl group provided above may be applied thereto except for those that are each divalent.

In the present specification, the heteroarylene group means a heteroaryl group having two bonding sites, that is, a divalent group. Descriptions on the heteroaryl group provided above may be applied thereto except for those that are each divalent.

According to one embodiment of the present specification, in Chemical Formula 1, R1 to R8 are hydrogen.

According to one embodiment of the present specification, the unit represented by Chemical Formula 1 is represented by the following Chemical Formula 1-1.

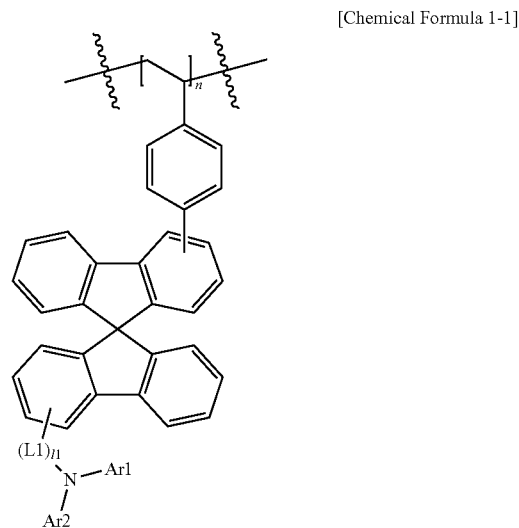

[Chemical Formula 1-1]

In Chemical Formula 1-1,

L1, l1, Ar1, Ar2 and n have the same definitions as in Chemical Formula 1.

According to one embodiment of the present specification, Chemical Formula 1 is represented by the following Chemical Formula 1-2.

[Chemical Formula 1-2]

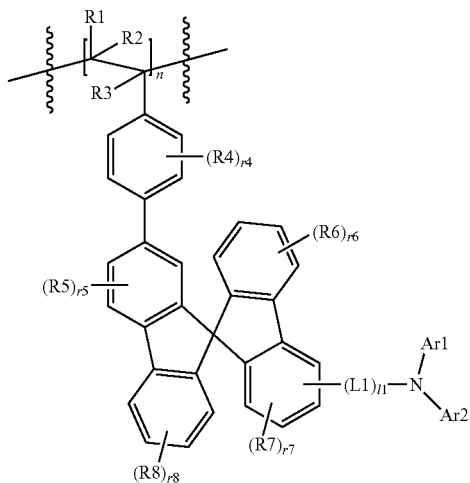

In Chemical Formula 1-2,

L1, l1, Ar1, Ar2, n, R1 to R8 and r4 to r8 have the same definitions as in Chemical Formula 1.

According to one embodiment of the present specification, Chemical Formula 1 is represented by the following Chemical Formula 1-3.

[Chemical Formula 1-3]

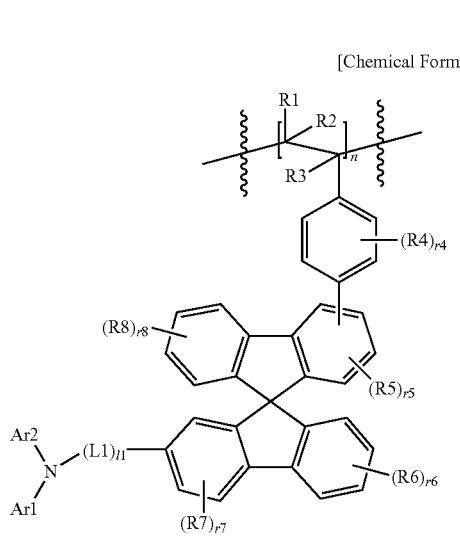

In Chemical Formula 1-3,

L1, l1, Ar1, Ar2, n, R1 to R8 and r4 to r8 have the same definitions as in Chemical Formula 1.

According to one embodiment of the present specification, Chemical Formula 1 is represented by the following Chemical Formula 1-4.

[Chemical Formula 1-4]

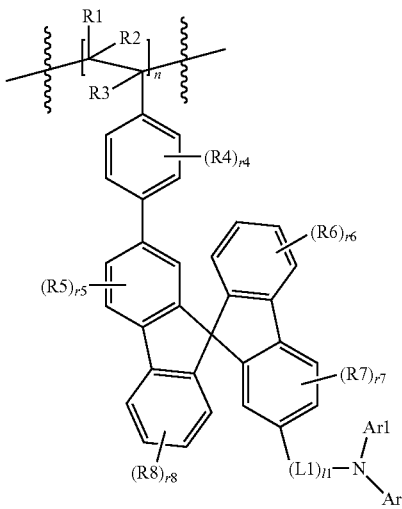

In Chemical Formula 1-4,

L1, l1, Ar1, Ar2, n, R1 to R8 and r4 to r8 have the same definitions as in Chemical Formula 1.

According to one embodiment of the present specification, Chemical Formula 2 is represented by the following Chemical Formula 2-2.

[Chemical Formula 2-2]

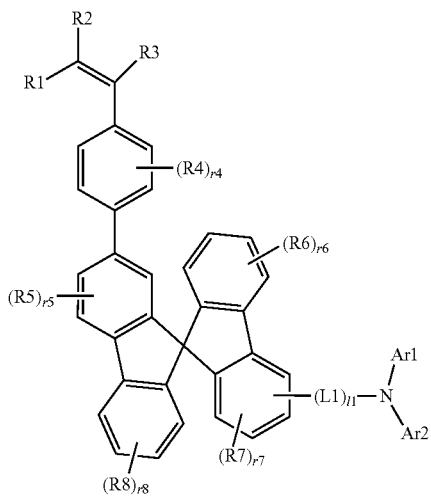

In Chemical Formula 2-2,

L1, l1, Ar1, Ar2, n, R1 to R8 and r4 to r8 have the same definitions as in Chemical Formula 2.

According to one embodiment of the present specification, Chemical Formula 2 is represented by the following Chemical Formula 2-3.

[Chemical Formula 2-3]

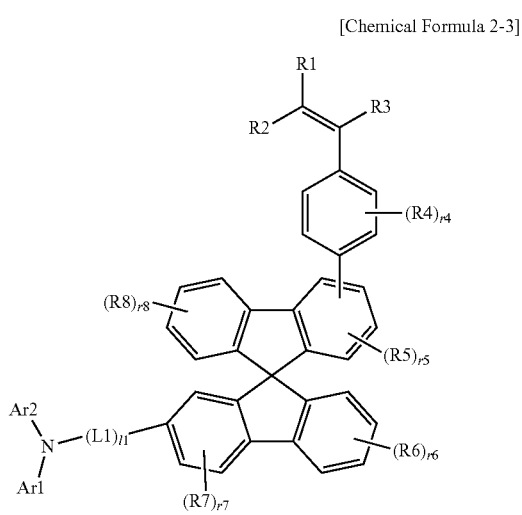

In Chemical Formula 2-3,

L1, l1, Ar1, Ar2, n, R1 to R8 and r4 to r8 have the same definitions as in Chemical Formula 2.

According to one embodiment of the present specification, Chemical Formula 2 is represented by the following Chemical Formula 2-4.

[Chemical Formula 2-4]

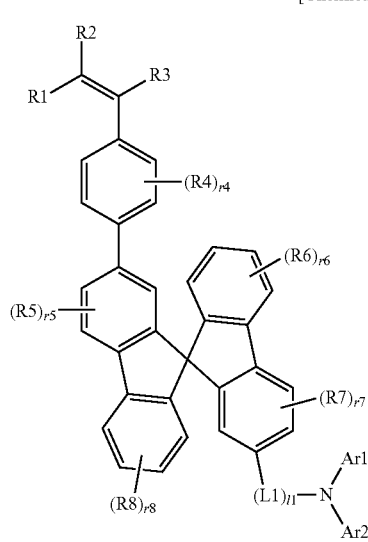

In Chemical Formula 2-4,

L1, l1, Ar1, Ar2, n, R1 to R8 and r4 to r8 have the same definitions as in Chemical Formula 2.

According to one embodiment of the present specification, in Chemical Formulae 1 and 2, L1 is a direct bond; a phenylene group unsubstituted or substituted with an alkyl group; a naphthylene group; a biphenylene group; a divalent fluorenyl group unsubstituted or substituted with an alkyl group; or a divalent carbazolyl group unsubstituted or substituted with an aryl group.

According to one embodiment of the present specification, in Chemical Formulae 1 and 2, L1 is a direct bond; a phenylene group unsubstituted or substituted with a methyl group; a naphthylene group; a biphenylene group; a divalent fluorenyl group unsubstituted or substituted with a methyl group; or a divalent carbazolyl group unsubstituted or substituted with a phenyl group.

According to one embodiment of the present specification, in Chemical Formulae 1 and 2, L1 is a direct bond, or any one selected from among the following structures.

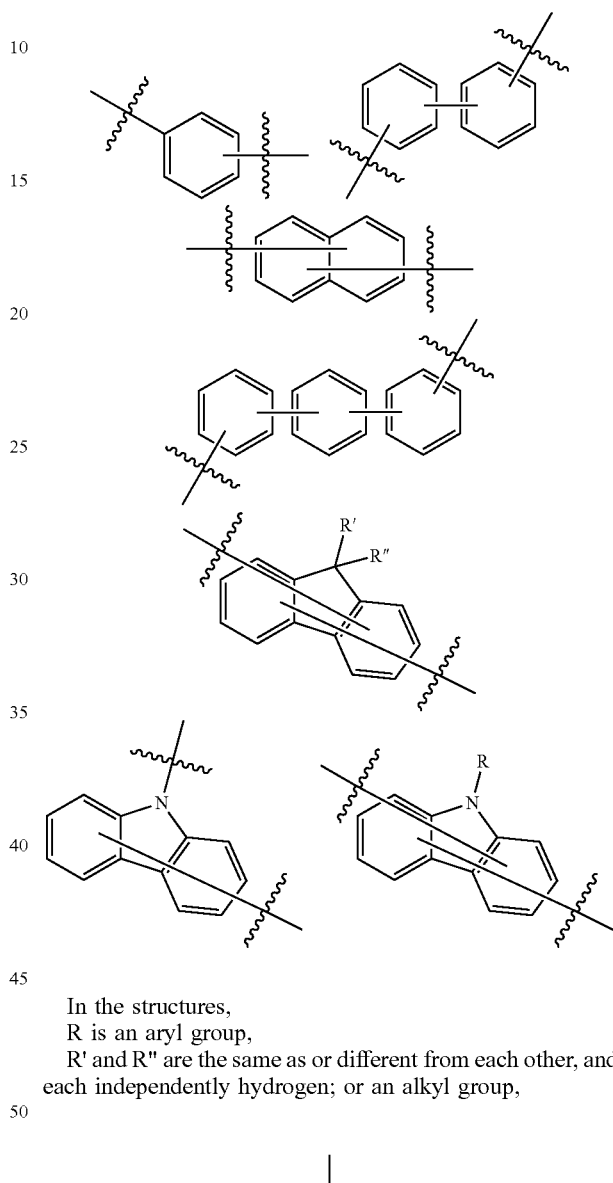

In the structures,

R is an aryl group,

R' and R" are the same as or different from each other, and each independently hydrogen; or an alkyl group,

is a site bonding to the spirobifluorene core or N of Chemical Formula 1, and the structures may be further substituted with an alkyl group.

According to one embodiment of the present specification, R is a phenyl group.

According to one embodiment of the present specification, R' and R" are the same as or different from each other, and each independently hydrogen; or a methyl group.

According to one embodiment of the present specification, R' and R" are hydrogen.

According to one embodiment of the present specification, R' and R" are a methyl group.

According to one embodiment of the present specification, L1 is a direct bond, or any one selected from among the following structures, and the following structures may be further substituted with an alkyl group.

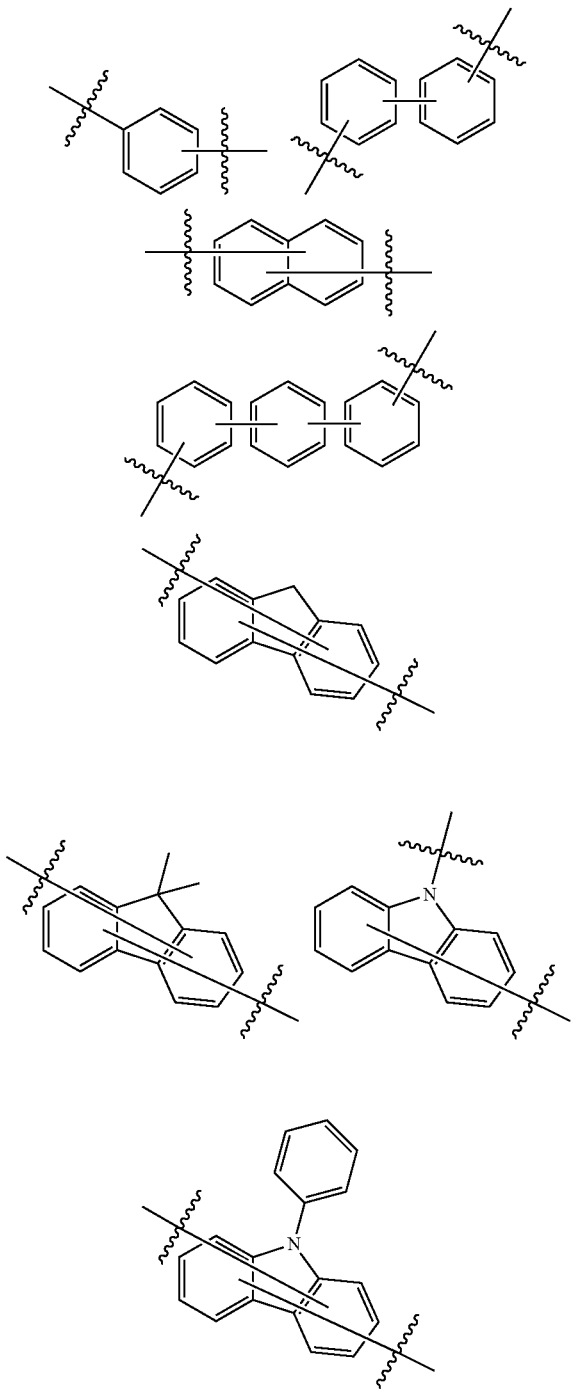

According to one embodiment of the present specification, L1 is any one selected from among the following structures, and the following structures may be further substituted with an alkyl group.

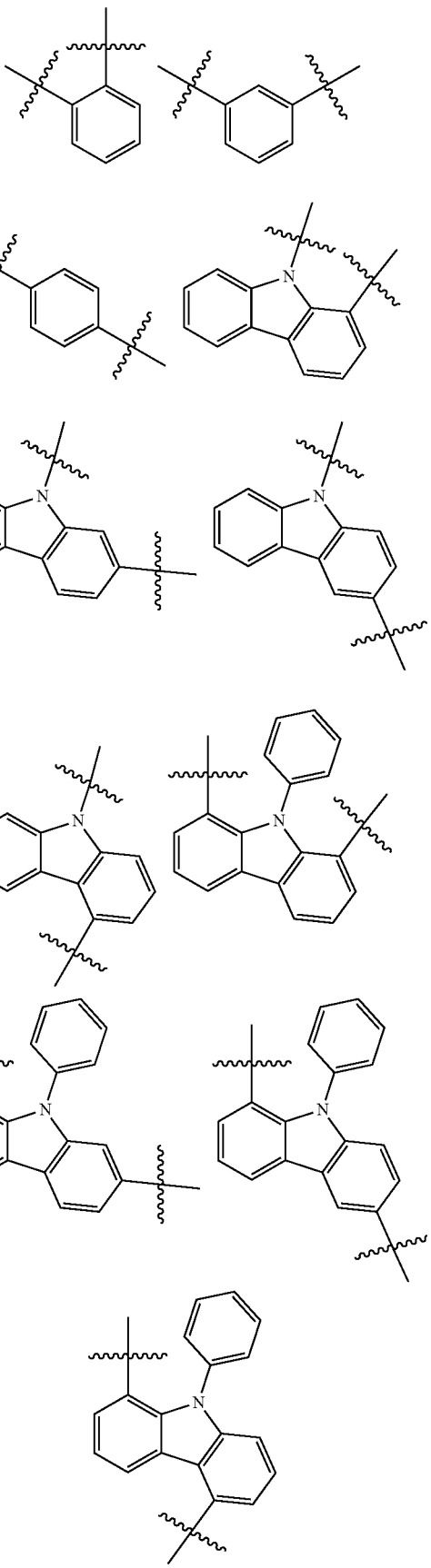

-continued
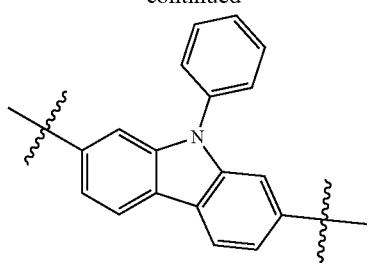
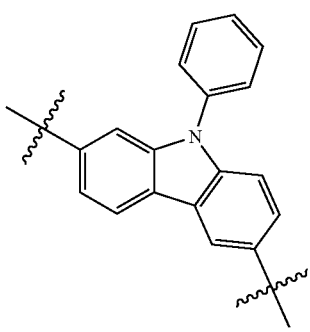
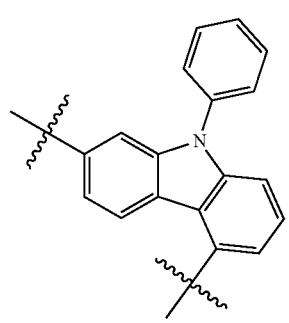
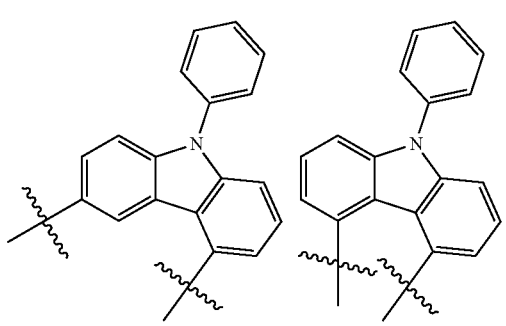
-continued
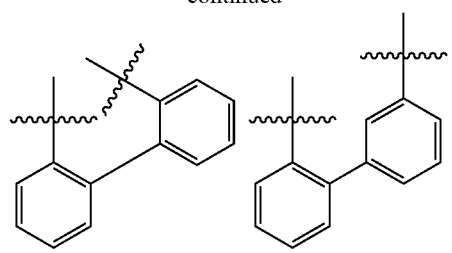
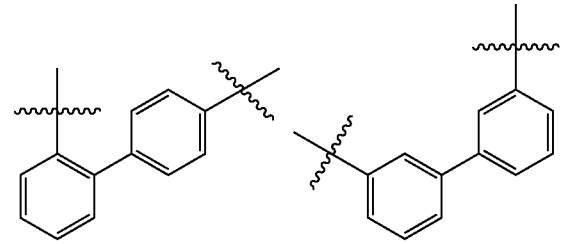
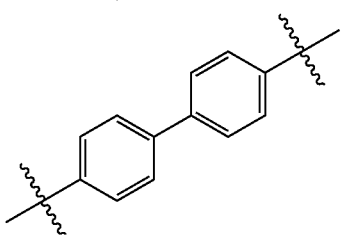
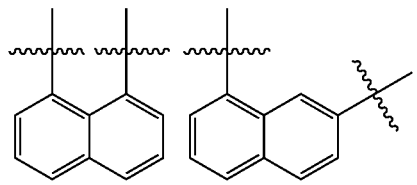
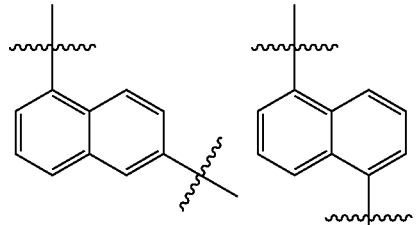
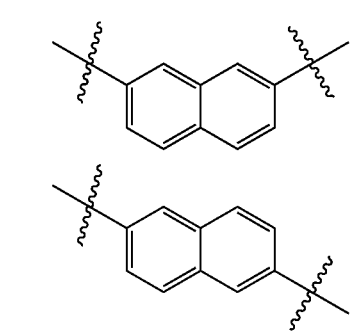
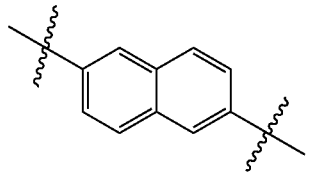

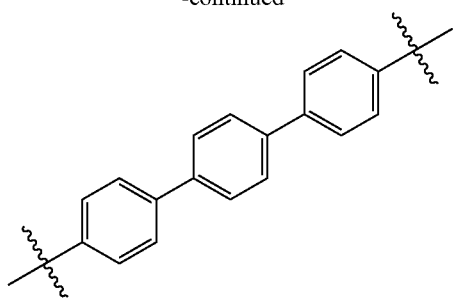
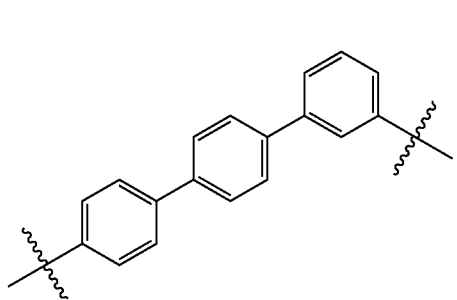
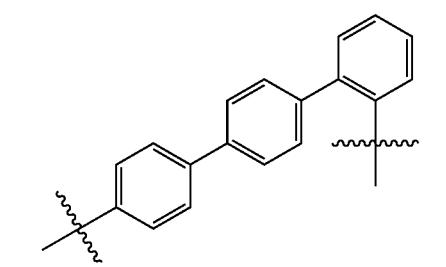
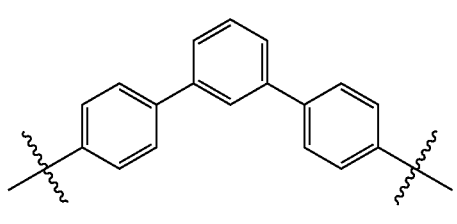
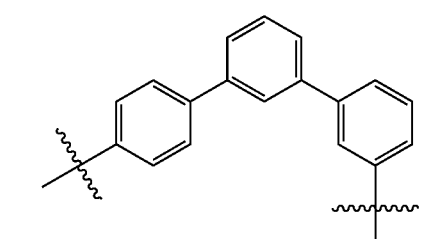
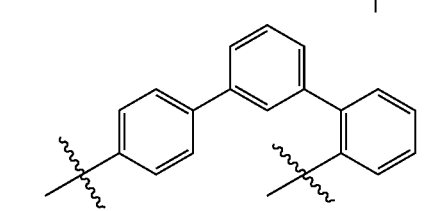
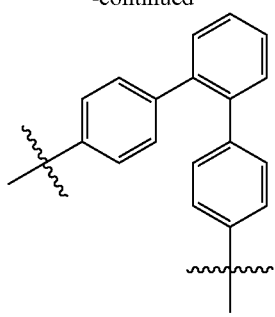
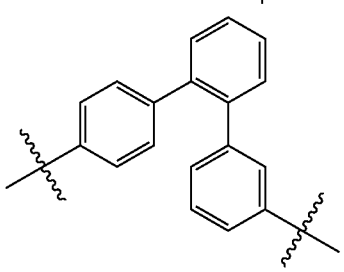
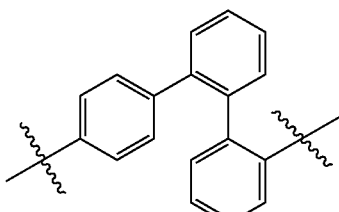
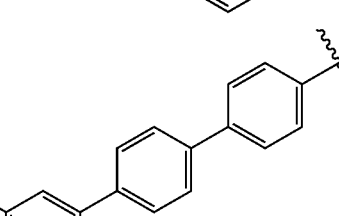
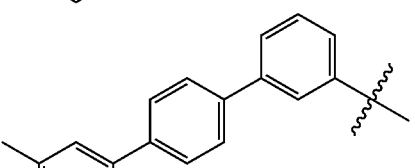
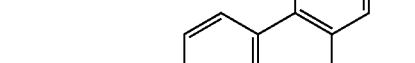
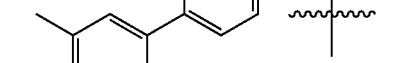
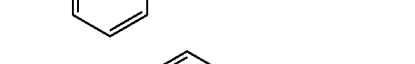
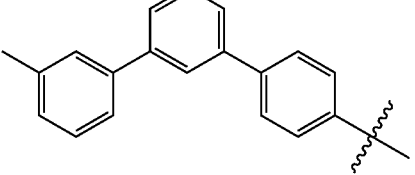

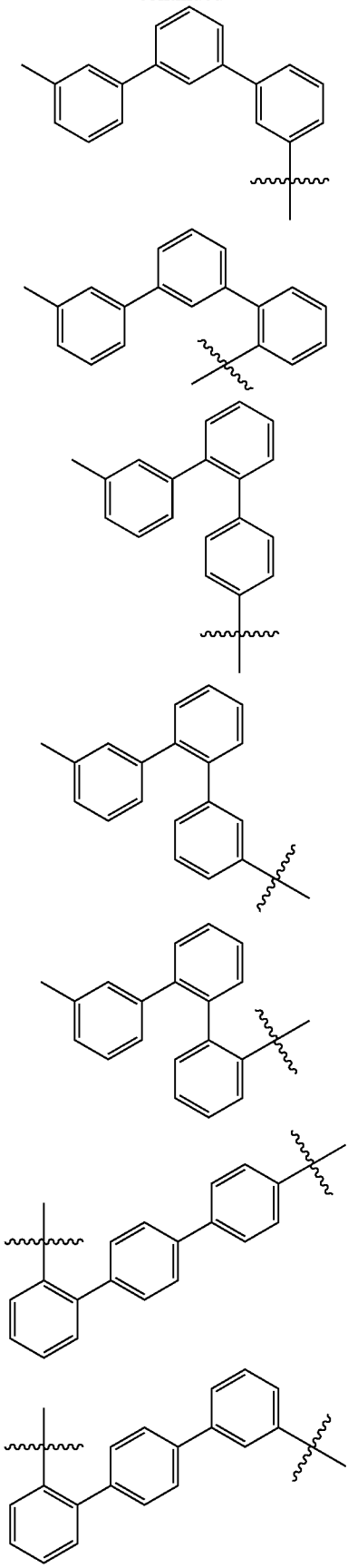
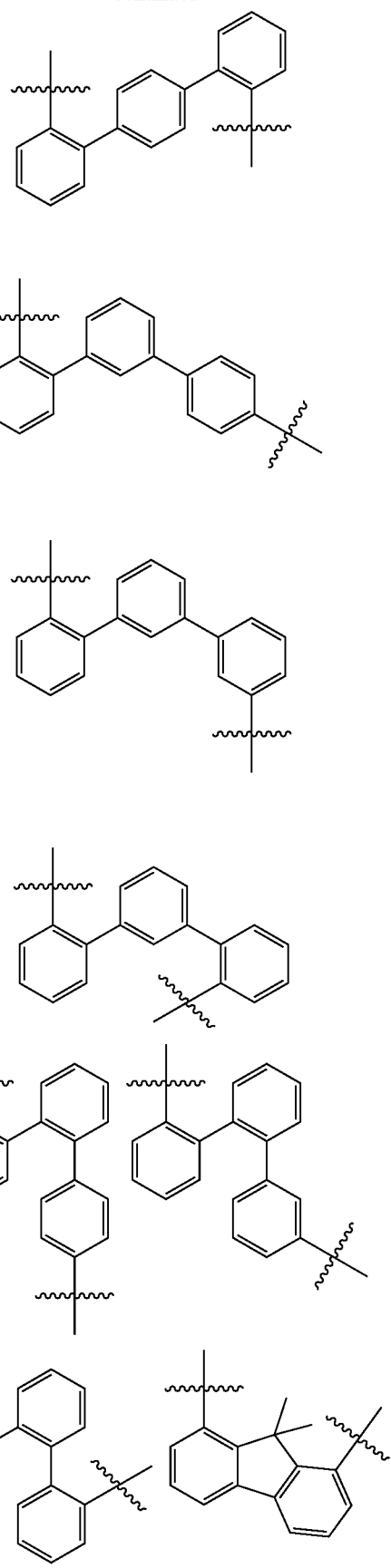

-continued
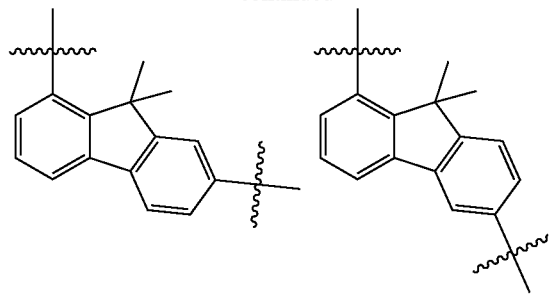
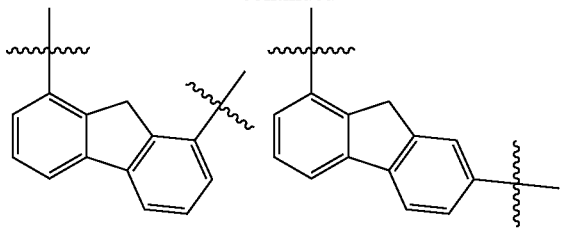
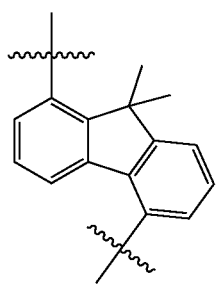
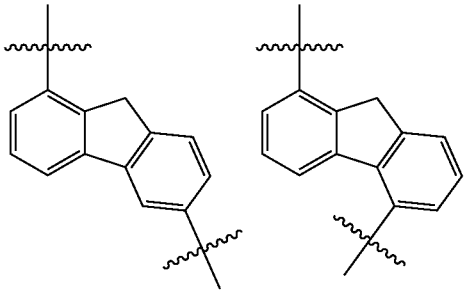
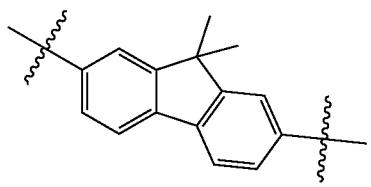
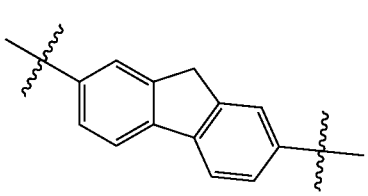
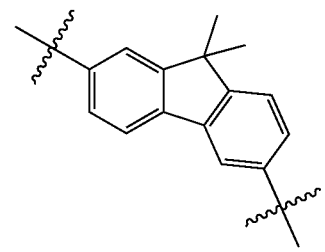
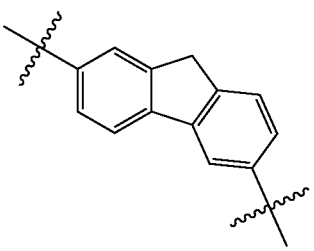
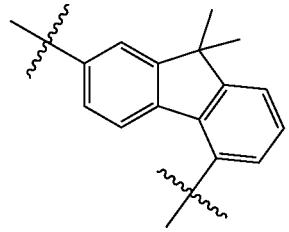 [SMILES: *c1ccc2c(c1)C(C)(C)c1cccc(*)c1-2]
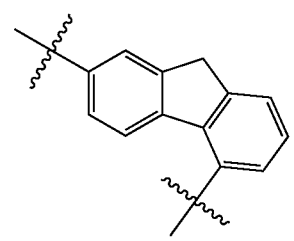
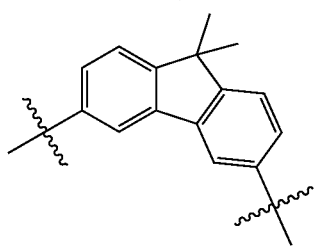
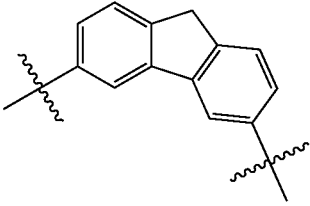
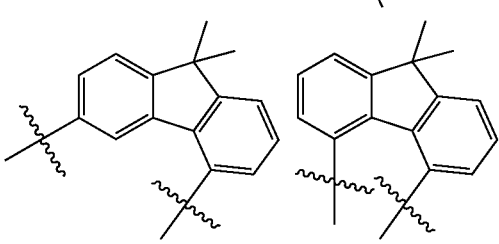
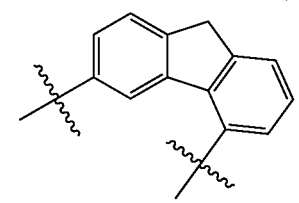

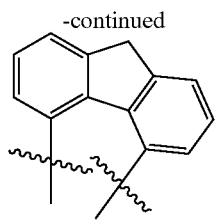

According to one embodiment of the present specification, when l1 is 2 or greater, Lis are linked in a series structure.

For example, when L1 is a divalent carbazolyl group; or a phenylene group, and l1 is 2, the structure may be

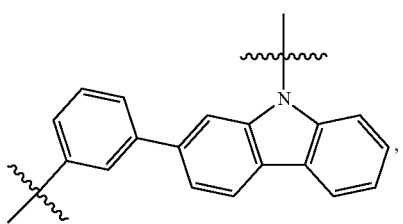 [SMILES: *c1cccc(-c2ccc3c4ccccc4n(*)c3c2)c1]

and the linked structure is not limited thereto.

According to one embodiment of the present specification, when l1 is 2 or greater, Lis are linked in a series structure. For example, when L1 is a divalent carbazolyl group; or a phenylene group, and l1 is 3, the structure may be

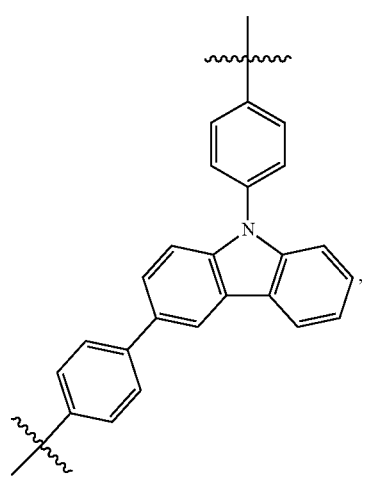 [SMILES: *c1ccc(-c2ccc3c(c2)c2ccccc2n3-c2ccc(*)cc2)cc1]

and the linked structure is not limited thereto.

According to one embodiment of the present specification, l1 is an integer of 1 to 4.

According to one embodiment of the present specification, l1 is an integer of 1 to 3.

According to one embodiment of the present specification, l1 is 1.

According to one embodiment of the present specification, l1 is 2.

According to one embodiment of the present specification, l1 is 3.

According to one embodiment of the present specification, Ar1 and Ar2 are the same as or different from each other, and each independently an aryl group unsubstituted or substituted with an aryl group; an aryl group substituted with a heteroaryl group; an aryl group substituted with an alkyl group; an aryl group substituted with an aryl group substituted with an alkyl group; an aryl group substituted with a heteroaryl group substituted with an aryl group; or a heteroaryl group unsubstituted or substituted with an aryl group.

According to one embodiment of the present specification, Ar1 and Ar2 are the same as or different from each other, and each independently a phenyl group unsubstituted or substituted with an aryl group; a biphenyl group; a phenyl group substituted with a heteroaryl group; a fluorenyl group substituted with an alkyl group; a phenyl group substituted with an aryl group substituted with an alkyl group; a phenyl group substituted with a heteroaryl group substituted with an aryl group; a carbazolyl group unsubstituted or substituted with an aryl group; or a spirobifluorenyl group.

According to one embodiment of the present specification, Ar1 and Ar2 are the same as or different from each other, and each independently a phenyl group unsubstituted or substituted with a phenyl group; a biphenyl group; a phenyl group substituted with a dibenzofuranyl group; a phenyl group substituted with a dimethylfluorenyl group; a fluorenyl group substituted with a methyl group; a phenyl group substituted with a fluorenyl group substituted with a methyl group; a phenyl group substituted with a carbazolyl group substituted with a phenyl group; a carbazolyl group unsubstituted or substituted with a phenyl group; or a spirobifluorenyl group.

According to one embodiment of the present specification, Ar1 and Ar2 are the same as or different from each other, and each independently a phenyl group; a biphenyl group; a 9,9-dimethylfluorenyl group; a 9-phenylcarbazolyl group; a phenyl group substituted with a 9-phenylcarbazolyl group; a phenyl group substituted with a dibenzofuranyl group; or a 9,9'-spirobifluorenyl group.

According to one embodiment of the present specification, the unit represented by Chemical Formula 1 is selected from among the following structures.

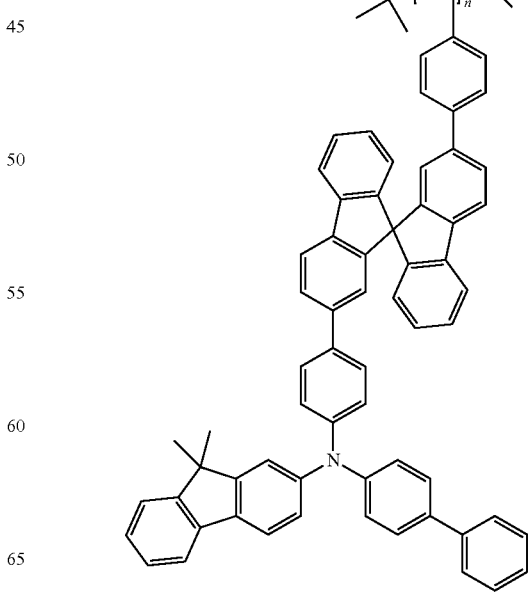

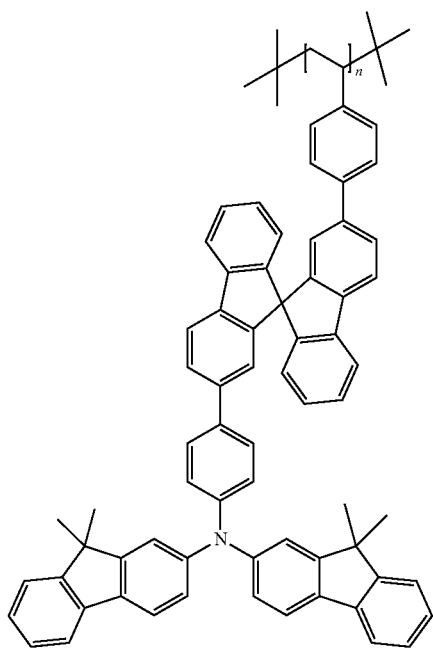
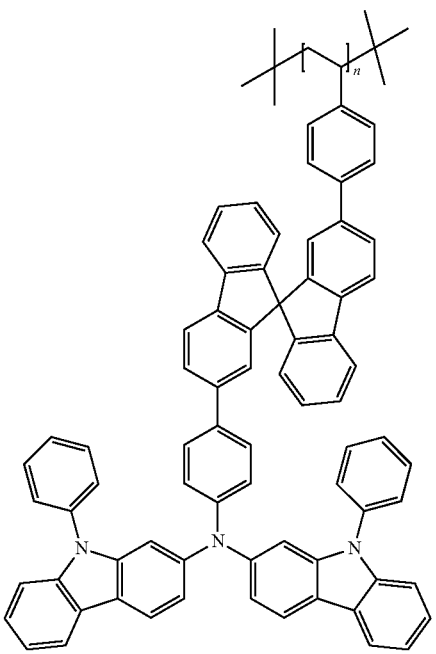
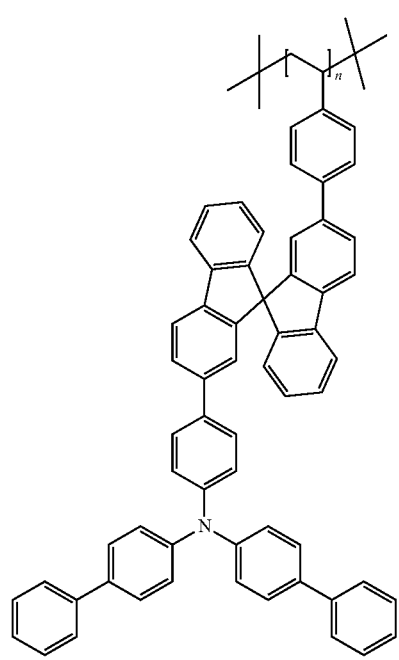
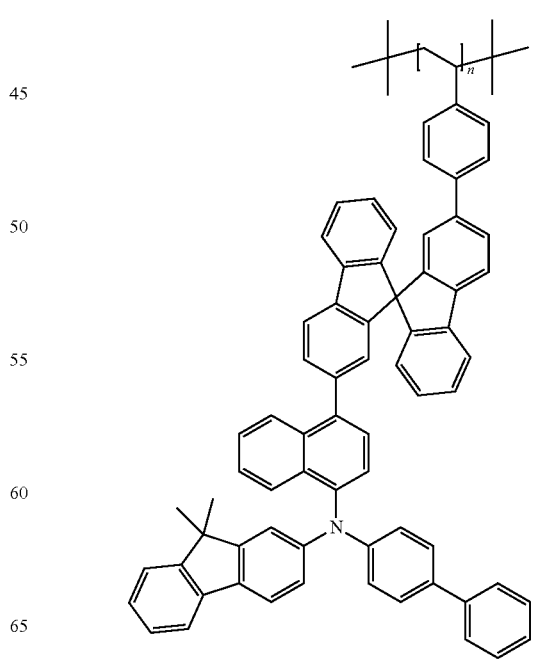

31
-continued
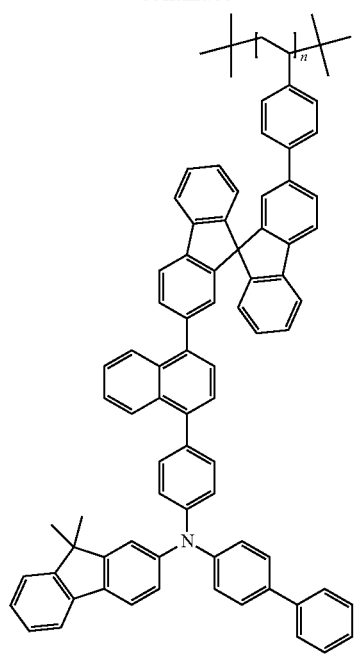
32
-continued
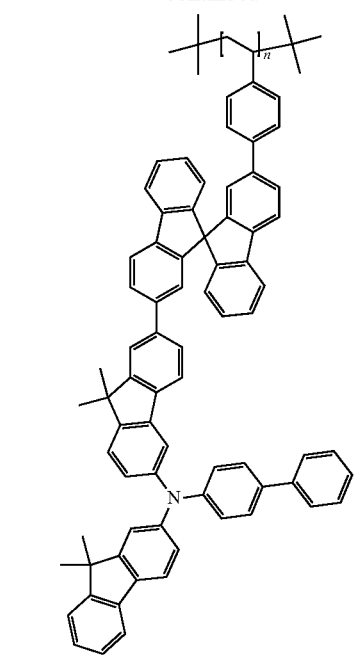
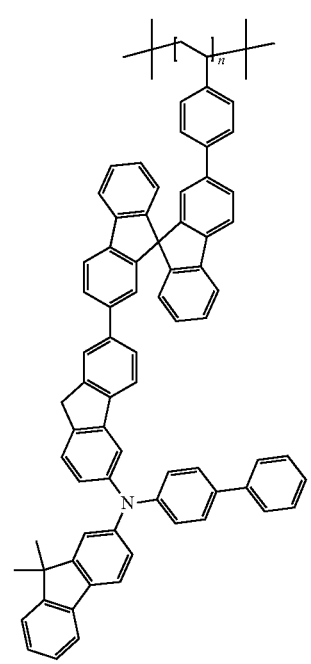
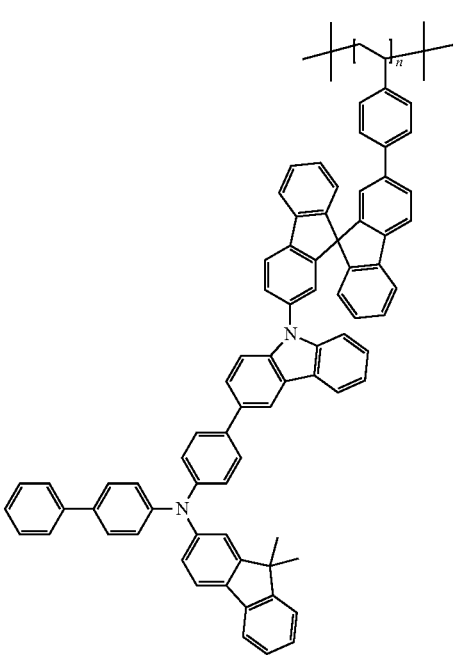

33
-continued
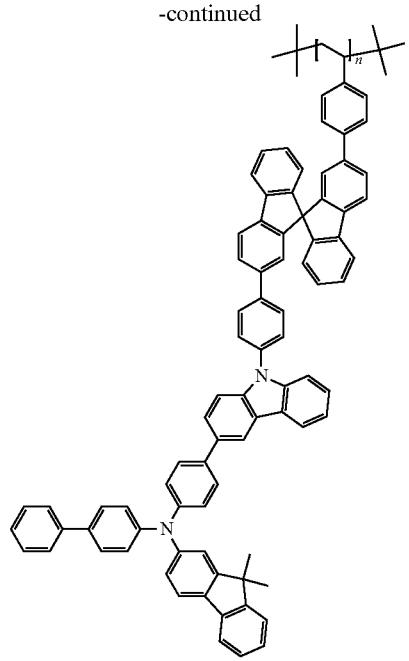
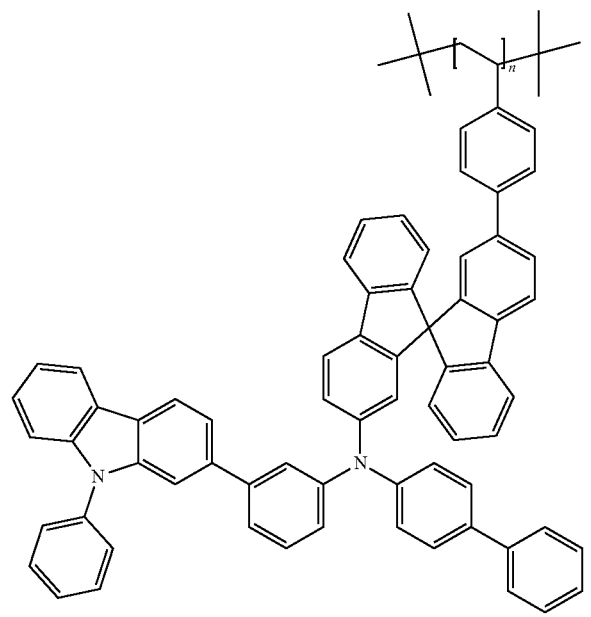
34
-continued
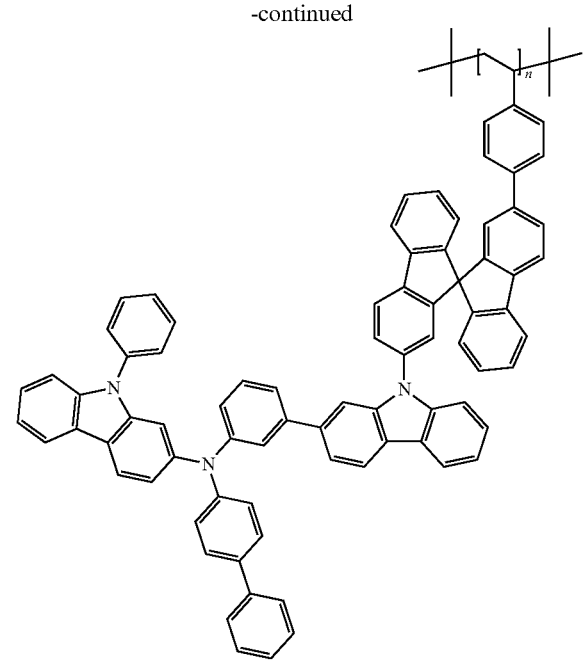
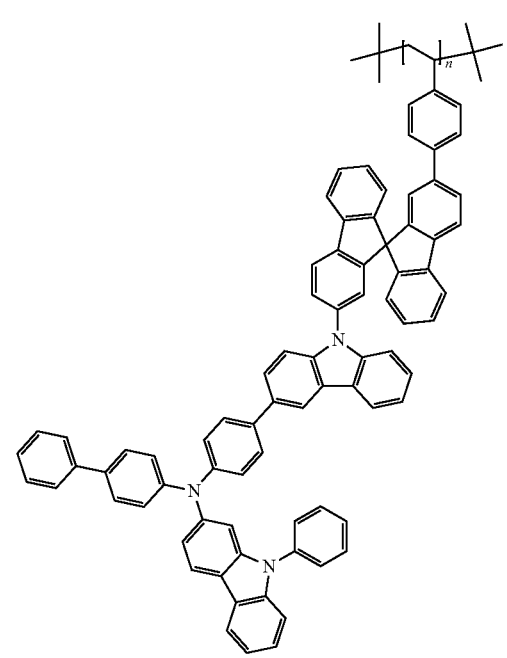

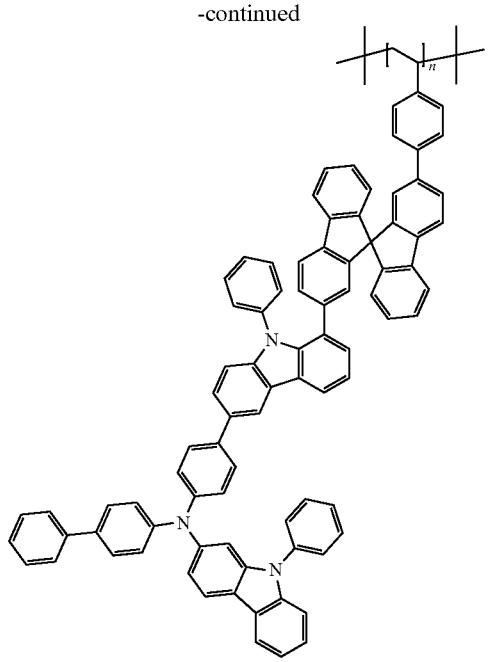
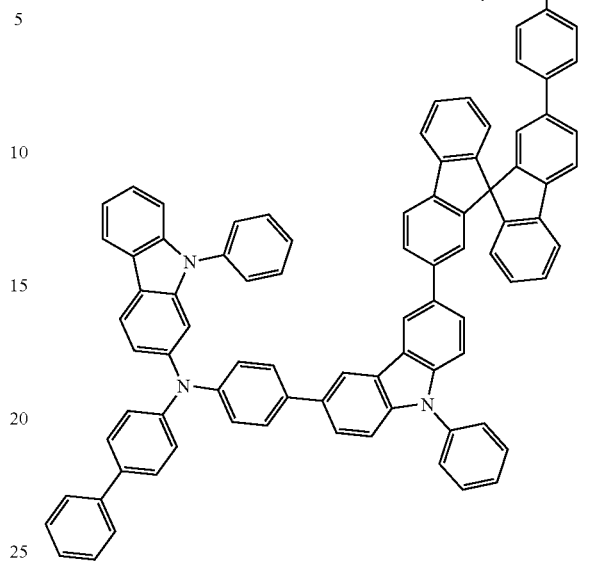
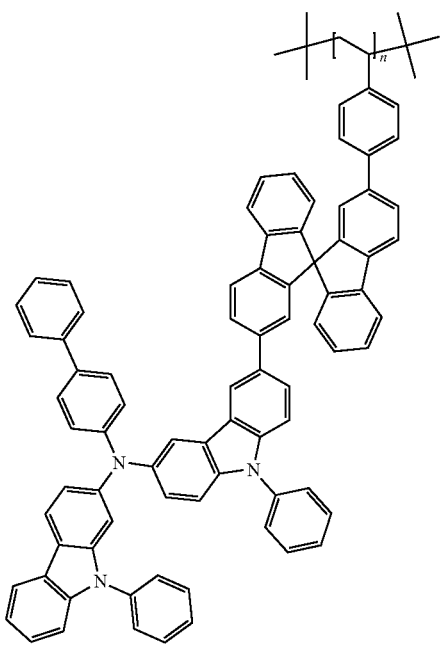
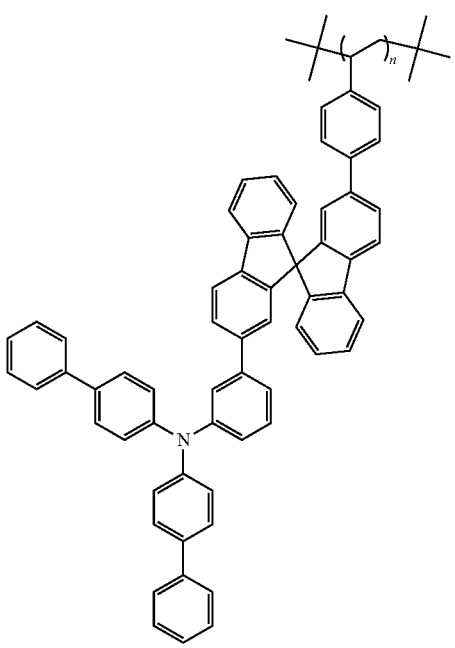

37
-continued
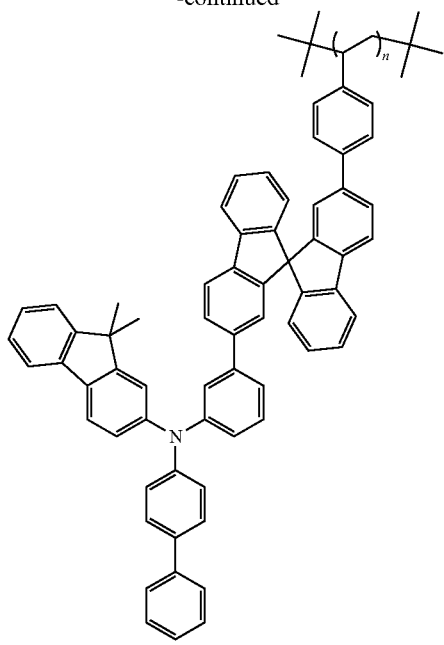
38
-continued
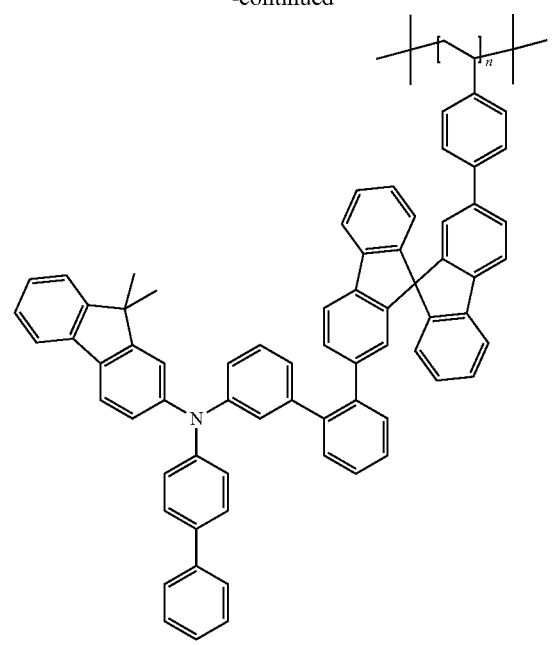
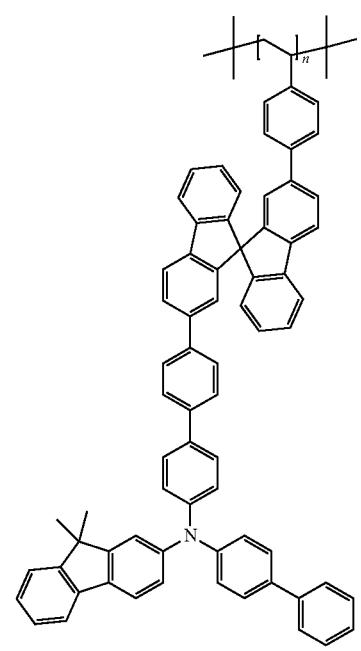
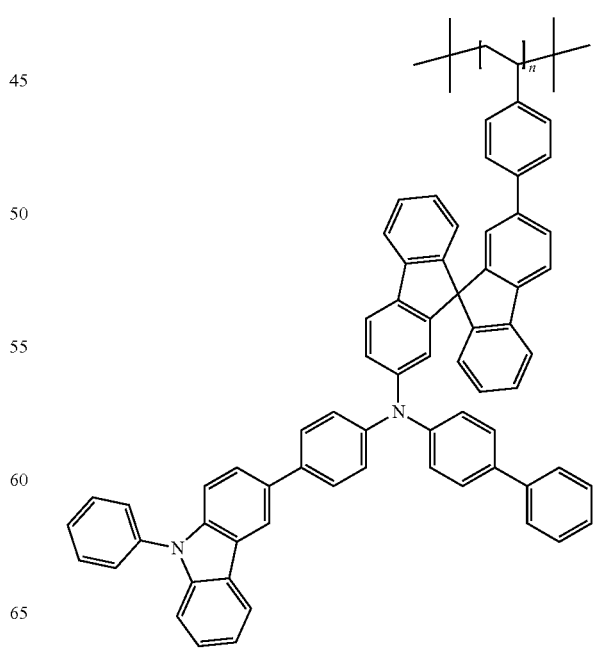

39
-continued
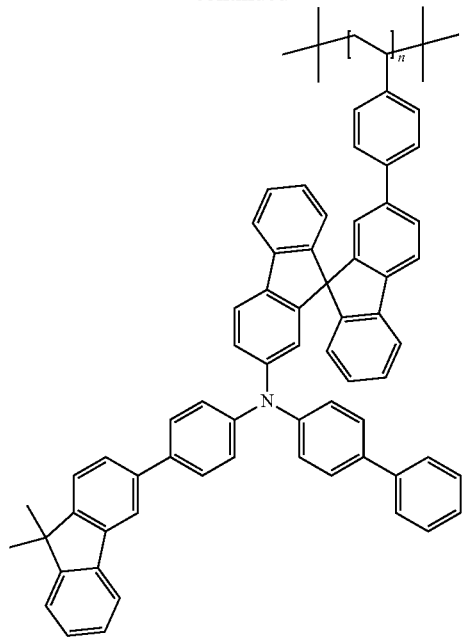
40
-continued
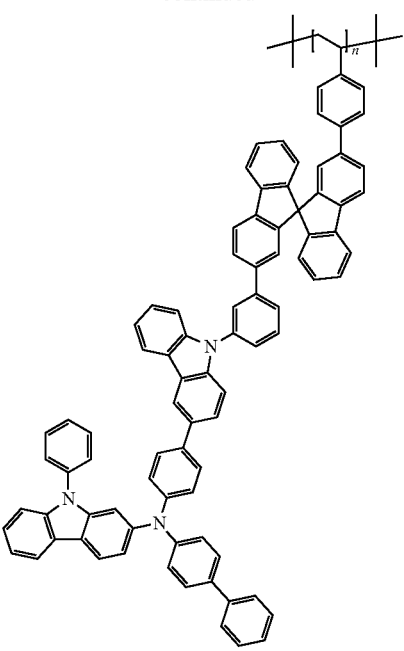
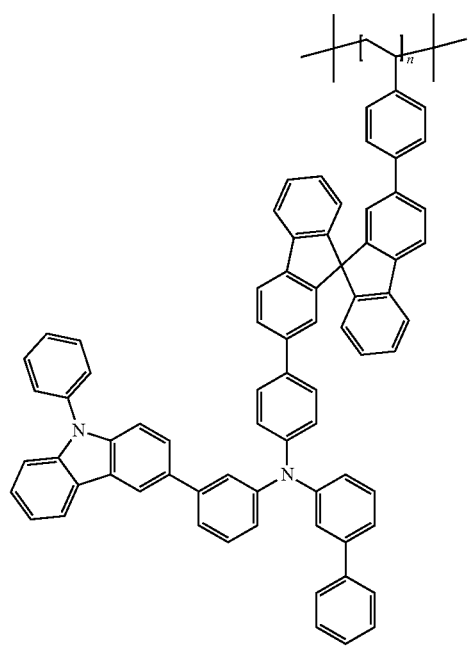
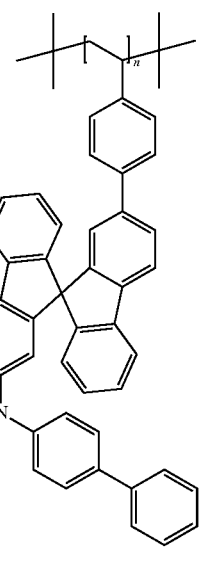

41
-continued
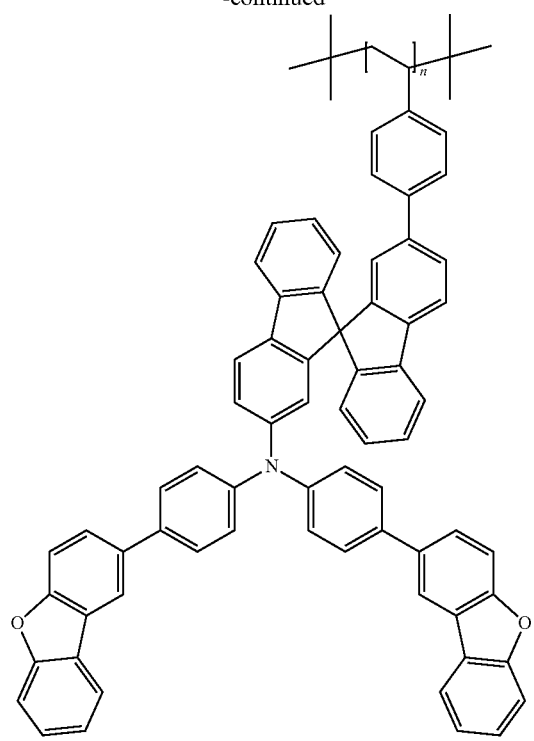
42
-continued
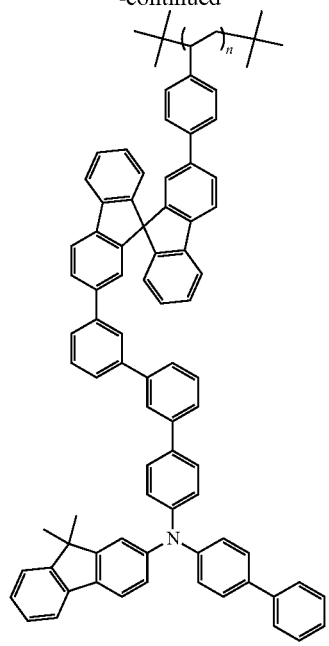
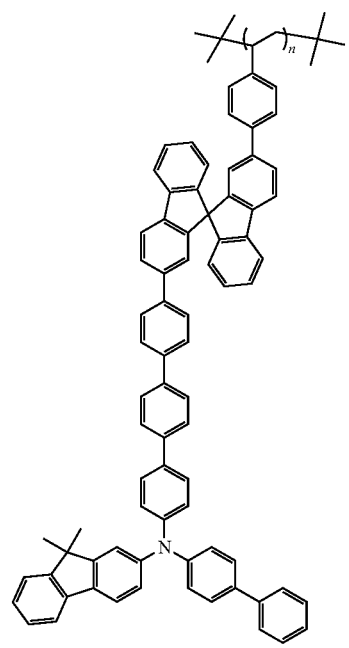
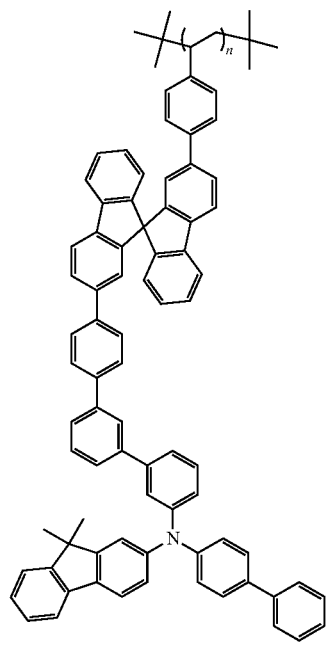

43
-continued
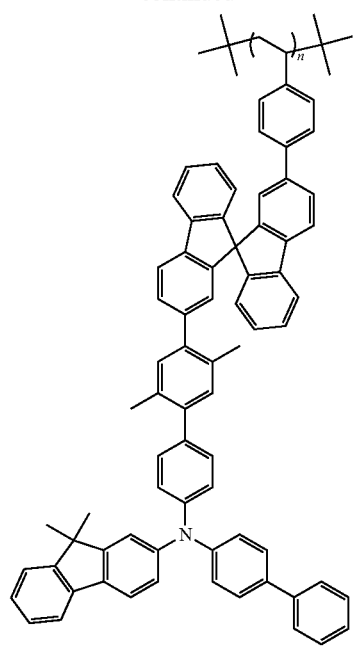
44
-continued
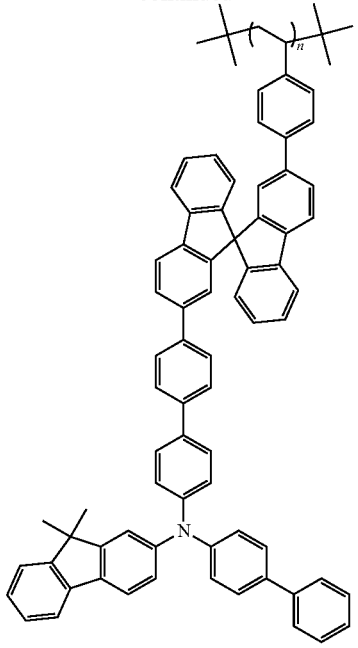
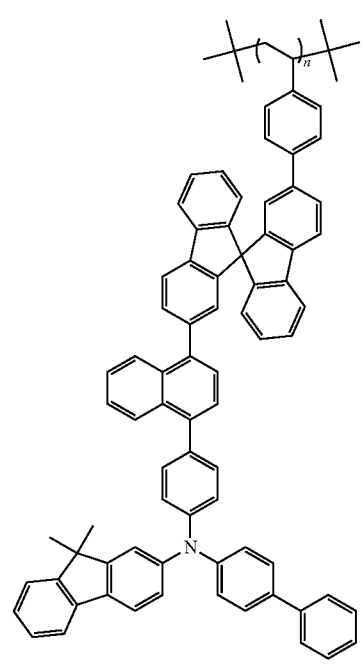
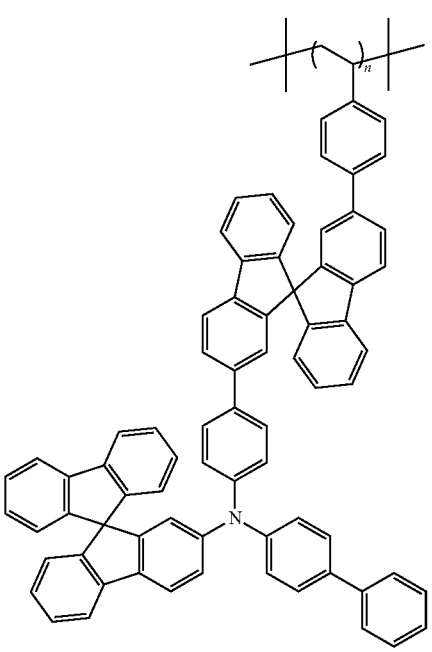

45
-continued
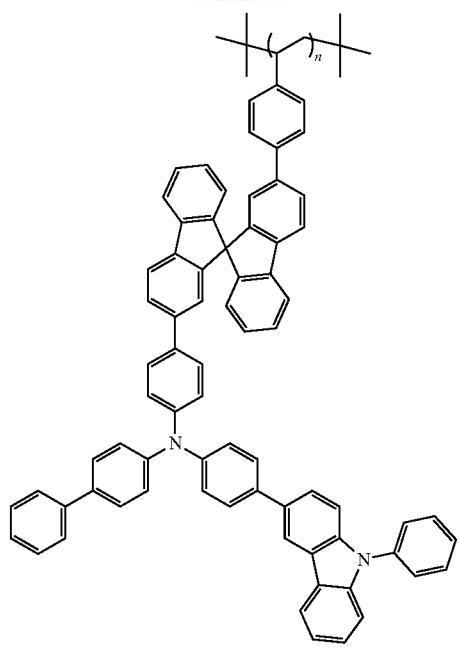
46
-continued
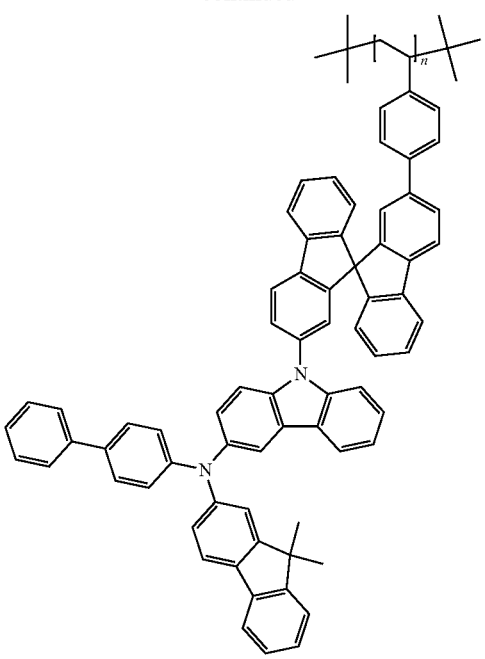
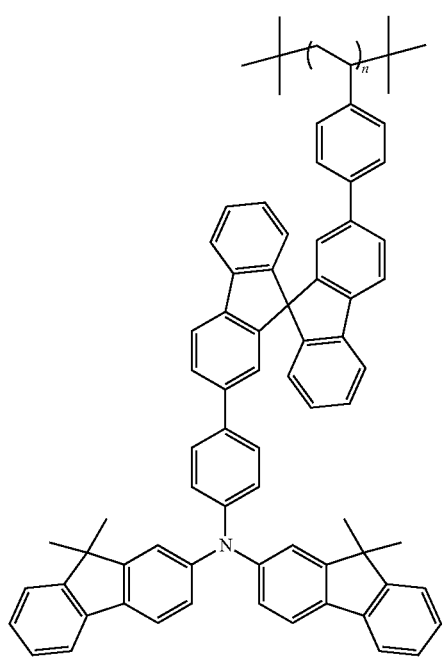
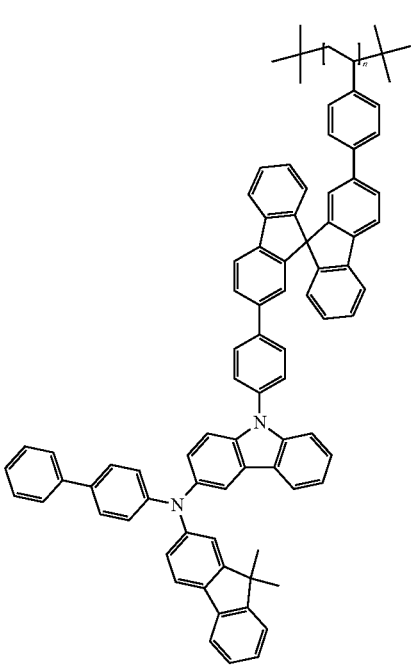

-continued

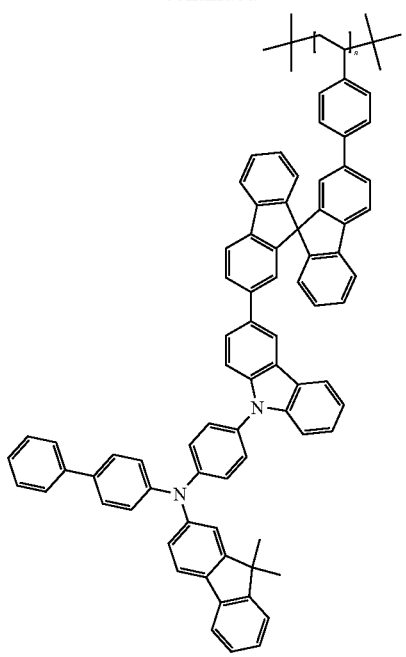

-continued

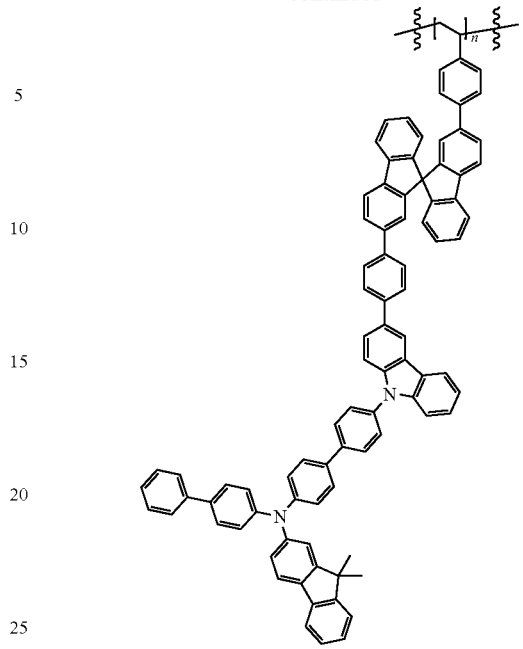

In the structures, n is, as a repetition number of the unit, an integer of 1 to 10,000.

In the present specification, the polymer including the unit represented by Chemical Formula 1 is a polymer formed with 100 mol % of the unit represented by Chemical Formula 1.

In the present specification, the polymer including the unit represented by Chemical Formula 1 is a polymer in which the unit represented by Chemical Formula 1 is arranged linearly.

In the present specification, an end group of the polymer may be hydrogen.

In one embodiment of the present specification, the polymer may have a number average molecular weight of 5,000 g/mol to 1,000,000 g/mol. Specifically, the number average molecular weight may be from 5,000 g/mol to 300,000 g/mol.

In one embodiment of the present specification, n is, as a repetition number, an integer of 4 to 200.

In one embodiment of the present specification, n is, as a repetition number, an integer of 4 to 150.

In one embodiment of the present specification, n is, as a repetition number, an integer of 4 to 100.

In one embodiment of the present specification, the polymer may have molecular weight distribution of 1 to 10. Preferably, the polymer has molecular weight distribution of 1 to 3.

The molecular weight measures a number average molecular weight (Mn) and a weight average molecular weight (Mw) using GPC with chlorobenzene as a solvent, and the molecular weight distribution means a number dividing the weight average molecular weight (Mw) by the number average molecular weight (Mn), that is, weight average molecular weight (Mw)/number average molecular weight (Mn).

Specifically, in the present specification, the molecular weight is analyzed using a GPC apparatus. As the column, PL mixed Bx2 is used, and as the solvent, tetrahydrofuran (THF) (filtered with 0.45 μm when used). A flow rate of 1.0

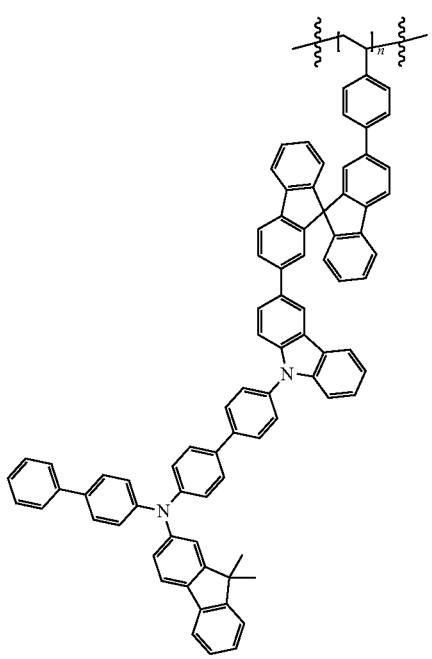

mL/min and a sample concentration of 1 mg/mL are used in the measurement. 100 μL of the sample is injected, and the column temperature is set at 40° C. As the detector, an Agilent RI detector is used, and the standard is set using polystyrene (PS). Data processing is conducted through the ChemStation program.

One embodiment of the present specification provides a coating composition including the polymer including the unit represented by Chemical Formula 1.

One embodiment of the present specification provides a coating composition including the monomer represented by Chemical Formula 2.

According to one embodiment of the present specification, the coating composition including the polymer including the unit represented by Chemical Formula 1 may further include a solvent.

According to one embodiment of the present specification, the coating composition including the monomer represented by Chemical Formula 2 may further include a solvent.

In one embodiment of the present specification, the coating composition including the polymer including the unit represented by Chemical Formula 1 may be a liquid phase. In one embodiment of the present specification, the coating composition including the monomer represented by Chemical Formula 2 may be a liquid phase. The "liquid phase" means in a liquid state at room temperature and atmospheric pressure.

In one embodiment of the present specification, examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone and cyclohexanone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; benzoate-based solvents such as methyl benzoate, butyl benzoate and 3-phenoxybenzoate; tetraline, and the like, however, the solvent is not limited thereto as long as it is a solvent capable of dissolving or dispersing the polymer or the monomer according to one embodiment of the present specification.

In another embodiment, the solvent may be used either alone as one type, or as a mixture mixing two or more solvent types.

In another embodiment, the solvent preferably has a boiling point of 40° C. to 250° C. and more preferably 60° C. to 230° C., however, the boiling point is not limited thereto.

In another embodiment, viscosity of the single or mixed solvent is preferably from 1 CP to 10 CP and more preferably from 3 CP to 8 CP, but is not limited thereto.

In another embodiment, the concentration of the coating composition including the polymer including the unit represented by Chemical Formula 1 and the concentration of the coating composition including the monomer represented by Chemical Formula 2 are the same as or different from each other, and each independently from 0.1 wt/v % to 20 wt/v %, and more preferably from 0.5 wt/v % to 5 wt/v %, but are not limited thereto.

In one embodiment of the present specification, the coating composition including the polymer including the unit represented by Chemical Formula 1; and the coating composition including the monomer represented by Chemical Formula 2 may each independently further include one, two or more types of additives selected from the group consisting of a thermal polymerization initiator and a photopolymerization initiator.

In one embodiment, the coating composition including the monomer represented by Chemical Formula 2 may further include a thermal polymerization initiator.

Examples of the thermal polymerization initiator may include peroxides such as methyl ethyl ketone peroxide, methyl isobutyl ketone peroxide, acetylacetone peroxide, methylcyclohexanone peroxide, cyclohexanone peroxide, isobutyryl peroxide, 2,4-dichlorobenzoyl peroxide, bis-3,5,5-trimethyl hexanoyl peroxide, lauryl peroxide, benzoyl peroxide, dicumyl peroxide, 2,5-dimethyl-2,5-(t-butyloxy)-hexane, 1,3-bis(t-butylperoxy-isopropyl)benzene, t-butyl cumyl peroxide, di-t-butyl peroxide, 2,5-dimethyl-2,5-(di-t-butylperoxy)hexane, tris-(t-butylperoxy)triazine, 1,1-di-t-butylperoxy-3,3,5-trimethylcyclohexane, 1,1-di-t-butylperoxycyclohexane, 2,2-di(t-butylperoxy)butane, 4,4-di-t-butylperoxy valeric acid n-butyl ester, 2,2-bis(4,4-t-butylperoxycyclohexyl)propane, t-butyl peroxyisobutyrate, di-t-butyl peroxyhexahydroterephthalate, t-butylperoxy-3,5,5-trimethylhexate, t-butyl peroxybenzoate and di-t-butyl peroxytrimethyl adipate; or azo-based such as azobis isobutylnitrile, azobis dimethylvaleronitrile and azobis cyclohexyl nitrile, but are not limited thereto.

Examples of the photopolymerization initiator may include acetophenone-based or ketal-based photopolymerization initiators such as diethoxyacetophenone, 2,2-dimethoxy-1,2-diphenyl ethan-1-one, 1-hydroxy-cyclohexyl-phenyl-ketone, 4-(2-hydroxyethoxy)phenyl-(2-hydroxy-2-propyl)ketone, 2-benzyl-2-dimethylamino-1-(4-morpholinophenyl)butanone-1,2-hydroxy-2-methyl-1-phenylpropan-1-one, 2-methyl-2-morpholino(4-methylthiophenyl)propan-1-one and 1-phenyl-1,2-propanedion-2-(o-ethoxycarbonyl)oxime; benzoin ether-based photopolymerization initiators such as benzoin, benzoin methyl ether, benzoin ethyl ether, benzoin isobutyl ether and benzoin isopropyl ether; benzophenone-based photopolymerization initiators such as benzophenone, 4-hydroxybenzophenone, 2-benzoylnaphthalene, 4-benzoylbiphenyl, 4-benzoyl phenyl ether, acrylated benzophenone and 1,4-benzoylbenzene; thioxanthone-based photopolymerization initiators such as 2-isopropylthioxanthone, 2-chlorothioxanthone, 2,4-dimethylthioxanthone, 2,4-diethylthioxanthone and 2,4-dichlorothioxanthone; and, as other photopolymerization initiators, ethyl anthraquinone, 2,4,6-trimethylbenzoyldiphenylphosphine oxide, 2,4,6-trimethylbenzoylphenylethoxyphosphine oxide, bis(2,4,6-trimethylbenzoyl)phenylphosphine oxide, bis(2,4-dimethoxybenzoyl)-2,4,4-trimethylpentylphosphine oxide, methylphenylglyoxyester, 9,10-phenanthrene, acridine-based compounds, triazine-based compounds, imidazole-based compounds, and the like, but are not limited thereto.

In addition, those having a photopolymerization facilitating effect may be used either alone or together with the photopolymerization initiator. Examples thereof may include triethanolamine, methyldiethanolamine, ethyl 4-dimethylaminobenzoate, isoamyl 4-dimethylaminobenzoate, (2-dimethylamino)ethyl benzoate, 4,4'-dimethylaminobenzophenone and the like, but are not limited thereto.

Another embodiment of the present specification provides an organic light emitting device formed using the coating composition.

One embodiment of the present specification provides an organic light emitting device including a first electrode; a second electrode provided opposite to the first electrode; and one or more organic material layers provided between the first electrode and the second electrode, wherein one or more layers of the organic material layers include the polymer including the unit represented by Chemical Formula 1 described above.

The organic light emitting device in one embodiment of the present specification includes a first electrode; a second electrode provided opposite to the first electrode; and one or more organic material layers provided between the first electrode and the second electrode, and one or more layers of the organic material layers are formed using the coating composition including the polymer including the unit represented by Chemical Formula 1.

Another embodiment of the present specification provides an organic light emitting device including a first electrode; a second electrode provided opposite to the first electrode; and one or more organic material layers provided between the first electrode and the second electrode, wherein one or more layers of the organic material layers include a cured material of the coating composition including the monomer represented by Chemical Formula 2 described above.

In one embodiment, the cured material of the coating composition including the monomer represented by Chemical Formula 2 may be in a cured state by heat treating or light treating the coating composition.

In one embodiment of the present specification, the first electrode is a cathode, and the second electrode is an anode.

In another embodiment, the first electrode is an anode, and the second electrode is a cathode.

In one embodiment of the present specification, the first electrode is an anode, the second electrode is a cathode, the one or more organic material layers include a light emitting layer, and the organic material layer including the polymer including the unit represented by Chemical Formula 1 is provided between the anode and the light emitting layer.

In one embodiment of the present specification, the organic material layer including the polymer including the unit represented by Chemical Formula 1 is a hole transfer layer, a hole injection layer, or a layer carrying out hole transfer and hole injection at the same time.

In one embodiment of the present specification, the organic material layer including the polymer including the unit represented by Chemical Formula 1 is a hole transfer layer.

In one embodiment of the present specification, the organic material layer including the polymer including the unit represented by Chemical Formula 1 is a hole injection layer.

In one embodiment of the present specification, the organic material layer including the polymer including the unit represented by Chemical Formula 1 is a layer carrying out hole transfer and hole injection at the same time.

In another embodiment of the present specification, the organic material layer including a cured material of the coating composition including the monomer represented by Chemical Formula 2 is a hole transfer layer, a hole injection layer, or a layer carrying out hole transfer and hole injection at the same time.

In one embodiment of the present specification, the organic material layer including a cured material of the coating composition including the monomer represented by Chemical Formula 2 is a hole transfer layer.

In one embodiment of the present specification, the organic material layer including a cured material of the coating composition including the monomer represented by Chemical Formula 2 is a hole injection layer.

In one embodiment of the present specification, the organic material layer including a cured material of the coating composition including the monomer represented by Chemical Formula 2 is a layer carrying out hole transfer and hole injection at the same time.

In one embodiment of the present specification, the coating composition including the polymer including the unit represented by Chemical Formula 1; and the coating composition including the monomer represented by Chemical Formula 2 may each independently further include a p-doping material.

In one embodiment of the present specification, the p-doping material includes at least one selected from the group consisting of $F_4TCNQ$; and a boron anion.

In one embodiment of the present specification, the boron anion includes a halogen group.

In one embodiment of the present specification, the boron anion includes F.

In one embodiment of the present specification, the p-doping material is one, two or more types selected from among the following structural formulae.

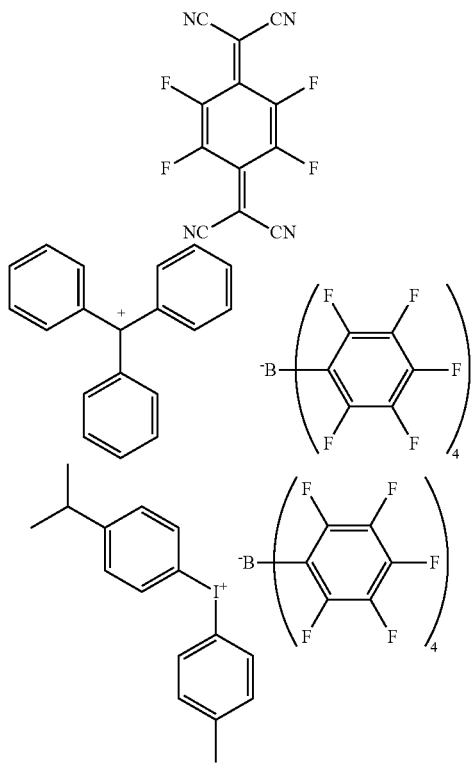

In one embodiment of the present specification, when the coating composition including the polymer including the unit represented by Chemical Formula 1 includes the p-doping material, the polymer including the unit represented by Chemical Formula 1 and the p-doping material are included in the coating composition in a weight ratio of 99:1 to 70:30, and preferably in a weight ratio of 90:10 to 70:30.

In one embodiment of the present specification, when the coating composition including the monomer represented by Chemical Formula 2 includes the p-doping material, the monomer represented by Chemical Formula 2 and the p-doping material are included in the coating composition in a weight ratio of 99:1 to 70:30, and preferably in a weight ratio of 90:10 to 70:30.

In one embodiment of the present specification, the organic light emitting device may further include one, two or more layers selected from the group consisting of a hole injection layer, a hole transfer layer, a light emitting layer, an electron transfer layer, an electron injection layer, an electron blocking layer and a hole blocking layer.

In another embodiment, the organic light emitting device may be an organic light emitting device having a structure in a normal direction in which an anode, one or more organic material layers and a cathode are consecutively laminated on a substrate (normal type).

In another embodiment, the organic light emitting device may be an organic light emitting device having a structure in a reverse direction in which a cathode, one or more organic material layers and an anode are consecutively laminated on a substrate (inverted type).

The organic material layer of the organic light emitting device of the present specification may be formed in a single layer structure, but may also be formed in a multilayer structure in which two or more organic material layers are laminated. For example, the organic light emitting device of the present specification may have a structure including a hole injection layer, a hole transfer layer, a light emitting layer, an electron transfer layer, an electron injection layer and the like as the organic material layer. However, the structure of the organic light emitting device is not limited thereto, and may include a smaller or lager number of organic material layers.

For example, a structure of the organic light emitting device according to one embodiment of the present specification is illustrated in FIG. 1.

FIG. 1 illustrates a structure of the organic light emitting device in which a first electrode (201), a hole injection layer (301), a hole transfer layer (401), a light emitting layer (501), an electron transfer layer (601) and a second electrode (701) are consecutively laminated on a substrate (101). In one embodiment, a layer carrying out electron injection and transfer at the same time may be provided instead of the electron transfer layer (601).

In one embodiment of the present specification, the hole injection layer (301), the hole transfer layer (401) or the light emitting layer (501) of FIG. 1 may be formed using the coating composition including the polymer including the unit represented by Chemical Formula 1.

In one embodiment of the present specification, the hole injection layer (301) of FIG. 1 may be formed using the coating composition including the polymer including the unit represented by Chemical Formula 1.

In one embodiment of the present specification, the hole transfer layer (401) of FIG. 1 may be formed using the coating composition including the polymer including the unit represented by Chemical Formula 1.

FIG. 1 illustrates the organic light emitting device, however, the organic light emitting device is not limited thereto.

When the organic light emitting device includes a plurality of organic material layers, the organic material layers may be formed with materials that are the same as or different from each other.

The organic light emitting device of the present specification may be manufactured using materials and methods known in the art, except that one or more layers of the organic material layers are formed using the coating composition according to one embodiment of the present disclosure.

For example, the organic light emitting device of the present specification may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

Another embodiment of the present specification provides a method for manufacturing an organic light emitting device formed using the coating composition. Herein, the coating composition means the coating composition including the polymer including the unit represented by Chemical Formula 1; or the coating composition including the monomer represented by Chemical Formula 2.

Specifically, one embodiment of the present specification provides a method for manufacturing an organic light emitting device, the method including preparing a first electrode; forming one or more organic material layers on the first electrode; and forming a second electrode on the organic material layer, wherein the forming of one or more organic material layers includes forming an organic material layer using the coating composition including the polymer including the unit represented by Chemical Formula 1 described above or the coating composition including the monomer represented by Chemical Formula 2 described above, and the forming of an organic material layer using the coating composition includes coating the coating composition on the first electrode; and heat treating or light treating the coated coating composition. In one embodiment of the present specification, the organic material layer formed using the coating composition is formed using spin coating or inkjetting.

In another embodiment, the organic material layer formed using the coating composition is formed using a printing method.

In an embodiment of the present specification, examples of the printing method include inkjet printing, nozzle printing, offset printing, transfer printing, screen printing or the like, but are not limited thereto.

The coating composition according to one embodiment of the present specification is suited for a solution process due to its structural properties and may be formed using a printing method, and therefore, is economically effective in terms of time and costs when manufacturing a device.

In one embodiment of the present specification, the forming of an organic material layer using the coating composition includes coating the coating composition on the first electrode; and heat treating or light treating the coated coating composition.

In one embodiment of the present specification, in the heat treating or light treating, the time of the heat treating is preferably within 1 hour and more preferably within 30 minutes.

In one embodiment of the present specification, in the heat treating or light treating, the atmosphere of the heat treating is preferably inert gas such as argon or nitrogen.

In one embodiment, when using the coating composition including the polymer including the unit represented by Chemical Formula 1 as the coating composition, the heat treating or light treating of the coated coating composition may be removing a solvent from the coated coating composition.

In one embodiment, when using the coating composition including the monomer represented by Chemical Formula 2 as the coating composition, the heat treating or light treating of the coated coating composition may be removing a solvent while an alkenyl group of the monomer represented by Chemical Formula 2 participates in the polymerization and forms the polymer including the unit represented by Chemical Formula 1.

When including the heat treating or light treating in the forming of an organic material layer using the coating composition, an organic material layer including a structure in which the coating composition becomes a thin film may be provided. In this case, being dissolved by a solvent deposited on a surface of the organic material layer formed using the coating composition, or being morphologically influenced or decomposed may be prevented.

Accordingly, the organic material layer formed using the coating composition has resistance for a specific solvent, and a multilayer may be formed by repeatedly performing a solution deposition method using the specific solvent. In this case, lifetime properties of a device may also be enhanced due to increased stability of the organic material layer.

In one embodiment of the present specification, the coating composition including the polymer may use a coating composition mixed to a polymer binder and dispersed.

In one embodiment of the present specification, as the polymer binder, those that do not extremely inhibit charge transfer are preferred, and those that do not have strong absorption for visible light are preferably used. Examples of the polymer binder may include poly(N-vinylcarbazole), polyaniline and derivatives thereof, polythiophene and derivatives thereof, poly(p-phenylenevinylene) and derivatives thereof, poly(2,5-thienylenevinylene) and derivatives thereof, polycarbonate, polyacrylate, polymethyl acrylate, polymethyl methacrylate, polystyrene, polyvinyl chloride, polysiloxane and the like.

In addition, the organic material layer according to one embodiment of the present specification may include the polymer including the unit represented by Chemical Formula 1 alone, but may also further include other monomers or other polymers.

As the anode material, materials having large work function are normally preferred so that hole injection to an organic material layer is smooth. Specific examples of the anode material capable of being used in the present specification include metals such as vanadium, chromium, copper, zinc and gold, and alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as $LiF/Al$ or $LiO_2/Al$, and the like, but are not limited thereto.

The hole injection layer is a layer that injects holes from an electrode, and the hole injection material is preferably a compound that has an ability to transfer holes and thereby has a hole injection effect in an anode and an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and, when the organic light emitting device includes an additional hole transfer layer in addition to the hole transfer layer including the polymer including the unit represented by Chemical Formula 1, materials capable of receiving holes from an anode or a hole injection layer, moving the holes to a light emitting layer, and having high mobility for the holes are suited as the hole transfer material. Specific examples thereof include arylamine-based organic materials, conductive polymers, block copolymers having conjugated parts and non-conjugated parts together, and the like, but are not limited thereto.

The electron blocking layer is a layer capable of enhancing device lifetime and efficiency by preventing electrons injected from an electron injection layer from entering a hole injection layer after passing through a light emitting layer, and as necessary, may be formed in a proper part between the light emitting layer and the hole injection layer using known materials.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, or the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and compounds in which one, two or more substituents selected from the group consisting of an aryl group, a silyl group, an alkyl group, a cycloalkyl group and an arylamine group are substituted or unsubstituted may be used. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including Alq$_3$; organic radical compounds; hydroxyflavon-metal complexes, or the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition thereto, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and generally, may be formed under the same condition as the hole injection layer. Specifically, oxadiazole derivatives or triazole derivatives, phenanthroline derivatives, aluminum complexes and the like are included, however, the material is not limited thereto.

The organic light emitting device according to the present specification may be a top-emission type, a bottom-emission type or a dual-emission type depending on the materials used.

MODE FOR INVENTION

Hereinafter, the present specification will be described in detail with reference to examples in order to specifically describe the present specification. However, the examples according to the present specification may be modified to various different forms, and the scope of the present specification is not to be construed as being limited to the examples described below. Examples of the present specification are provided in order to more fully describe the present specification to those having average knowledge in the art.

Synthesis of Monomer 1

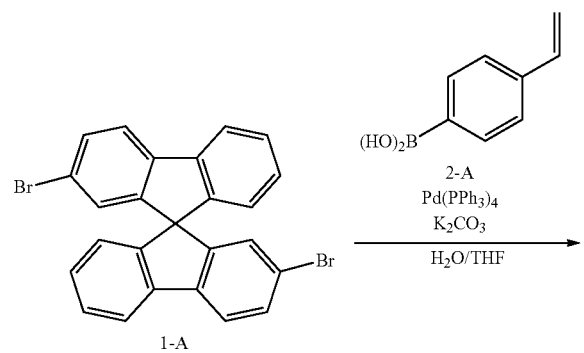

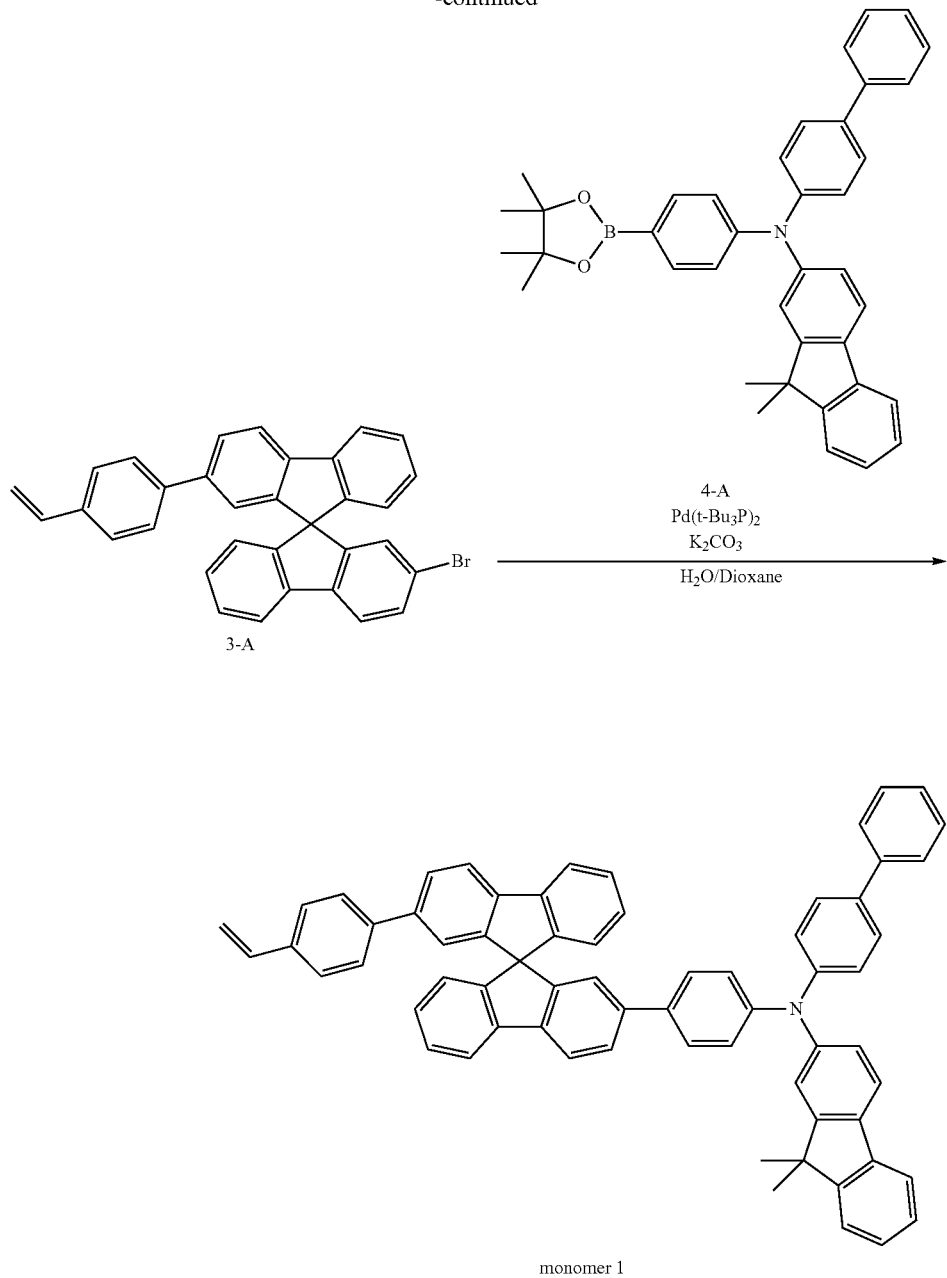

monomer 1

1) Synthesis of Compound 3-A

Compound 1-A (50 g, 105.4 mmol, 1 eq.) and Compound 2-A (31.2 g, 211 mmol, 2 eq.) were dissolved in tetrahydrofuran (THF) (300 g), and stirred for 10 minutes in a 80° C. bath. $K_2CO_3$ (37.89 g, 274 mmol, 2.6 eq.) dissolved in water (300 mL) was added dropwise thereto for 10 minutes. A Pd catalyst (3.66 g, 3.2 mmol, 0.03 eq.) was introduced thereto under reflux. The result was stirred for 2 hours, and then washed with ethyl acetate (EA)/$H_2O$ to separate the organic layer, and the solvent was vacuum dried. The result was purified using column chromatography through n-hexane (n-Hex) and ethyl acetate (EA), and then recrystallized with tetrahydrofuran (THF) and ethanol to obtain white solid Compound 3-A.

2) Synthesis of Monomer 1 Compound 3-A (2.4 g, 5 mmol, 1 eq.) and Compound 4-A (2.82 g, 5 mmol, 1 eq.) were dissolved in 1,4-dioxane (20 ml), and stirred for 30 minutes in a 120° C. bath. $K_2CO_3$ (5.1 g, 37 mmol, 1.75 eq.) dissolved in water (40 mL) was added dropwise thereto for 10 minutes while maintaining an inner temperature of the solution at 90° C. A Pd catalyst (0.077 g, 0.15 mmol, 0.03 eq.) was introduced thereto under reflux. The result was stirred for 1 hour, and then washed with ethyl acetate (EA)/$H_2O$ to separate the organic layer, and the solvent was vacuum dried. The result was purified using column chromatography through n-hexane (n-Hex) and dichloromethane (DCM), and then recrystallized with n-hexane (n-Hex) to obtain Monomer 1 (3.58 g).

MS: $[M+H]^+$=853

Synthesis of Monomer 2
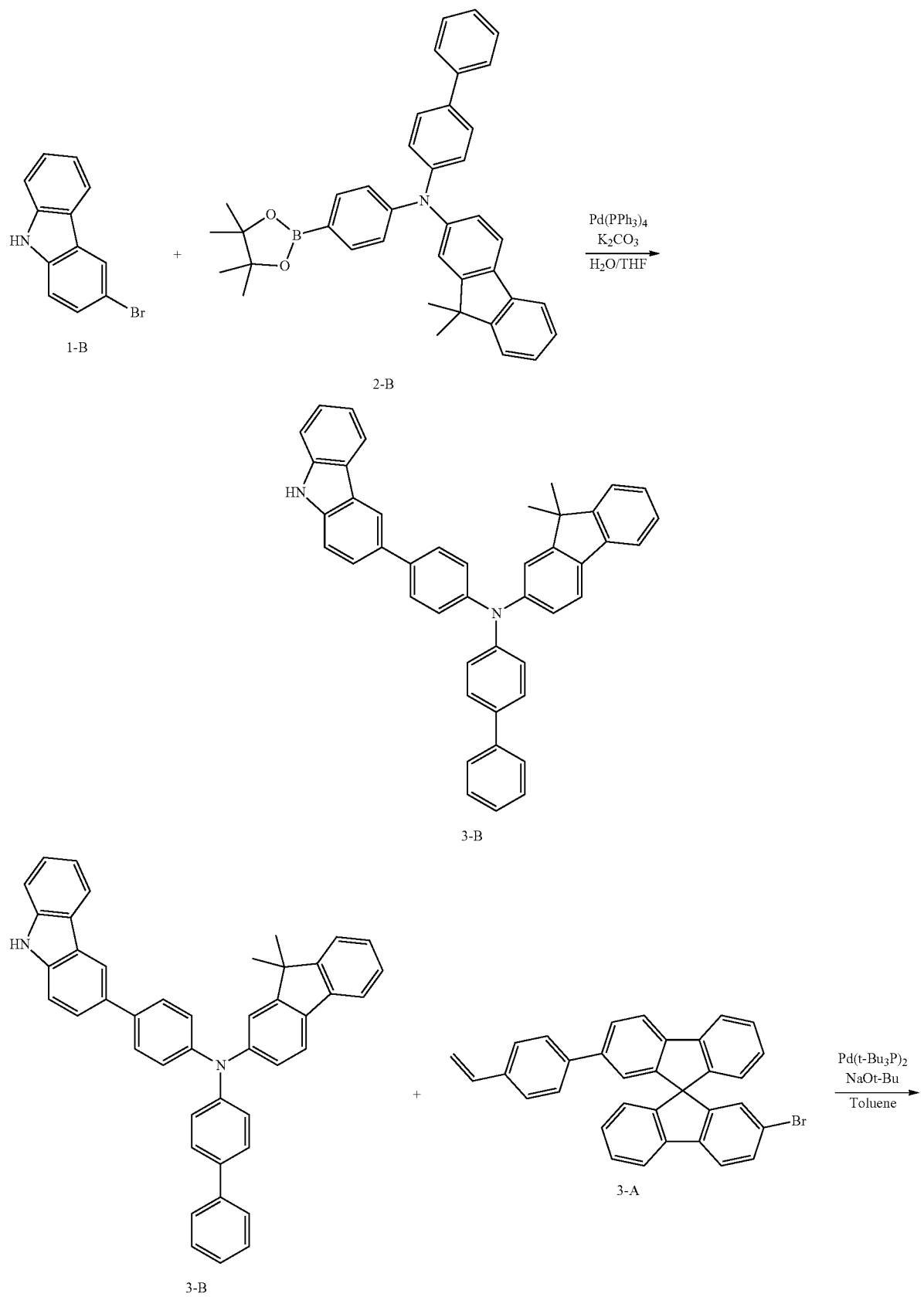 [SMILES: Brc1ccc2[nH]c3ccccc3c2c1 ; CC1(C)c2ccccc2-c2ccc(N(c3ccc(B4OC(C)(C)C(C)(C)O4)cc3)c3ccc(-c4ccccc4)cc3)cc21 ; CC1(C)c2ccccc2-c2ccc(N(c3ccc(-c4ccccc4)cc3)c3ccc(-c4ccc5[nH]c6ccccc6c5c4)cc3)cc21 ; CC1(C)c2ccccc2-c2ccc(N(c3ccc(-c4ccccc4)cc3)c3ccc(-c4ccc5[nH]c6ccccc6c5c4)cc3)cc21 ; C=Cc1ccc(-c2ccc3c(c2)C2(c4ccccc4-c4ccc(Br)cc42)c2ccccc2-3)cc1]

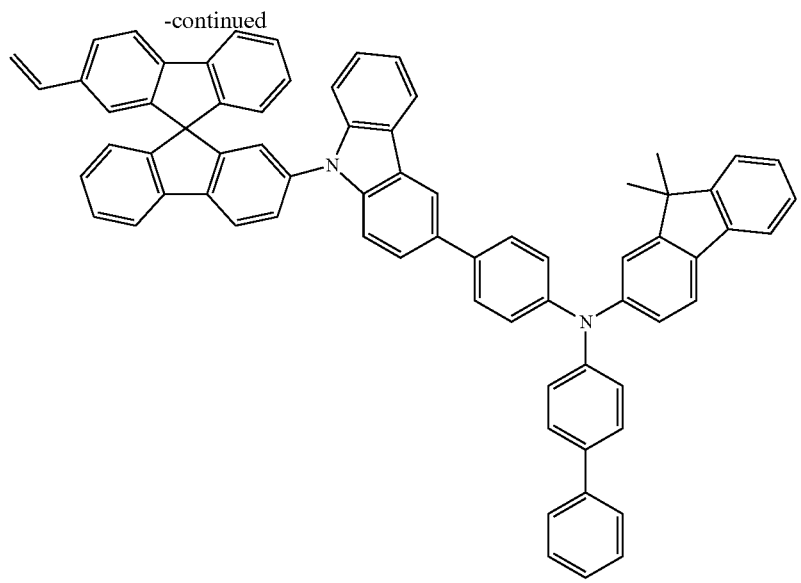

monomer 2

1) Synthesis of Compound 3-B

Compound 1-B (15 g, 60.95 mmol, 1.0 eq.) and Compound 2-B (36.06 g, 64 mmol, 1.05 eq.) were dissolved in tetrahydrofuran (THF) (200 mL), and stirred for 10 minutes in a 80° C. bath. $K_2CO_3$ (10.95 g, 79 mmol, 1.3 eq.) dissolved in water (87 mL) was added dropwise thereto for 10 minutes. A Pd catalyst (2.11 g, 1.8 mmol, 0.03 eq.) was introduced thereto under reflux. The result was stirred for 12 hours, and then washed with ethyl acetate (EA)/$H_2O$ to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain Compound 3-B.

2) Synthesis of Monomer 2

Compound 3-A (3 g, 6 mmol, 1 eq.) and Compound 3-B (4 g, 7 mmol, 1.1 eq.) were dissolved in anhydrous toluene (15 g), and stirred for 10 minutes in a 130° C. bath. Sodium tert-butoxide (NaOt-Bu) (1.45 g, 15 mmol, 2.5 eq.) was introduced thereto. A Pd catalyst (0.077 g, 0.15 mmol, 0.03 eq.) was introduced thereto under reflux. The result was stirred for 1 hour, and then washed with ethyl acetate (EA)/$H_2O$ to separate the organic layer, and the solvent was vacuum dried. The result was purified using column chromatography through n-hexane (n-Hex) and dichloromethane (DCM), and then recrystallized with n-hexane (n-Hex) to obtain white solid Monomer 2 (1.84 g).

MS: $[M+H]^+$=1018

Synthesis of Monomer 3

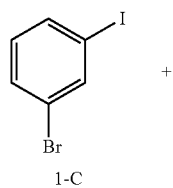

1-C

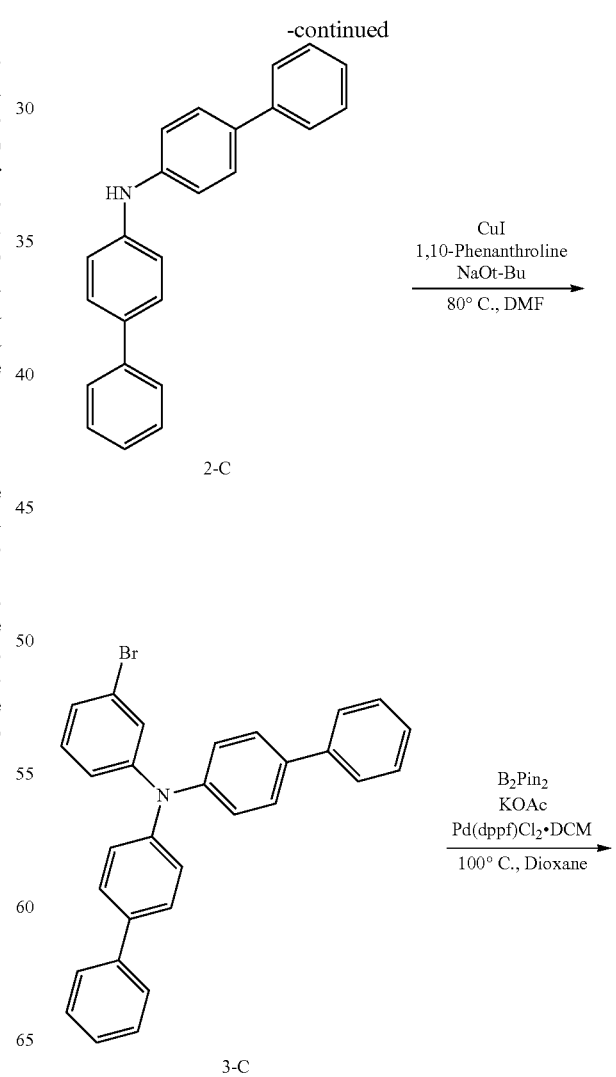

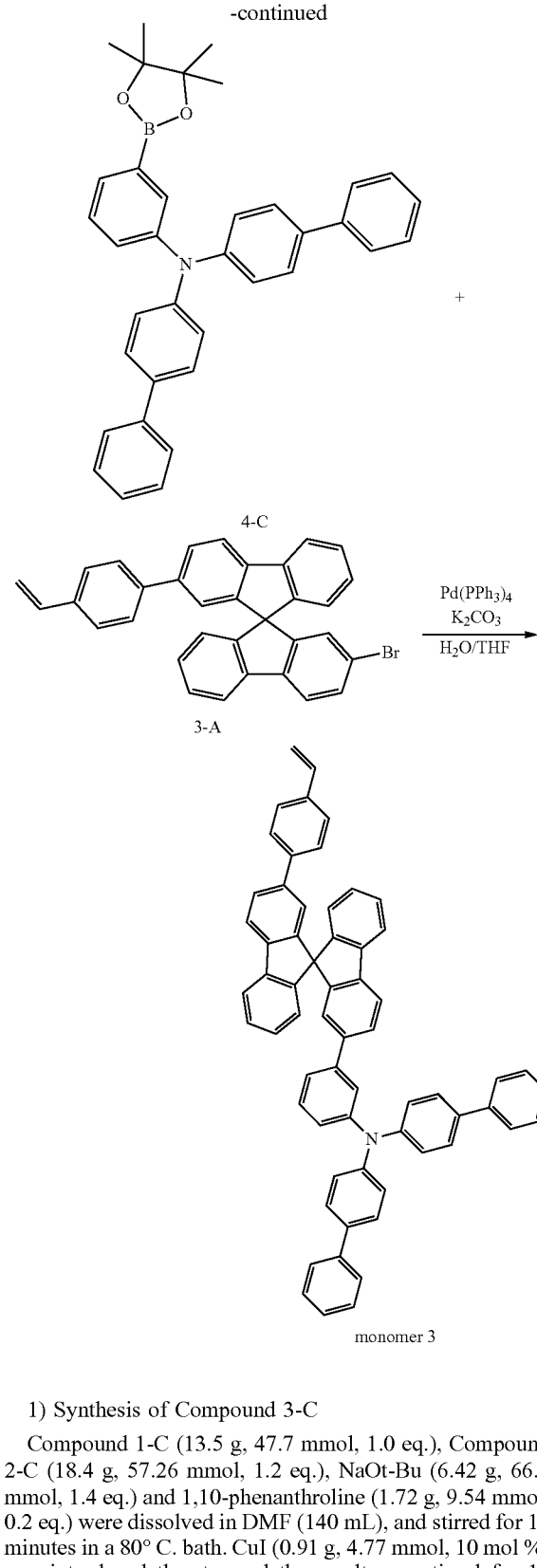

monomer 3

1) Synthesis of Compound 3-C

Compound 1-C (13.5 g, 47.7 mmol, 1.0 eq.), Compound 2-C (18.4 g, 57.26 mmol, 1.2 eq.), NaOt-Bu (6.42 g, 66.8 mmol, 1.4 eq.) and 1,10-phenanthroline (1.72 g, 9.54 mmol, 0.2 eq.) were dissolved in DMF (140 mL), and stirred for 10 minutes in a 80° C. bath. CuI (0.91 g, 4.77 mmol, 10 mol %) was introduced thereto, and the result was stirred for 12 hours. The result was washed with ethyl acetate (EA)/H$_2$O to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain Compound 3-C.

2) Synthesis of Compound 4-C

Compound 3-C (10 g, 21 mmol, 1.0 eq.) and B$_2$Pin$_2$ (13.3 g, 52.4 mmol, 2.5 eq.) were dissolved in 1,4-dioxane (300 mL), and stirred for 10 minutes in a 80° C. bath. KOAc (8.86 g, 90.3 mmol, 4.3 eq.) and Pd(dppf)Cl$_2$-DCM (1.38 g, 1.89 mmol, 0.09 eq.) were introduced thereto. The result was stirred for 12 hours in a 110° C. bath, and then washed with ethyl acetate (EA)/H$_2$O to separate the organic layer, and the solvent was vacuum dried.

The result was purified using medium pressure liquid chromatography (MPLC) through n-hexane (n-Hex) and dichloromethane (DCM), and then recrystallized with n-hexane (n-Hex) to obtain Compound 4-C.

3) Synthesis of Monomer 3

Compound 4-C (31.8 g, 60.74 mmol, 1.0 eq.) and Compound 3-A (33.24 g, 66.8 mmol, 1.1 eq.) were dissolved in tetrahydrofuran (THF) (300 mL), and stirred for 10 minutes in a 80° C. bath. K$_2$CO$_3$ (10.95 g, 79 mmol, 1.3 eq.) dissolved in water (90 mL) was added dropwise thereto for 10 minutes. A Pd catalyst (2.11 g, 1.8 mmol, 0.03 eq.) was introduced thereto under reflux. The result was stirred for 12 hours, and then washed with ethyl acetate (EA)/H$_2$O to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain white solid Monomer 3 (44.5 g).

MS: [M+H]$^+$=813

Synthesis of Monomer 4

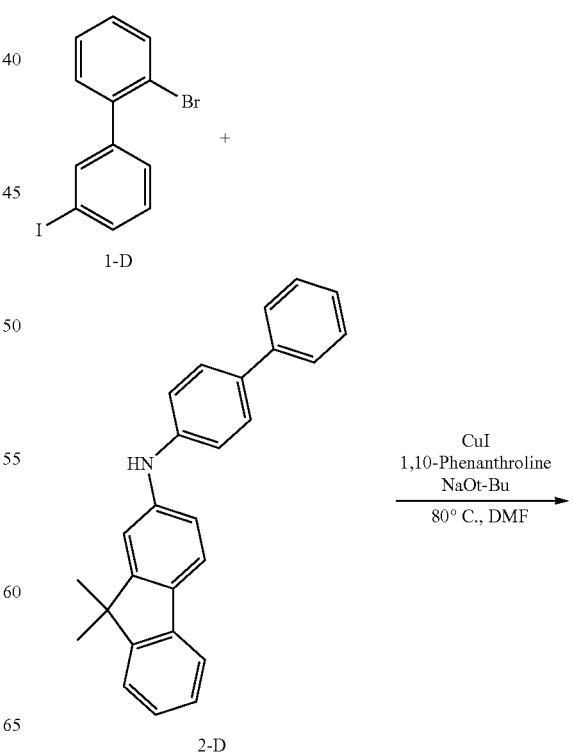

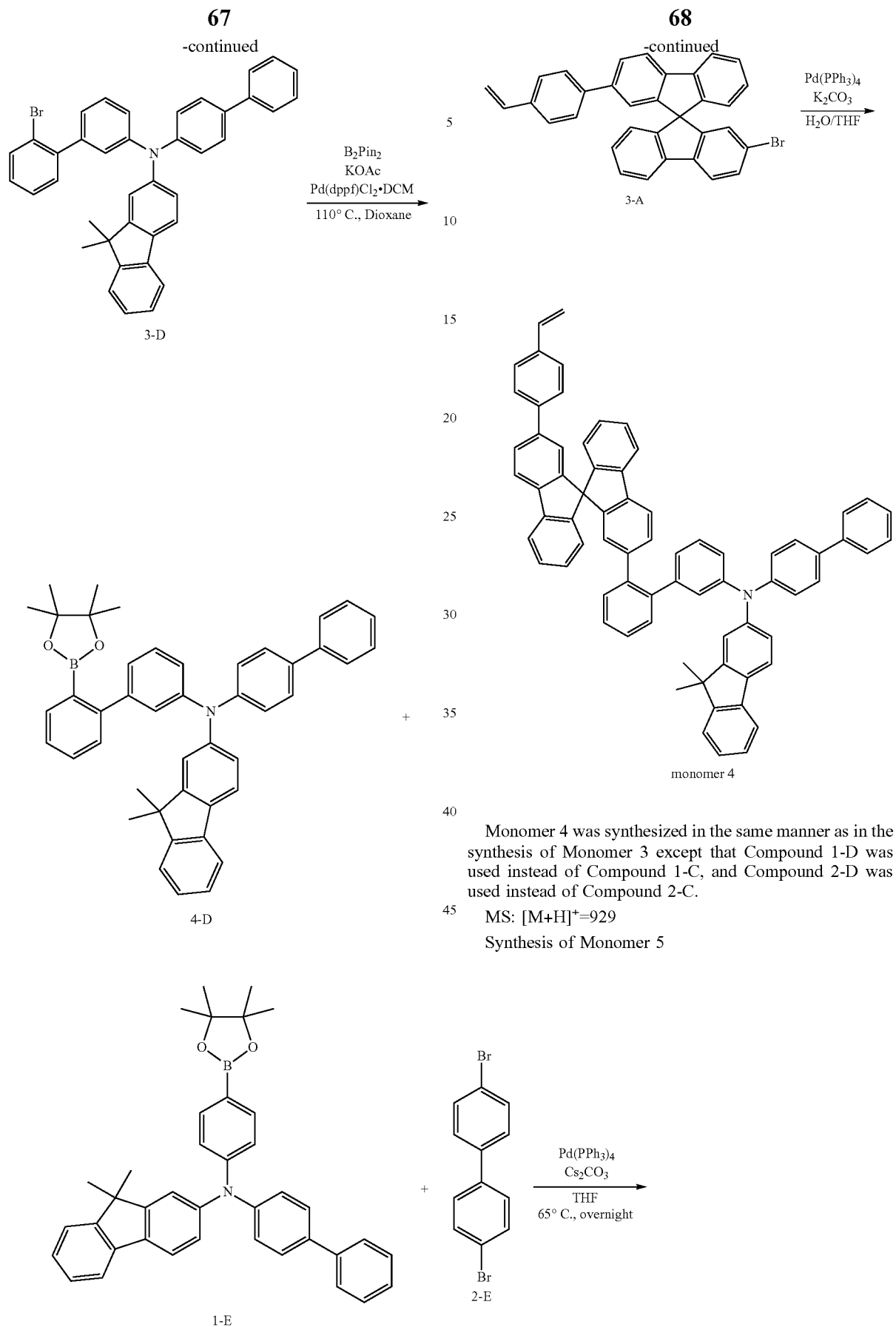
Monomer 4 was synthesized in the same manner as in the synthesis of Monomer 3 except that Compound 1-D was used instead of Compound 1-C, and Compound 2-D was used instead of Compound 2-C.
MS: $[M+H]^+=929$
Synthesis of Monomer 5

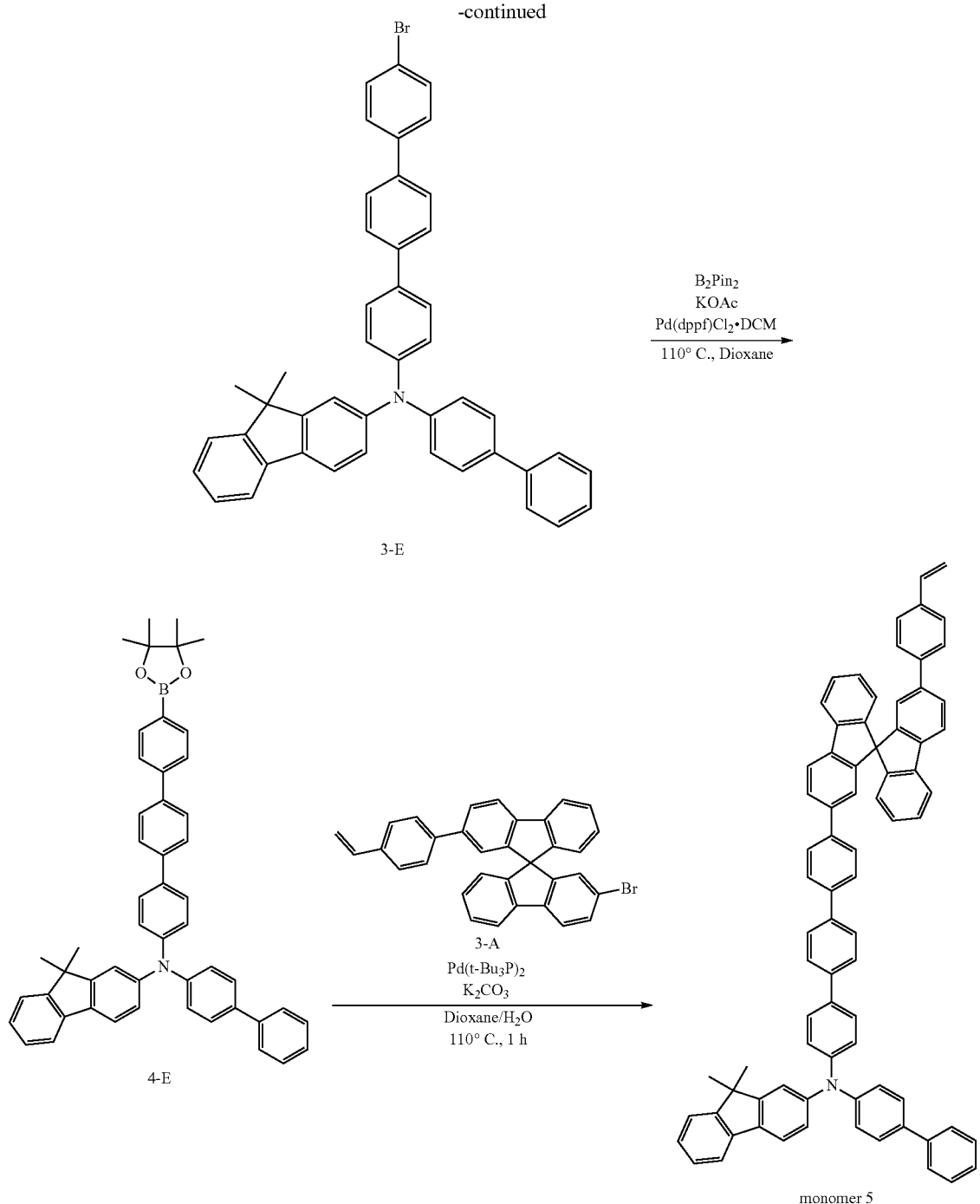

1) Synthesis of Compound 3-E Compound 1-E (15.01 g, 26.6 mmol, 1.0 eq.) and Compound 2-E (13.3 g, 42.6 mmol, 1.6 eq.) were dissolved in tetrahydrofuran (THF) (150 mL), and stirred for 10 minutes in a 80° C. bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. bath, and then washed with ethyl acetate (EA)/$H_2O$ to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain Compound 3-E.

2) Synthesis of Compound 4-E

Compound 3-E (10 g, 14.95 mmol, 1.0 eq.) and $B_2Pin_2$ (9.49 g, 37.4 mmol, 2.5 eq.) were dissolved in 1,4-dioxane (100 mL), and stirred for 10 minutes in a 80° C. bath. KOAc (6.21 g, 64.28 mmol, 4.3 eq.) and $Pd(dppf)Cl_2DCM$ (0.98 g, 1.35 mmol, 0.09 eq.) were introduced thereto. The result was stirred for 12 hours in a 110° C. bath, and then washed with ethyl acetate (EA)/$H_2O$ to separate the organic layer, and the solvent was vacuum dried. The result was purified using medium pressure liquid chromatography (MPLC) through n-hexane (n-Hex) and dichloromethane (DCM), and then recrystallized with n-hexane (n-Hex) to obtain Compound 4-E.

3) Synthesis of Monomer 5

Compound 4-E (43.5 g, 60.74 mmol, 1.0 eq.) and Compound 3-A (33.24 g, 66.8 mmol, 1.1 eq.) were dissolved in tetrahydrofuran (THF) (300 mL), and stirred for 10 minutes in a 80° C. bath. $K_2CO_3$ (10.95 g, 79 mmol, 1.3 eq.) dissolved in water (90 mL) was added dropwise thereto for 10 minutes. A Pd catalyst (2.11 g, 1.8 mmol, 0.03 eq.) was introduced thereto under reflux. The result was stirred for 12 hours in a 110° C. bath, and then washed with ethyl acetate (EA)/$H_2O$ to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain white solid Monomer 5 (55 g).

MS: $[M+H]^+=1005$

Synthesis of Monomer 6

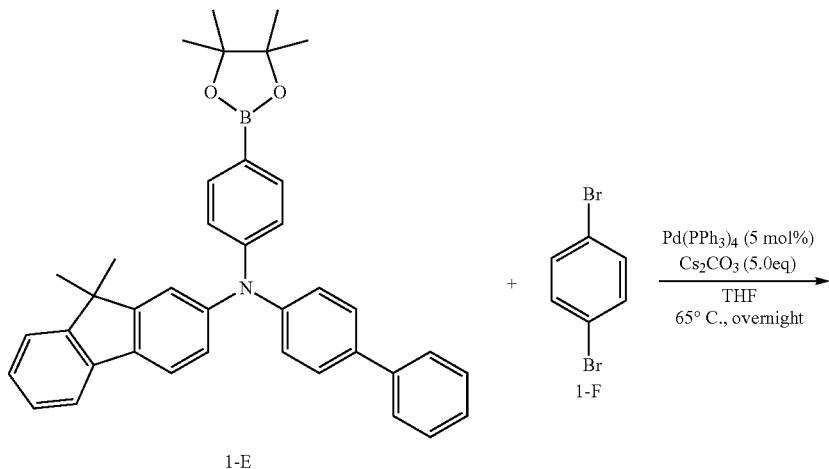

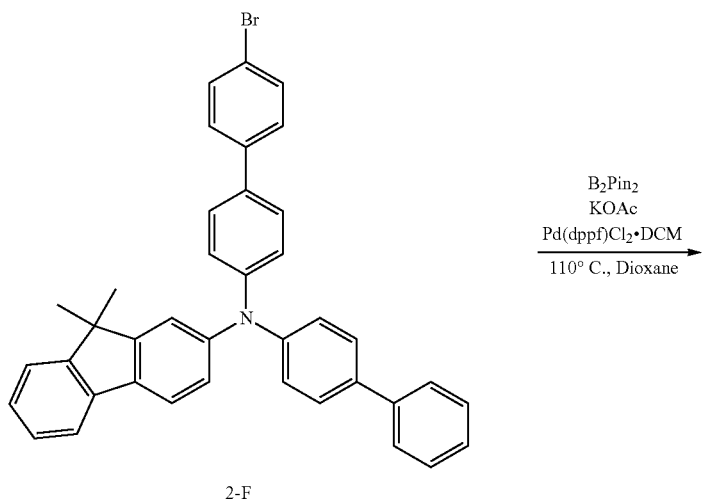

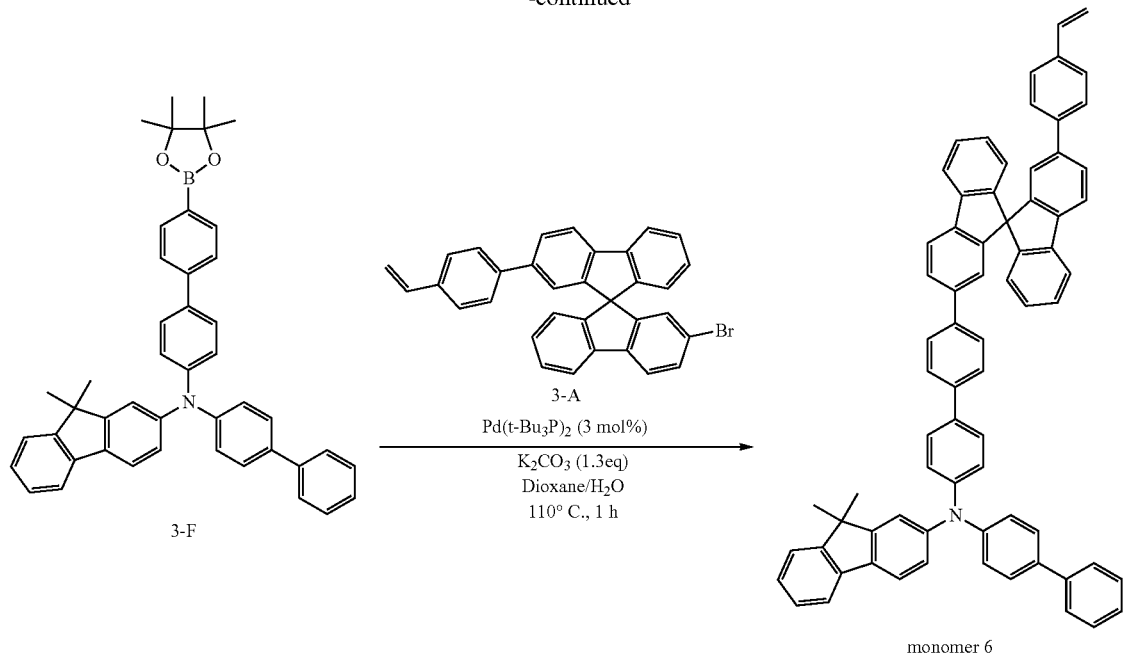
Monomer 6 was synthesized in the same manner as in the synthesis of Monomer 5 except that Compound 1-F was used instead of Compound 2-E.
MS: [M+H]$^+$=929
Synthesis of Monomer 7
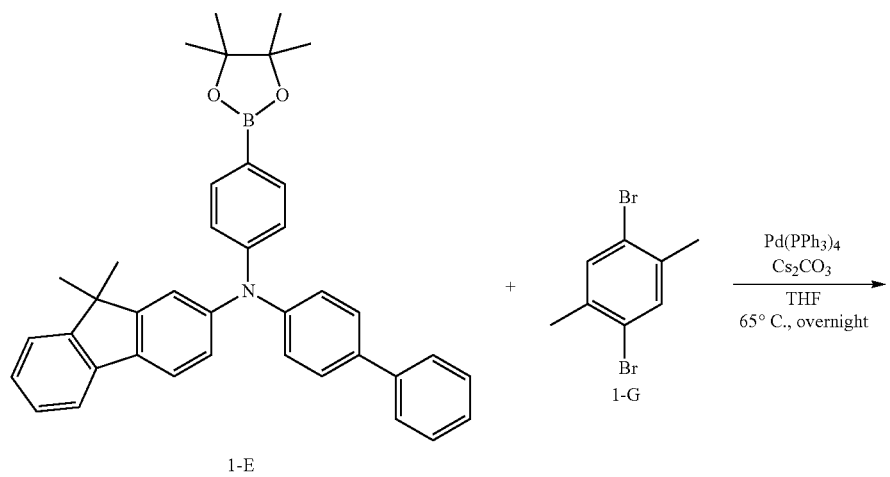

-continued
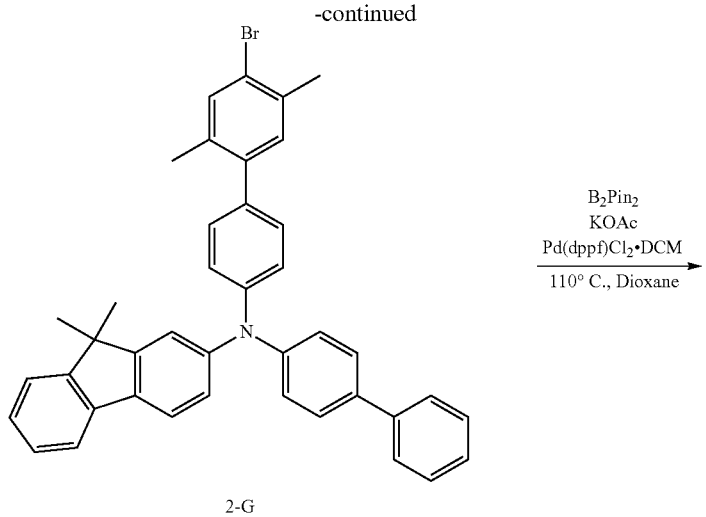
2-G
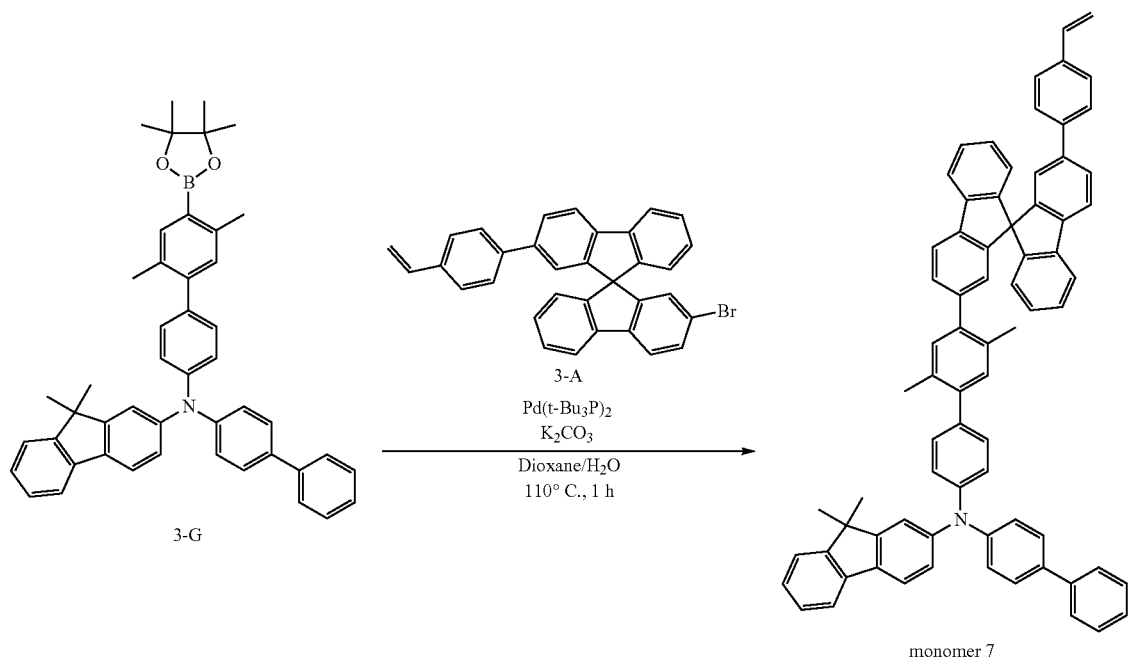
Monomer 7 was synthesized in the same manner as in the synthesis of Monomer 5 except that Compound 1-G was used instead of Compound 2-E.
MS: $[M+H]^+$=957

Synthesis of Monomer 8
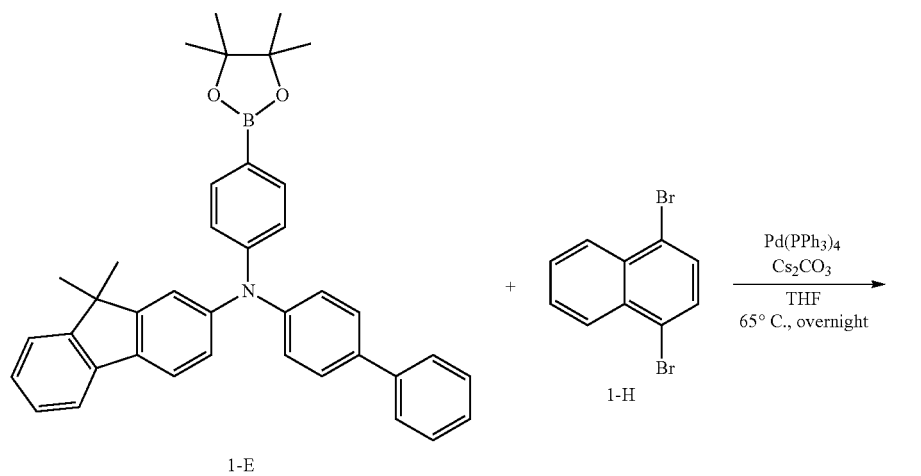
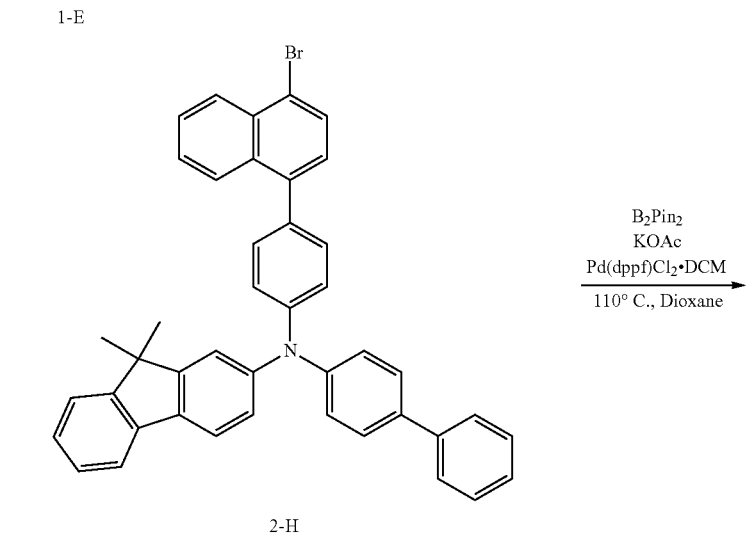
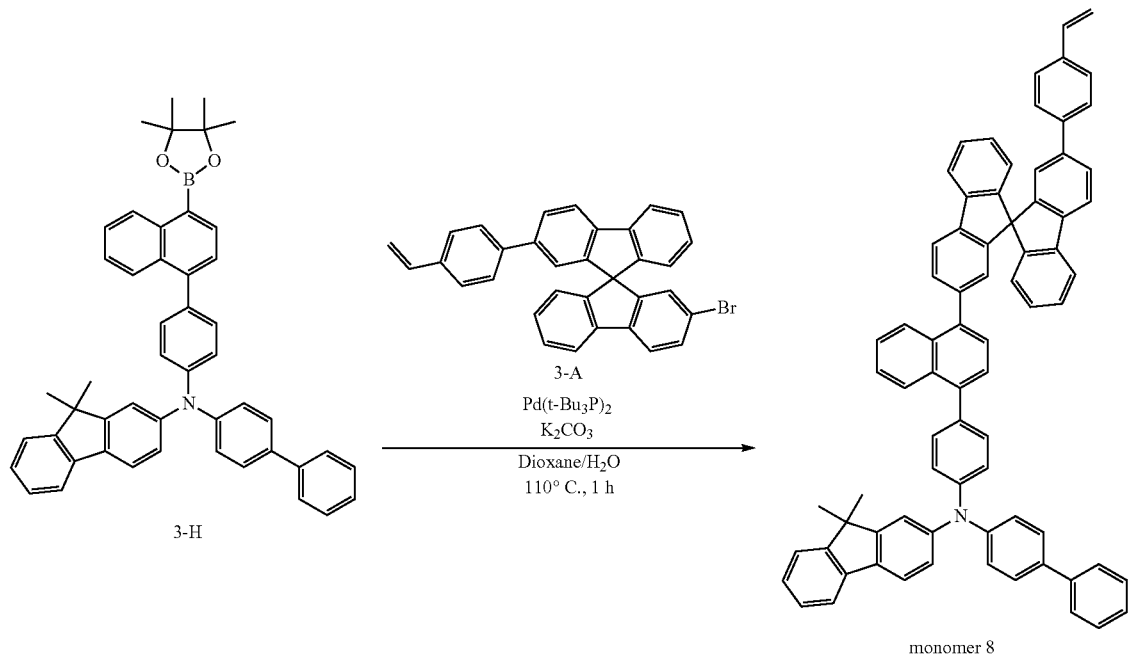

Monomer 8 was synthesized in the same manner as in the synthesis of Monomer 5 except that Compound 1-H was used instead of Compound 2-E.
MS: [M+H]$^+$=979
Synthesis of Monomer 9
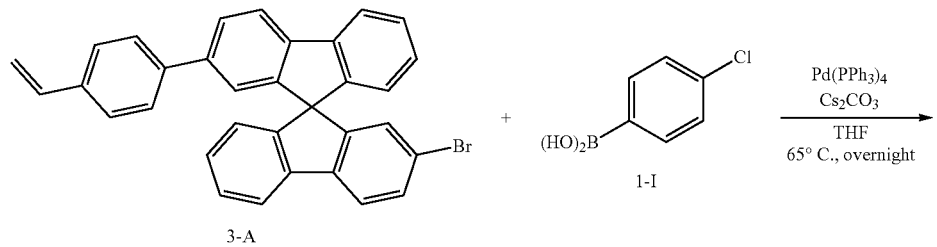
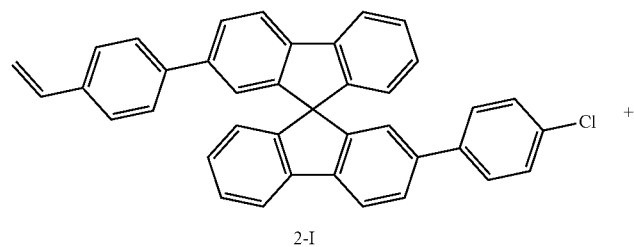
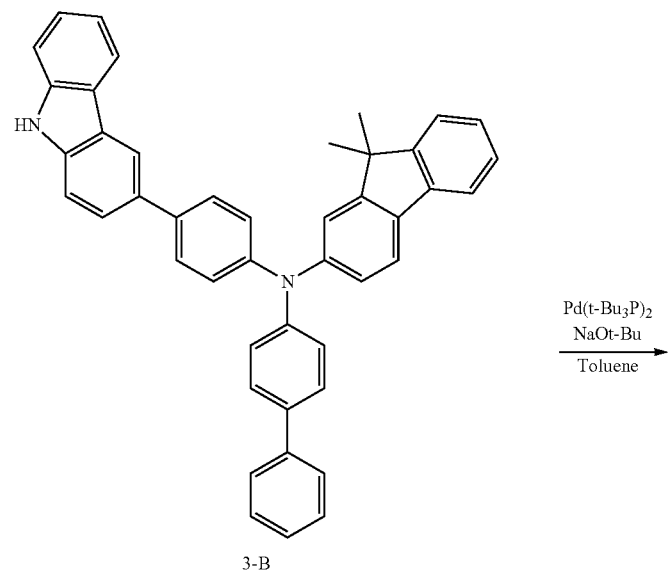

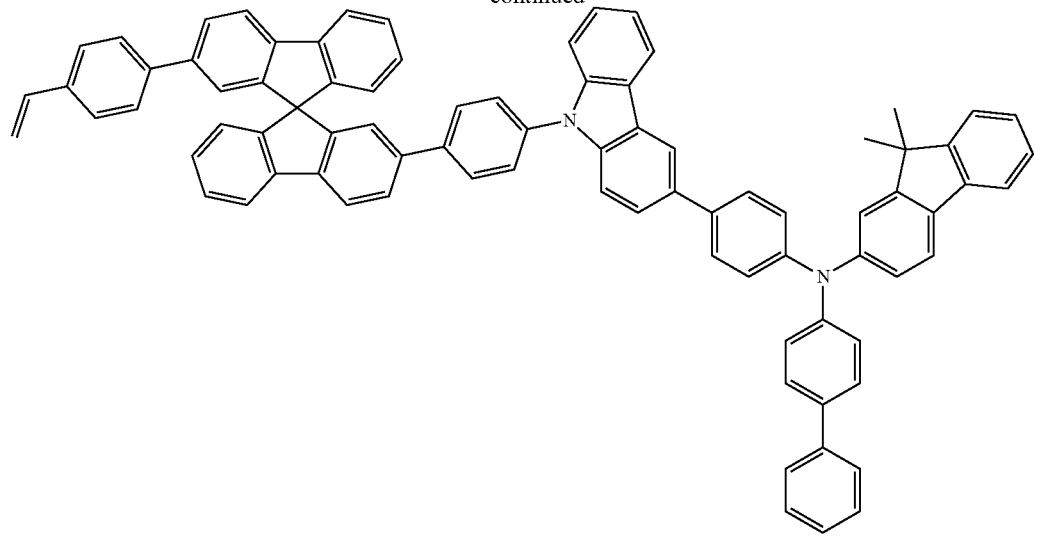

monomer 9

1) Synthesis of Compound 2-I

Compound 3-A (13.2 g, 26.6 mmol, 1.0 eq.) and Compound 1-I (4.58 g, 29.3 mmol, 1.1 eq.) were dissolved in tetrahydrofuran (THF) (100 mL), and stirred for 10 minutes in a 80° C. bath. $Cs_2CO_3$ (43.4 g, 133 mmol, 5.0 eq.) dissolved in water (90 mL) was added dropwise thereto for 10 minutes. $Pd(PPh_3)_4$ (1.54 g, 1.33 mol, 0.05 eq.) was introduced thereto under reflux. The result was stirred for 12 hours in a 65° C. bath, and then washed with ethyl acetate (EA)/$H_2O$ to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain Compound 2-I.

2) Synthesis of Monomer 9

Compound 3-B (3.6 g, 6 mmol, 1 eq.) and Compound 2-I (3.49 g, 6.6 mmol, 1.1 eq.) were dissolved in anhydrous toluene (36 ml), and stirred for 10 minutes in a 130° C. bath. Sodium tert-butoxide (NaOt-Bu) (1.45 g, 15 mmol, 2.5 eq.) was introduced thereto. A Pd catalyst (0.15 g, 0.3 mmol, 0.05 eq.) was introduced thereto under reflux. The result was stirred for 1 hour, and then washed with ethyl acetate (EA)/$H_2O$ to separate the organic layer, and the solvent was vacuum dried. The result was purified using column chromatography through n-hexane (n-Hex) and dichloromethane (DCM), and then recrystallized with n-hexane (n-Hex) to obtain white solid Monomer 9 (5.25 g).
MS: $[M+H]^+$=1094
Synthesis of Monomer 10

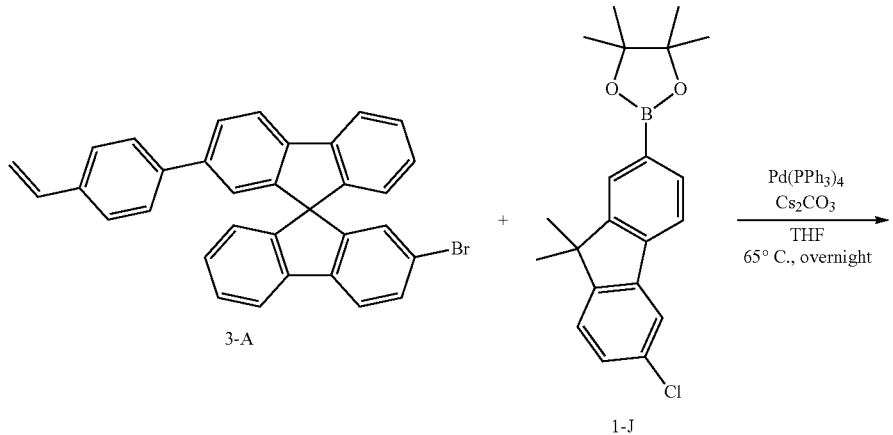

-continued
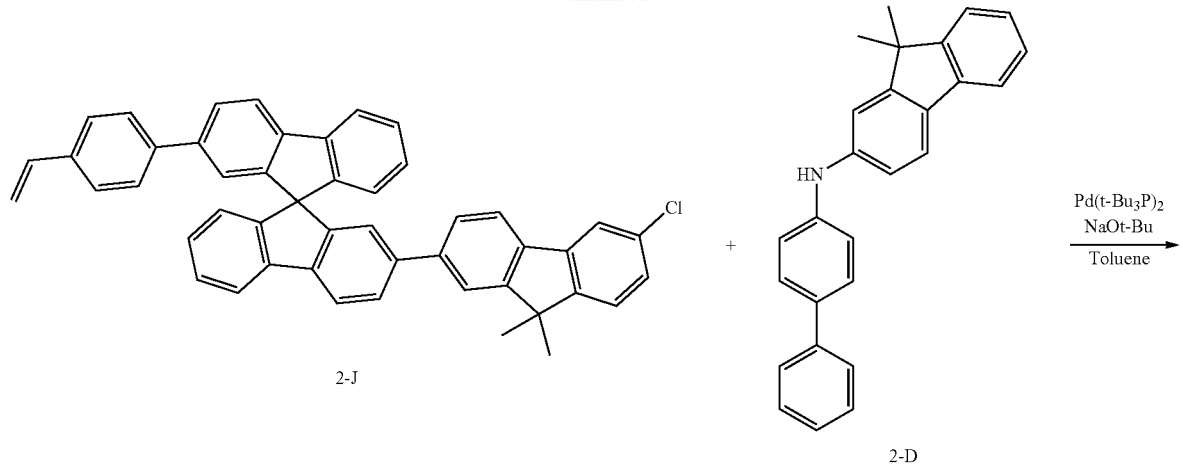
2-J
2-D
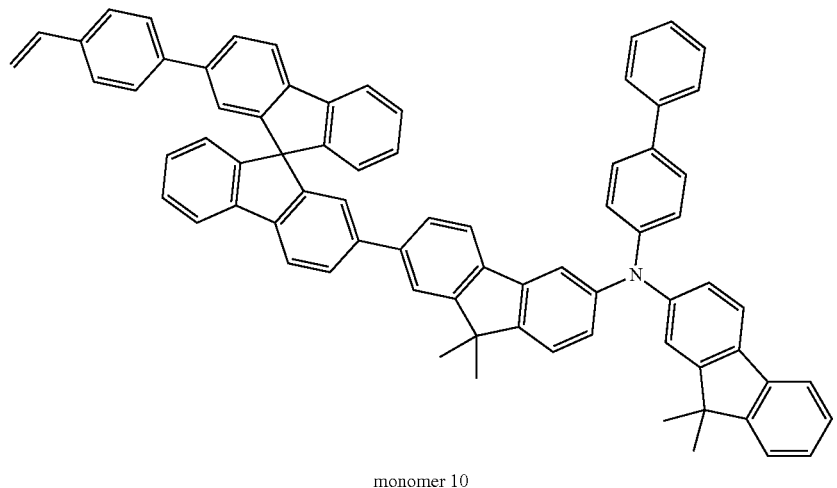
monomer 10
Monomer 10 was synthesized in the same manner as in the synthesis of Monomer 9 except that Compound 1-J was used instead of Compound 1-I, and Compound 2-D was used instead of Compound 3-B.
MS: [M+H]$^+$=969
Synthesis of Monomer 11
-continued
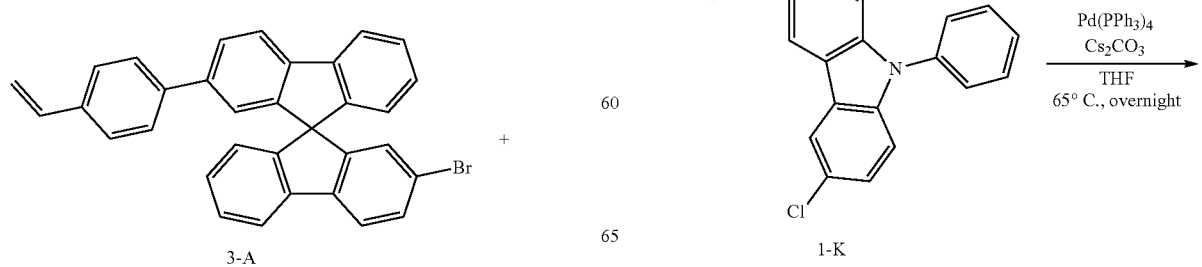
3-A
1-K

Synthesis of Monomer 12
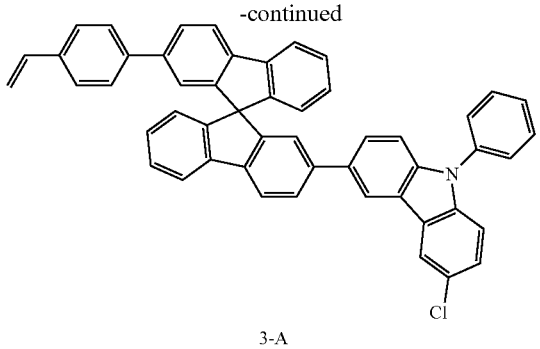
3-A
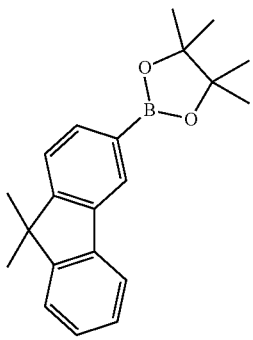
1-L
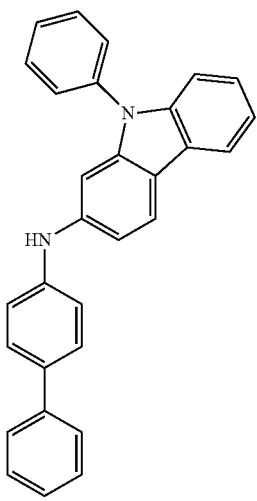
3-K
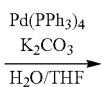
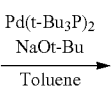
2-L
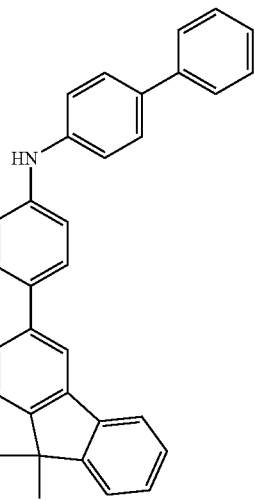
3-L
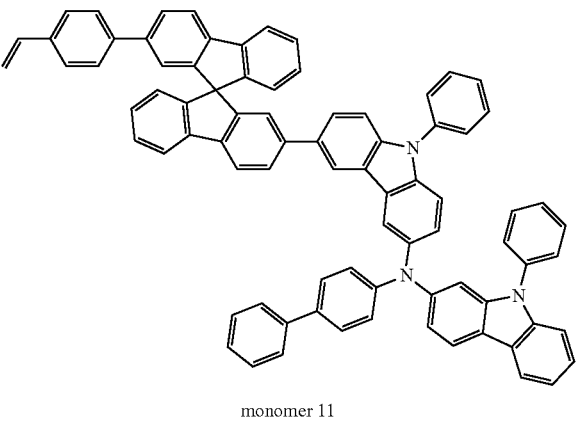
monomer 11
Monomer 11 was synthesized in the same manner as in the synthesis of Monomer 9 except that Compound 1-K was used instead of Compound 1-I, and Compound 3-K was used instead of Compound 3-B.
MS: $[M+H]^+=1067$
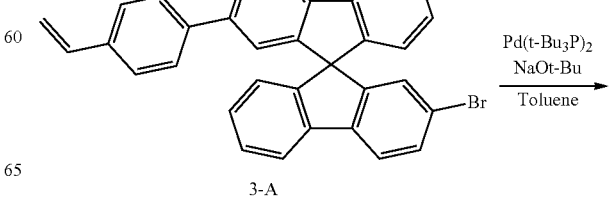
3-A

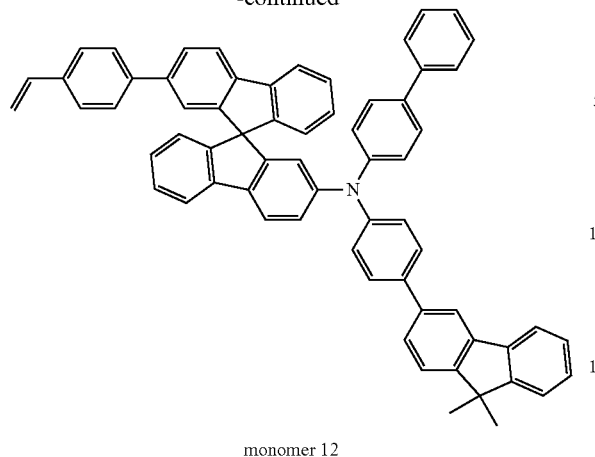

monomer 12

1) Synthesis of Compound 3-L

Compound 1-L (19.76 g, 60.95 mmol, 1.0 eq.) and Compound 2-L (20.50 g, 64 mmol, 1.05 eq.) were dissolved in tetrahydrofuran (THF) (200 mL), and stirred for 10 minutes in a 80° C. bath. $K_2CO_3$ (10.95 g, 79 mmol, 1.3 eq.) dissolved in water (87 mL) was added dropwise thereto for 10 minutes. A Pd catalyst (2.11 g, 1.8 mmol, 0.03 eq.) was introduced thereto under reflux. The result was stirred for 12 hours, and then washed with ethyl acetate (EA)/$H_2O$ to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain Compound 3-L.

2) Synthesis of Monomer 12

Compound 3-L (2.63 g, 6 mmol, 1 eq.) and Compound 3-A (3.28 g, 6.6 mmol, 1.1 eq.) were dissolved in anhydrous toluene (15 g), and stirred for 10 minutes in a 130° C. bath. Sodium tert-butoxide (NaOt-Bu) (1.45 g, 15 mmol, 2.5 eq.) was introduced thereto. A Pd catalyst (0.077 g, 0.15 mmol, 0.03 eq.) was introduced thereto under reflux. The result was stirred for 1 hour, and then washed with ethyl acetate (EA)/$H_2O$ to separate the organic layer, and the solvent was vacuum dried. The result was purified using column chromatography through n-hexane (n-Hex) and dichloromethane (DCM), and then recrystallized with n-hexane (n-Hex) to obtain white solid Monomer 12 (4.82 g).

MS: [M+H]$^+$=853

Synthesis of Monomer 13

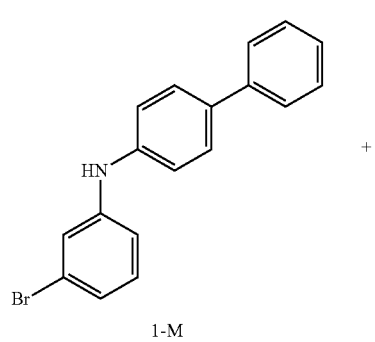

1-M

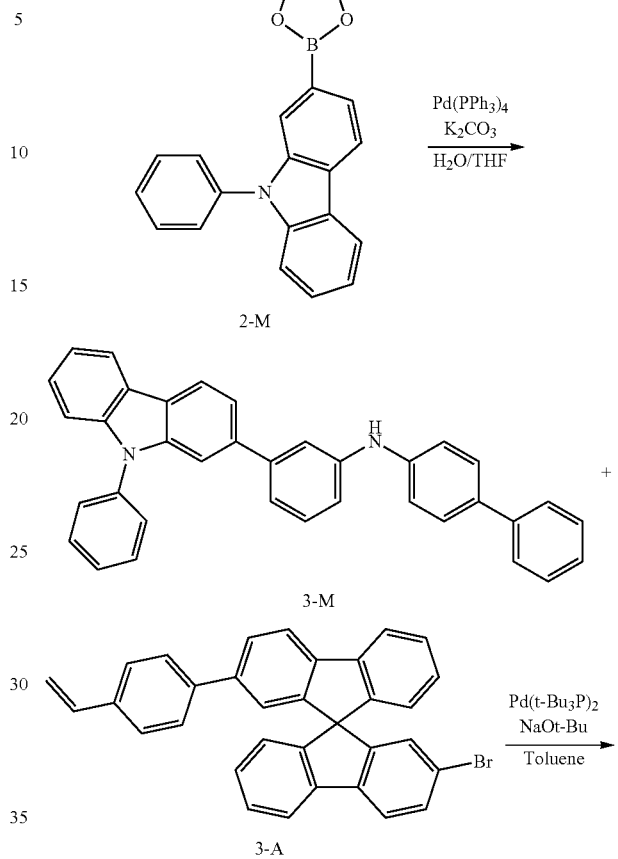

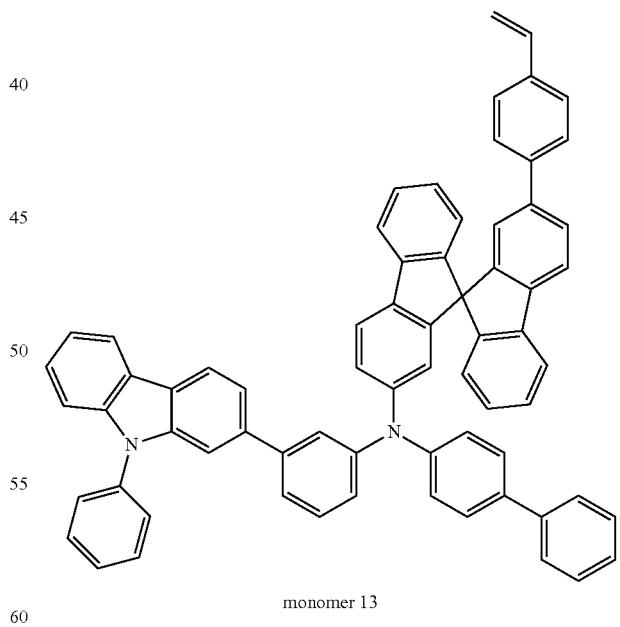

monomer 13

Monomer 13 was synthesized in the same manner as in the synthesis of Monomer 12 except that Compound 1-M was used instead of Compound 1-L, and Compound 2-M was used instead of Compound 2-L.

MS: [M+H]$^+$=902

Synthesis of Monomer 14

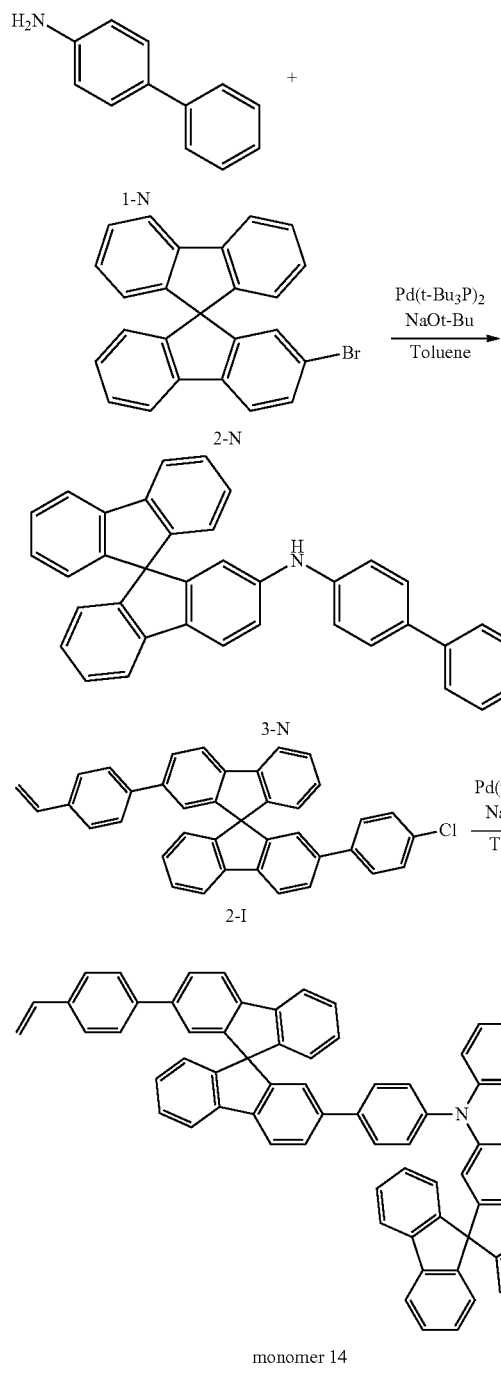

monomer 14

1) Synthesis of Compound 3-N Compound 1-N (1.11 g, 6 mmol, 1 eq.) and Compound 2-N (2.37 g, 6.6 mmol, 1.1 eq.) were dissolved in anhydrous toluene (15 ml), and stirred for 10 minutes in a 80° C. bath. Sodium tert-butoxide (NaOt-Bu) (1.45 g, 15 mmol, 2.5 eq.) and a Pd catalyst (0.03 g, 0.06 mmol, 0.01 eq.) were introduced thereto at 80° C. The result was stirred for 1 hour, and then washed with ethyl acetate (EA)/H$_2$O to separate the organic layer, and the solvent was vacuum dried. The result was purified using column chromatography through n-hexane (n-Hex) and dichloromethane (DCM), and then recrystallized with n-hexane (n-Hex) to obtain white solid Compound 3-N.

2) Synthesis of Monomer 14

Compound 3-N (2.90 g, 6 mmol, 1 eq.) and Compound 2-I (3.49 g, 6.6 mmol, 1.1 eq.) were dissolved in anhydrous toluene (30 ml), and stirred for 10 minutes in a 120° C. bath. Sodium tert-butoxide (NaOt-Bu) (1.45 g, 15 mmol, 2.5 eq.) and a Pd catalyst (0.15 g, 0.30 mmol, 0.05 eq.) were introduced thereto under reflux. The result was stirred for 1 hour, and then washed with ethyl acetate (EA)/H$_2$O to separate the organic layer, and the solvent was vacuum dried. The result was purified using column chromatography through n-hexane (n-Hex) and dichloromethane (DCM), and then recrystallized with n-hexane (n-Hex) to obtain white solid Monomer 14 (4.92 g).

MS: [M+H]$^+$=975

Synthesis of Monomer 15

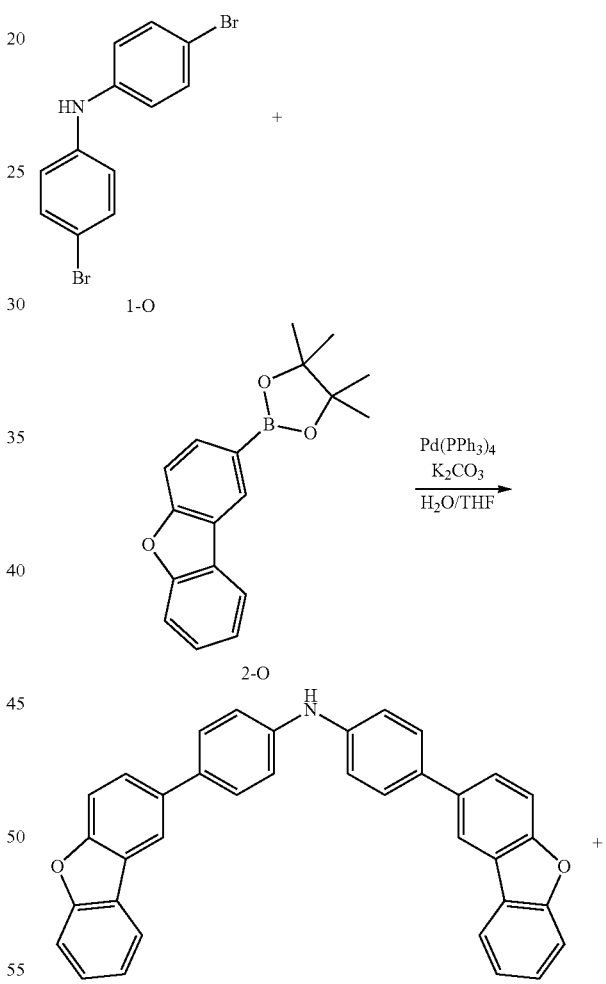

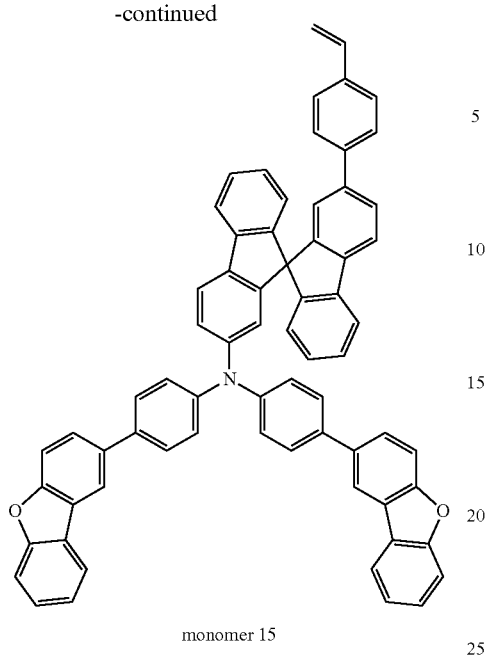

monomer 15

1) Synthesis of Compound 3-0

Compound 1-0 (19.93 g, 60.95 mmol, 1.0 eq.) and Compound 2-0 (37.65 g, 128 mmol, 2.10 eq.) were dissolved in tetrahydrofuran (THF) (200 mL), and stirred for 10 minutes in a 80° C. bath. $K_2CO_3$ (21.9 g, 158 mmol, 2.6 eq.) dissolved in water (87 mL) was added dropwise thereto for 10 minutes. A Pd catalyst (2.11 g, 1.8 mmol, 0.03 eq.) was introduced thereto under reflux. The result was stirred for 12 hours, and then washed with ethyl acetate (EA)/$H_2O$ to separate the organic layer, and the solvent was vacuum dried. The result was purified using medium pressure liquid chromatography (MPLC) through n-hexane (n-Hex) and ethyl acetate (EA), and then recrystallized with n-hexane (n-Hex) to obtain Compound 3-0.

2) Synthesis of Monomer 15

Compound 3-0 (3.01 g, 6 mmol, 1 eq.) and Compound 3-A (3.28 g, 6.6 mmol, 1.1 eq.) were dissolved in anhydrous toluene (15 g), and stirred for 10 minutes in a 130° C. bath. Sodium tert-butoxide (NaOt-Bu) (1.45 g, 15 mmol, 2.5 eq.) was introduced thereto. A Pd catalyst (0.077 g, 0.15 mmol, 0.03 eq.) was introduced thereto under reflux. The result was stirred for 1 hour, and then washed with ethyl acetate (EA)/$H_2O$ to separate the organic layer, and the solvent was vacuum dried. The result was purified using column chromatography through n-hexane (n-Hex) and dichloromethane (DCM), and then recrystallized with n-hexane (n-Hex) to obtain white solid Monomer 15 (5.07 g).

MS: $[M+H]^+ = 917$

Preparation of Polymer 1

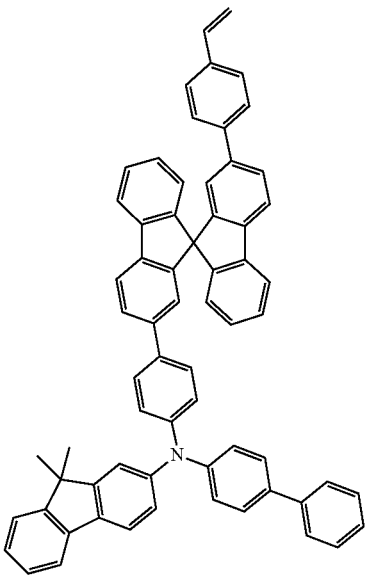

monomer 1

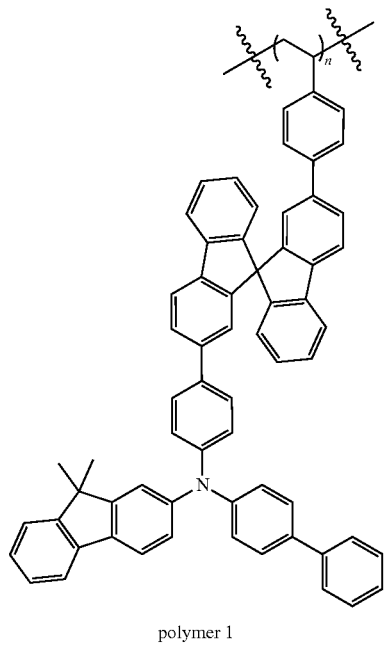

polymer 1

Monomer 1 (500 mg) and azobisisobutyronitrile (AIBN) (1.2 mg) were introduced to ethyl acetate (EA), and reacted for 12 hours at 25° C. under nitrogen substitution. After the reaction, produced precipitates were filtered to prepare Polymer 1.

Mn: 37100 g/mol, Mw: 78600 g/mol

Preparation of Polymers 2 to 15

Polymers 2 to 15 were prepared in the same manner as the method for preparing Polymer 1 except that monomers of the following Table 1 were used instead of Monomer 1.

Preparation of Polymers P1 and P2

Polymers P1 and P2 were prepared in the same manner as the method for preparing Polymer 1 except that monomers of the following Table 1 were used instead of Monomer 1.

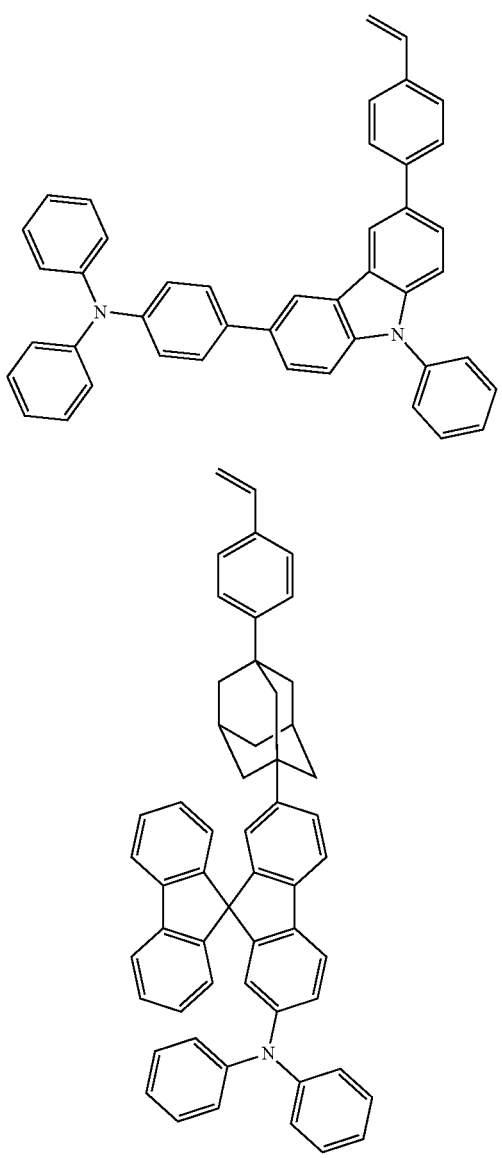

C1

C2

Example 1-1

A glass substrate on which indium tin oxide (ITO) was coated as a thin film to a thickness of 150 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone, then dried, cleaned for 5 minutes, and then transported to a glove box.

On the transparent ITO electrode, a 2 wt/v % toluene coating composition of Polymer 1 and the following Compound M (weight ratio of 8:2) was spin coated (4000 rpm), and heat treated (cured) for 30 minutes at 200° C. to form a hole injection layer to a thickness of 40 nm. After the result was transported to a vacuum deposition apparatus, a hole transfer layer having a thickness of 20 nm was formed on the hole injection layer by vacuum depositing the following Compound G. On the hole transfer layer, a light emitting layer was formed by vacuum depositing the following Compound H and the following Compound I in a weight ratio of 92:8 to a thickness of 20 nm. On the light emitting layer, an electron injection and transfer layer was formed by vacuum depositing the following Compound J to a thickness of 35 nm. On the electron injection and transfer layer, LiF and aluminum were consecutively deposited to a thickness of 1 nm and a thickness of 100 nm, respectively, to form a cathode.

In the above-mentioned process, the deposition rates of the organic materials were maintained at 0.04 nm/sec to 0.07 nm/sec, the deposition rates of the LiF and the aluminum were maintained at 0.03 nm/sec and 0.2 nm/sec, respectively, and the degree of vacuum during the deposition was maintained at $2 \times 10^{-7}$ torr to $5 \times 10^{-6}$ torr.

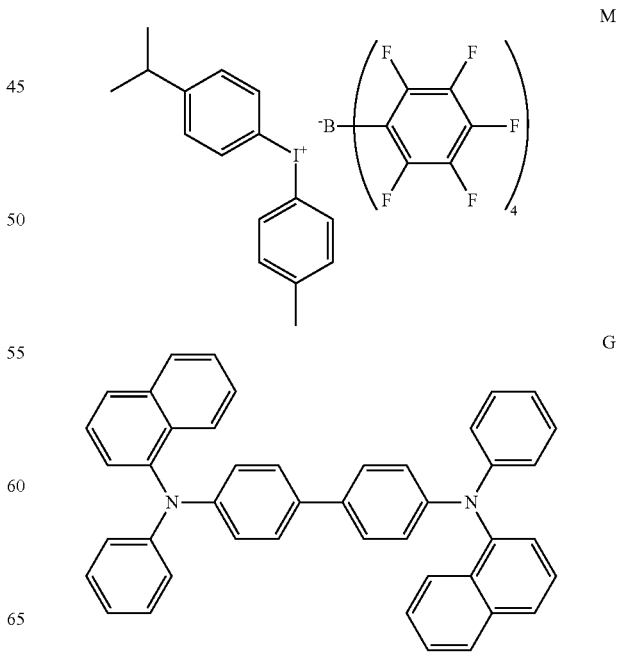

M

G

TABLE 1

| Polymer | Monomer | Mn (g/mol) | Mw (g/mol) |
|---|---|---|---|
| 1 | 1 | 37100 | 78600 |
| 2 | 2 | 41400 | 75100 |
| 3 | 3 | 26500 | 44600 |
| 4 | 4 | 24800 | 45200 |
| 5 | 5 | 17200 | 29300 |
| 6 | 6 | 21400 | 39200 |
| 7 | 7 | 22100 | 39400 |
| 8 | 8 | 23600 | 41400 |
| 9 | 9 | 28100 | 55100 |
| 10 | 10 | 19300 | 31200 |
| 11 | 11 | 26400 | 49400 |
| 12 | 12 | 49600 | 95400 |
| 13 | 13 | 51600 | 105000 |
| 14 | 14 | 23500 | 41100 |
| 15 | 15 | 48100 | 91200 |
| P1 | C1 | 37800 | 77900 |
| P2 | C2 | 51200 | 113400 |

H

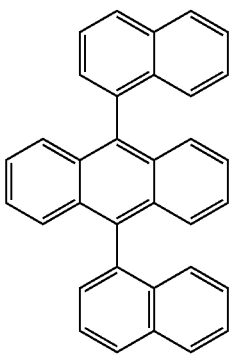

I

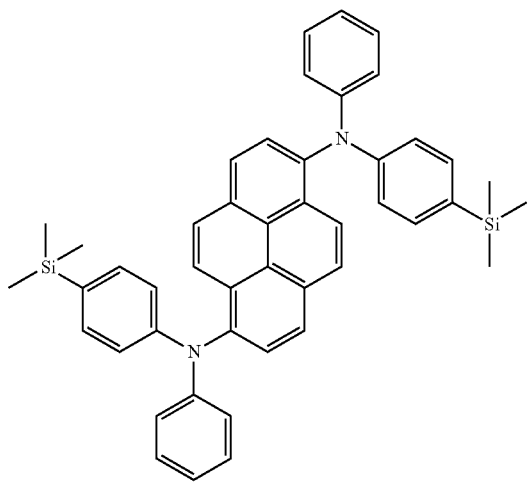

J

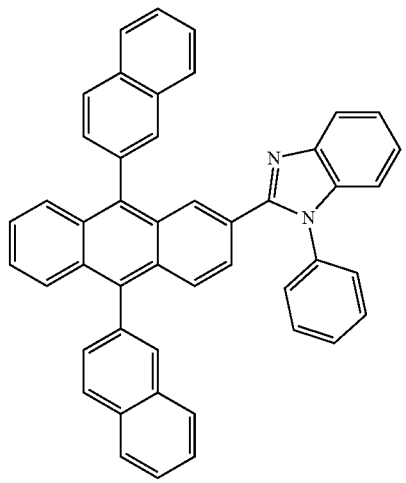

Comparative Example 1-1

An organic light emitting device of Comparative Example 1-1 was manufactured in the same manner as in Example 1-1 except that a polymer of the following Table 2 was used instead of Polymer 1.

Example 2-1

A glass substrate on which indium tin oxide (ITO) was coated as a thin film to a thickness of 150 nm was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone, then dried, cleaned for 5 minutes, and then transported to a glove box.

On the transparent ITO electrode, a coating composition dissolving Compound K and Compound L (weight ratio of 8:2) in 2 wt/v % cyclohexanone was spin coated (4000 rpm), and heat treated (cured) for 30 minutes at 230° C. to form a hole injection layer to a thickness of 40 nm. On the hole injection layer, a hole transfer layer having a thickness of 20 nm was formed by spin coating a composition dissolving Polymer 1 in toluene in 2 wt % and heat treating the result for 30 minutes at 230° C. On the hole transfer layer, a light emitting layer was formed to a thickness of 25 nm by spin coating (4000 rpm) a coating composition dissolving the following Compound H and the following Compound I in a weight ratio of 92:8 in 2 wt/v % cyclohexanone, and heat treating the result for 30 minutes at 150° C. After the result was transported to a vacuum deposition apparatus, an electron injection and transfer layer was formed on the light emitting layer by vacuum depositing the following Compound J to a thickness of 35 nm. On the electron injection and transfer layer, LiF and aluminum were consecutively deposited to a thickness of 1 nm and a thickness of 100 nm, respectively, to form a cathode.

K

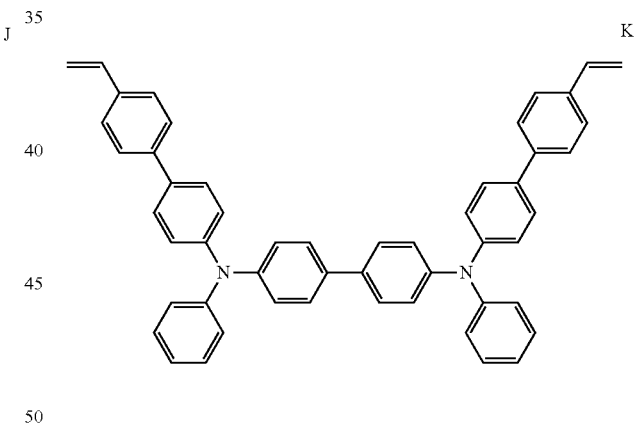

L

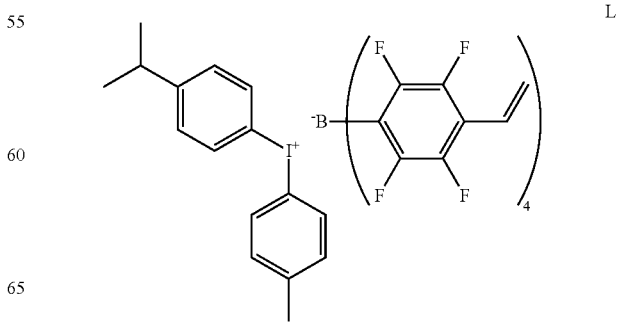

-continued

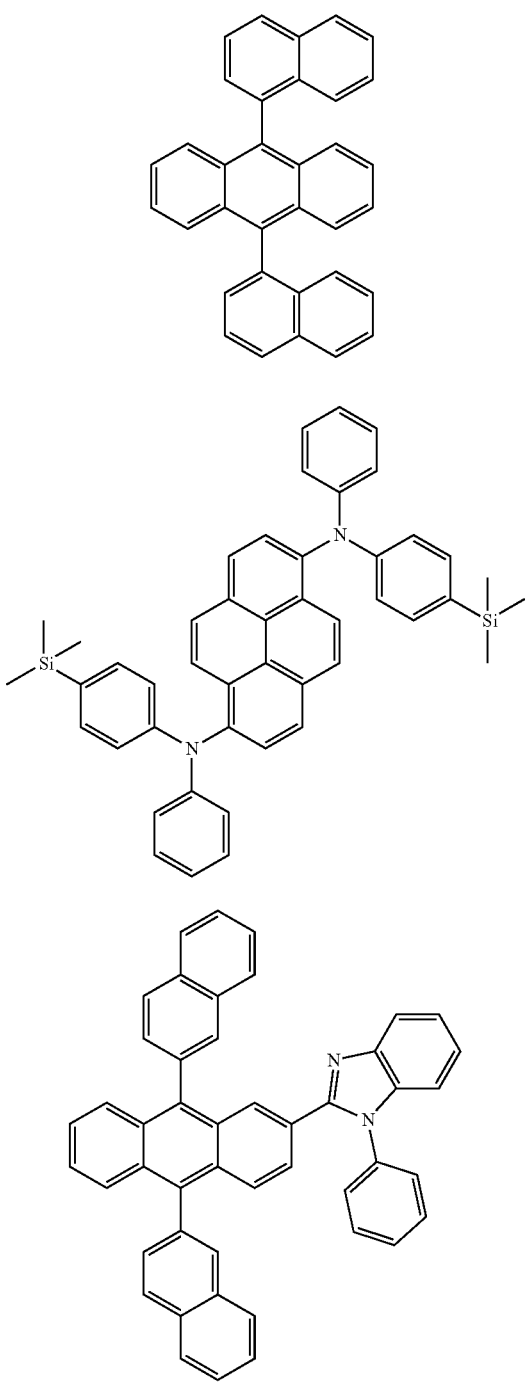

In the above-mentioned process, the deposition rates of the organic materials were maintained at 0.04 nm/sec to 0.07 nm/sec, the deposition rates of the LiF and the aluminum were maintained at 0.03 nm/sec and 0.2 nm/sec, respectively, and the degree of vacuum during the deposition was maintained at $2\times10^{-7}$ torr to $5\times10^{-6}$ torr.

Examples 2-2 to 2-13

Organic light emitting devices of Examples 2-2 to 2-13 were manufactured in the same manner as in Example 2-1 except that polymers of the following Table 2 were used instead of Polymer 1.

Comparative Examples 2-1 and 2-2

Organic light emitting devices of Comparative Examples 2-1 and 2-2 were manufactured in the same manner as in Example 2-except that polymers of the following Table 2 were used instead of Polymer 1.

Comparative Example 2-3

An organic light emitting device of Comparative Example 2-3 was manufactured in the same manner as in Example 2-1 except that the following Compound P3 was used instead of Polymer 1 when forming the hole transfer layer of Example 2-1.

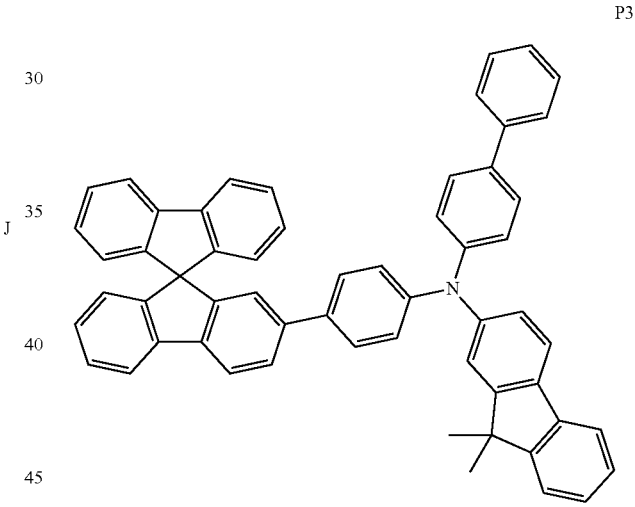

Evaluation on Device

For the organic light emitting devices manufactured in the examples and the comparative examples, results of measuring driving voltage, external quantum efficiency (EQE), luminance and lifetime at current density of 10 mA/cm² are shown in the following Table 2. The external quantum efficiency was obtained by (the number of emitted photons)/(the number of injected charge carriers). T90 means time taken for luminance decreasing to 90% from initial luminance (500 nit).

TABLE 2

|  | Compound | Driving Voltage (V) | Current Density (mA/cm²) | EQE (%) | Lifetime (hr) (T90 at 500 nit) |
|---|---|---|---|---|---|
| Example 1-1 | Polymer 1 | 4.48 | 10 | 7.9 | 190 |
| Comparative Example 1-1 | Polymer P1 | 3.89 | 10 | 5.7 | 60 |

TABLE 2-continued

|  | Compound | Driving Voltage (V) | Current Density (mA/cm$^2$) | EQE (%) | Lifetime (hr) (T90 at 500 nit) |
|---|---|---|---|---|---|
| Example 2-1 | Polymer 1 | 4.48 | 10 | 6.9 | 247 |
| Example 2-2 | Polymer 2 | 4.14 | 10 | 6.8 | 238 |
| Example 2-3 | Polymer 3 | 4.45 | 10 | 6.6 | 248 |
| Example 2-4 | Polymer 4 | 4.45 | 10 | 6.7 | 246 |
| Example 2-5 | Polymer 5 | 4.49 | 10 | 6.6 | 237 |
| Example 2-6 | Polymer 6 | 4.46 | 10 | 6.7 | 239 |
| Example 2-7 | Polymer 7 | 4.46 | 10 | 6.7 | 239 |
| Example 2-8 | Polymer 8 | 4.48 | 10 | 6.8 | 242 |
| Example 2-9 | Polymer 9 | 4.49 | 10 | 6.9 | 235 |
| Example 2-10 | Polymer 10 | 4.21 | 10 | 6.6 | 250 |
| Example 2-11 | Polymer 11 | 4.25 | 10 | 6.9 | 244 |
| Example 2-12 | Polymer 12 | 4.31 | 10 | 6.6 | 243 |
| Example 2-13 | Polymer 13 | 4.24 | 10 | 6.7 | 244 |
| Comparative Example 2-1 | Polymer P1 | 4.01 | 10 | 6.0 | 84 |
| Comparative Example 2-2 | Polymer P2 | 4.27 | 10 | 6.1 | 209 |
| Comparative Example 2-3 | Compound P3 | Unable to Measure | Unable to Measure | Unable to Measure | Unable to Measure |

It was identified that the device of Example 1-1 using a polymer including spirobifluorene in a hole injection layer had external quantum efficiency improved by approximately 38%, and a lifetime improved by approximately 216% compared to the device of Comparative Example 1-1 using a polymer that does not include spirobifluorene. It was identified that the device of Example 2-1 using a polymer including spirobifluorene in a hole transfer layer had external quantum efficiency improved by approximately 15%, and a lifetime improved by approximately 190% or greater compared to the device of Comparative Example 2-1 using a polymer that does not include spirobifluorene.

In addition, the polymer according to one embodiment of the present specification had excellent solubility for organic solvents, and a coating composition was readily prepared. From the results of Table 1, it was identified that a uniform coating layer was able to be formed using the coating composition and film stability was excellent as well, and as a result, more superior performance was obtained in the organic light emitting device.

In addition, it was identified that, from the device examples of Examples 2-1 to 2-13, the polymer including the unit of Chemical Formula 1 according to one embodiment of the present disclosure had tolerance for a solvent such as cyclohexanone. In other words, forming an organic material layer with the polymer including the unit of Chemical Formula 1 according to one embodiment of the present disclosure has an advantage in that other organic material layers may be formed on the organic material layer using a solution process.

In the device of Comparative Example 2-3, a hole transfer layer was formed using a monomer of Compound P3. However, when spin coating a light emitting layer composition on the hole transfer layer formed using Compound P3, Compound P3 was dissolved in cyclohexanone making light emitting layer formation difficult, and a device was not able to be formed. As a result, data values of Comparative Example 2-3 of Table 2 were not able to be measured.

The invention claimed is:
1. A polymer comprising a unit represented by the following Chemical Formula 1:

[Chemical Formula 1]

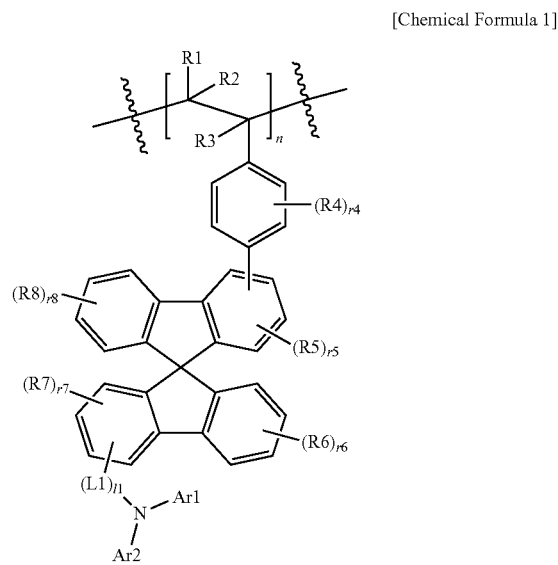

wherein, in Chemical Formula 1,
L1 is a direct bond; a substituted or unsubstituted phenylene group; a substituted or unsubstituted naphthylene group; a substituted or unsubstituted biphenylene group; a substituted or unsubstituted divalent fluorenyl group; or a substituted or unsubstituted divalent carbazolyl group;
l1 is an integer of 1 to 10;
Ar1 and Ar2 are the same as or different from each other, and each independently a substituted or unsubstituted aryl group; or a substituted or unsubstituted heteroaryl group;
R1 to R8 are the same as or different from each other, and each independently hydrogen;

deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group;

r4, r6 and r8 are each independently an integer of 1 to 4;

r5 and r7 are each independently an integer of 1 to 3;

when r4 is 2 or greater, the two or more R4s are the same as or different from each other;

when r5 is 2 or greater, the two or more R5s are the same as or different from each other;

when r6 is 2 or greater, the two or more R6s are the same as or different from each other;

when r7 is 2 or greater, the two or more R7s are the same as or different from each other;

when r8 is 2 or greater, the two or more R8s are the same as or different from each other;

when l1 is 2 or greater, the two or more L1s are the same as or different from each other; and n is, as a repetition number of the unit, an integer of 1 to 10,000.

2. The polymer of claim 1, wherein the unit represented by Chemical Formula 1 is represented by the following Chemical Formula 1-1:

[Chemical Formula 1-1]

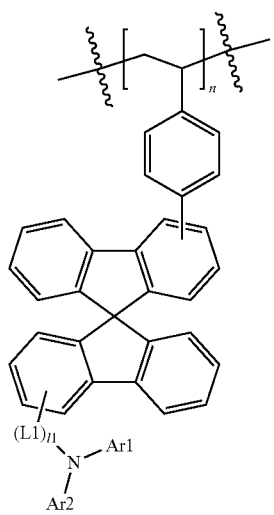

in Chemical Formula 1-1,

L1, l1, Ar1, Ar2 and n have the same definitions as in Chemical Formula 1.

3. The polymer of claim 1, wherein L1 is a direct bond; a phenylene group unsubstituted or substituted with an alkyl group; an unsubstituted naphthylene group; an unsubstituted biphenylene group; a divalent fluorenyl group unsubstituted or substituted with an alkyl group; or a divalent carbazolyl group unsubstituted or substituted with an aryl group.

4. The polymer of claim 1, wherein Ar1 and Ar2 are the same as or different from each other, and each independently an aryl group unsubstituted or substituted with an unsubstituted aryl group; an aryl group substituted with an unsubstituted heteroaryl group; an aryl group substituted with an alkyl group; an aryl group substituted with an aryl group substituted with an alkyl group; an aryl group substituted with a heteroaryl group substituted with an aryl group; or a heteroaryl group unsubstituted or substituted with an unsubstituted or substituted aryl group.

5. The polymer of claim 1, wherein the unit represented by Chemical Formula 1 is selected from among the following structures:

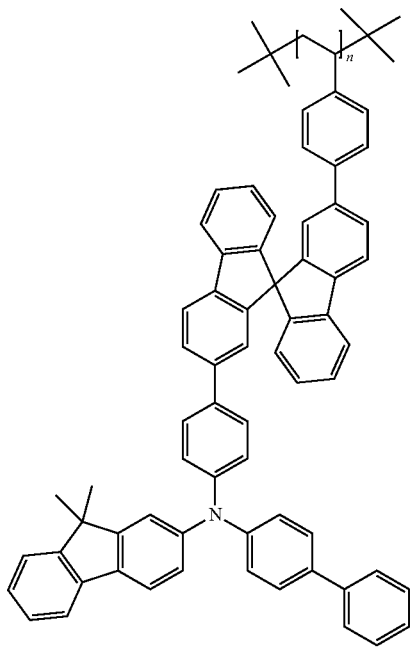

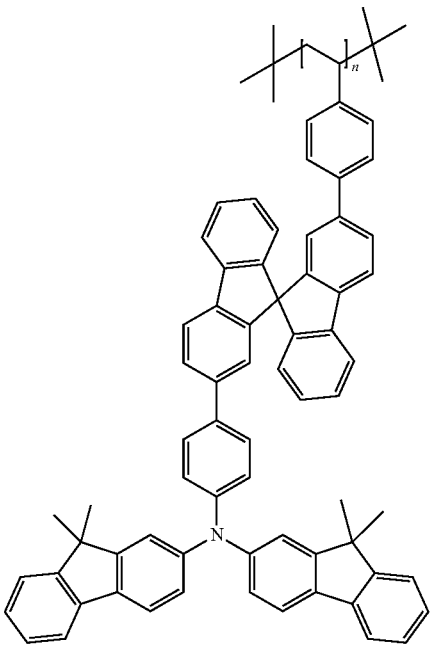

103
-continued
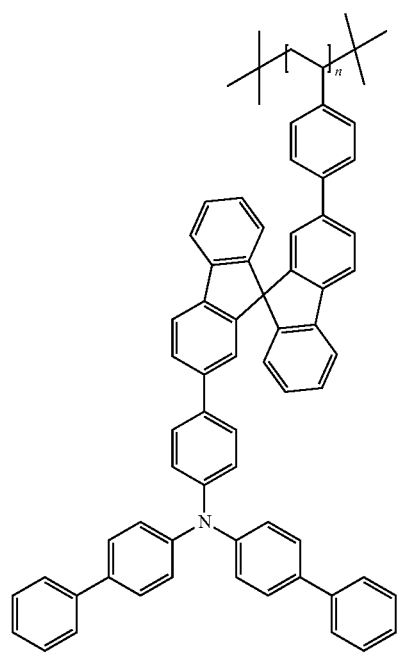
104
-continued
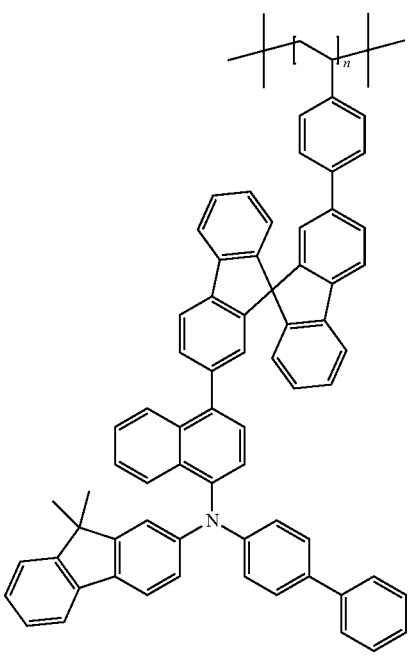
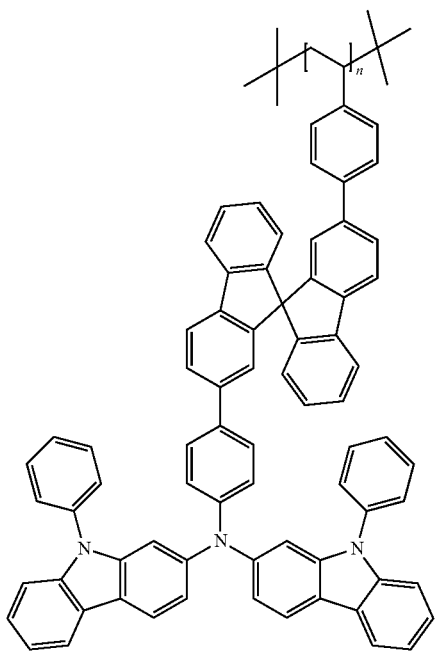
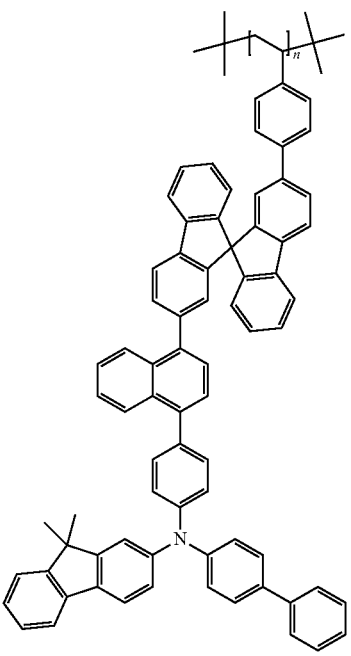

105
-continued
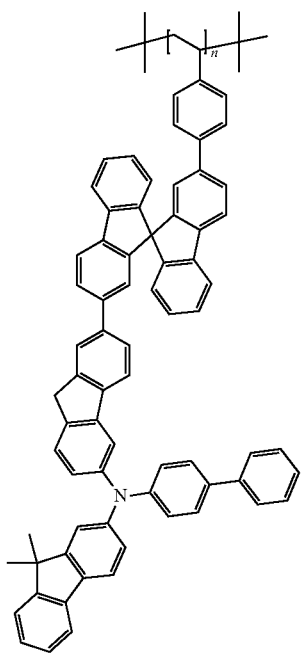
106
-continued
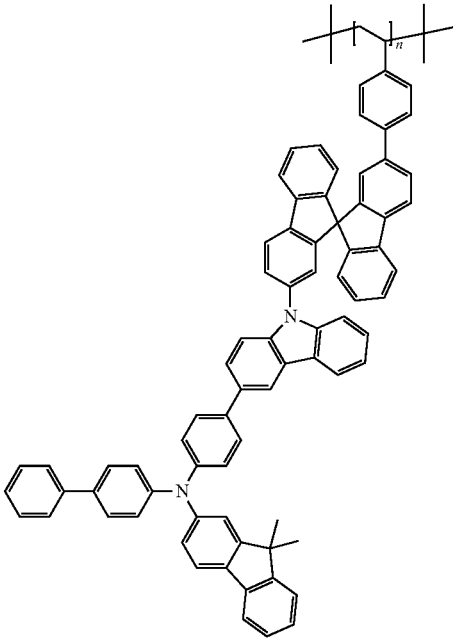
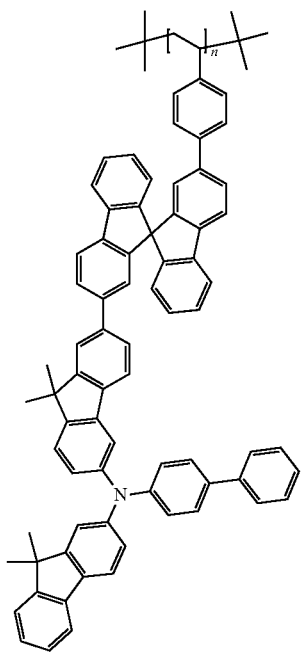
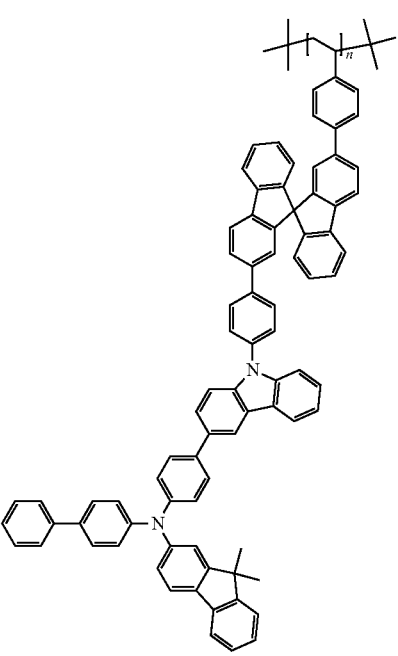

107
-continued
108
-continued
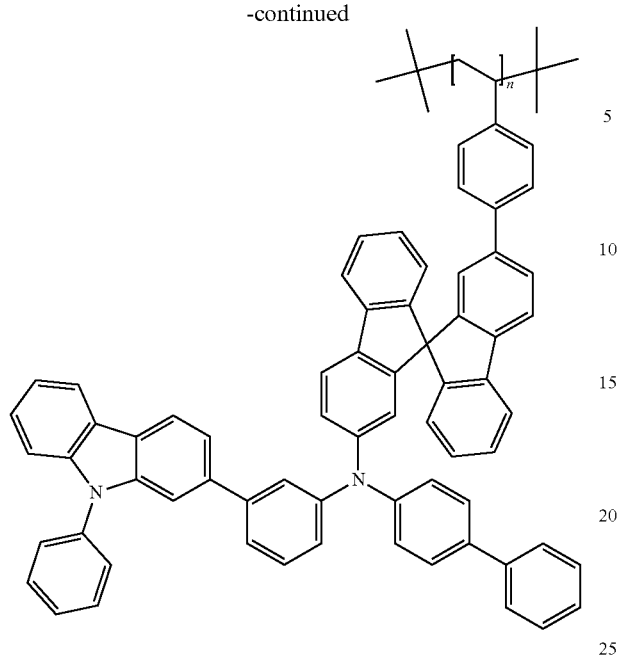
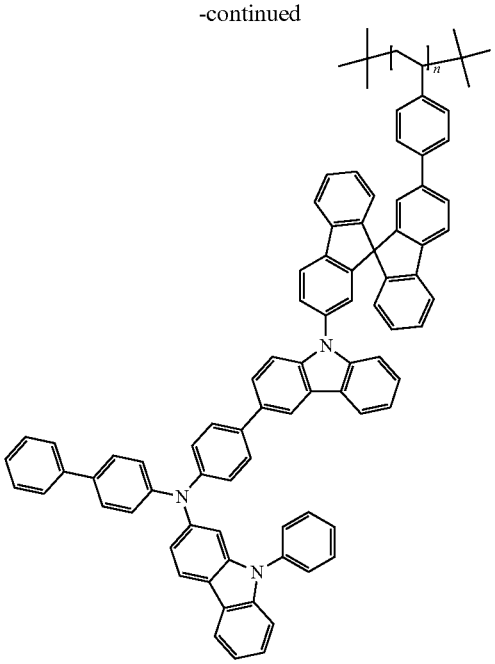

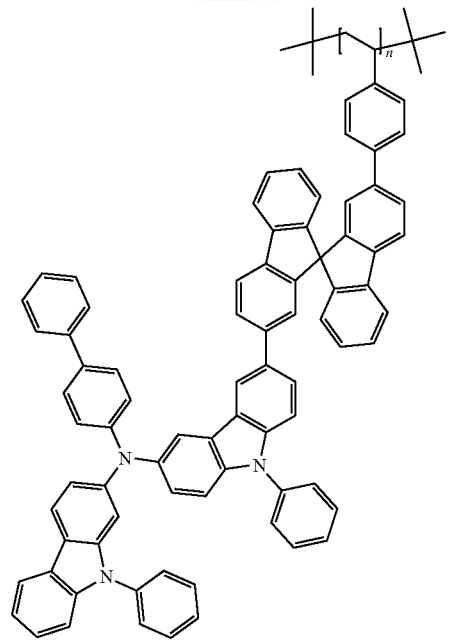
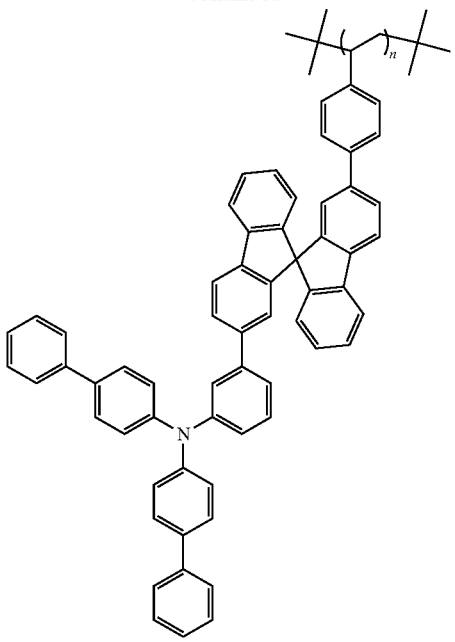
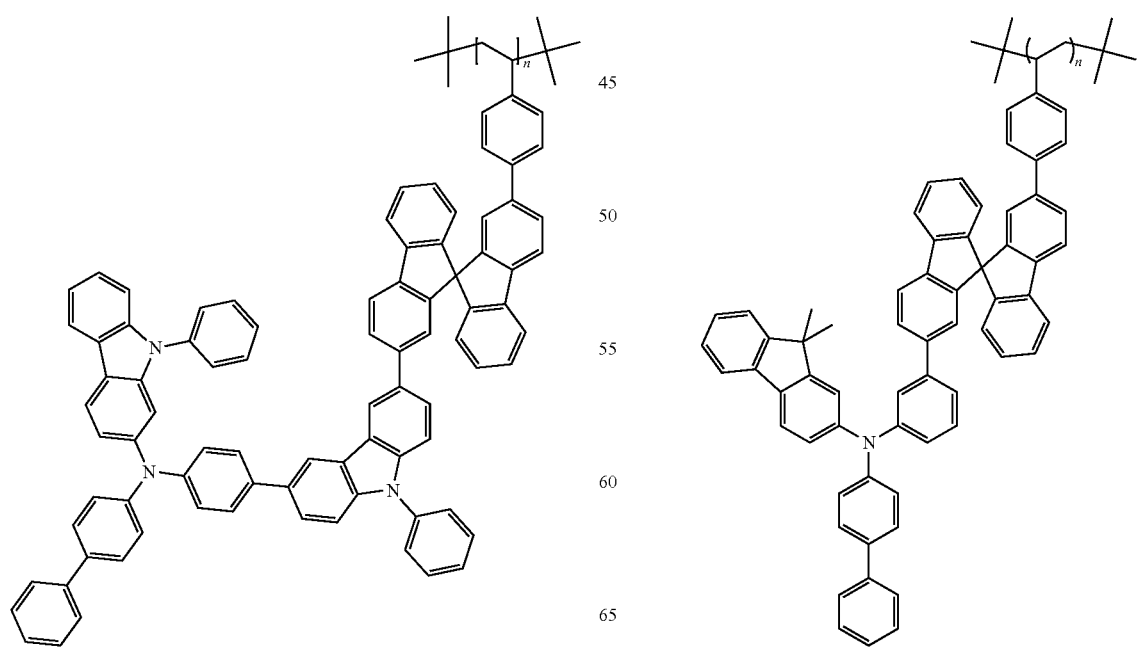

111
-continued
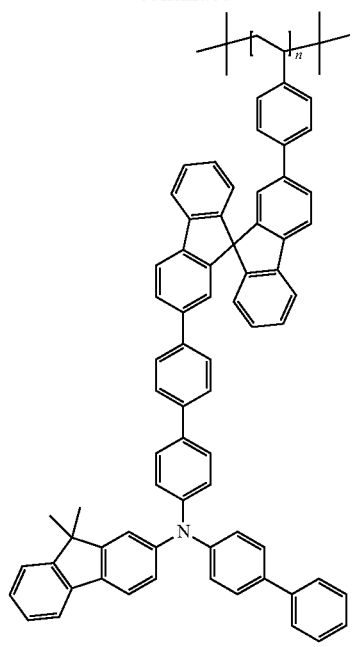
112
-continued
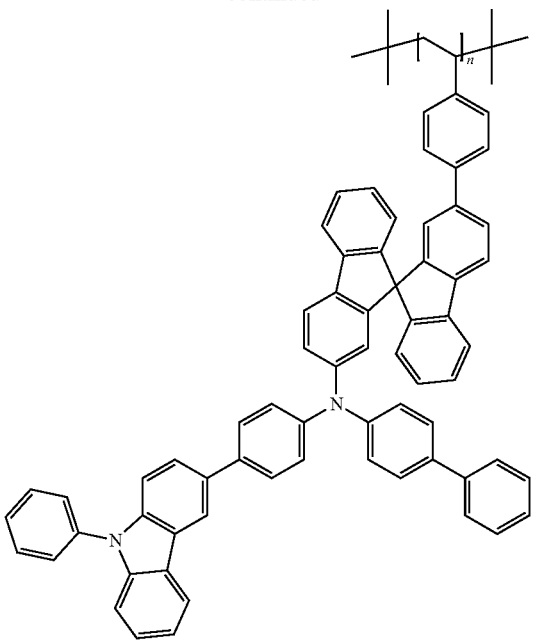
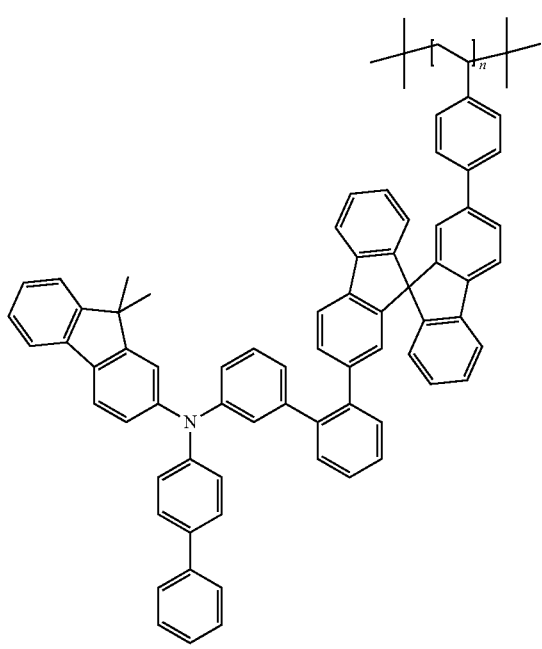
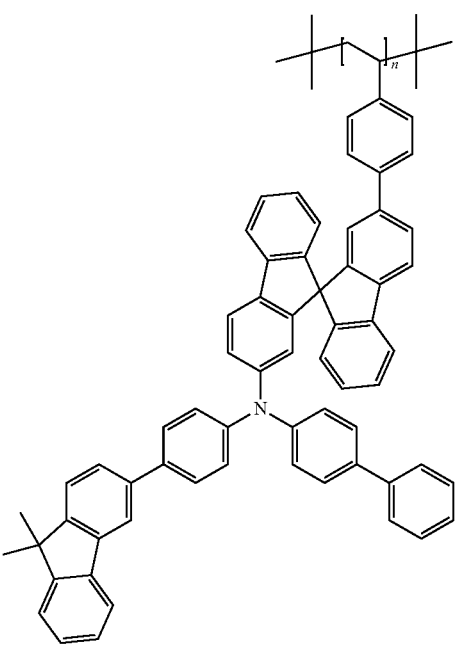

113
-continued
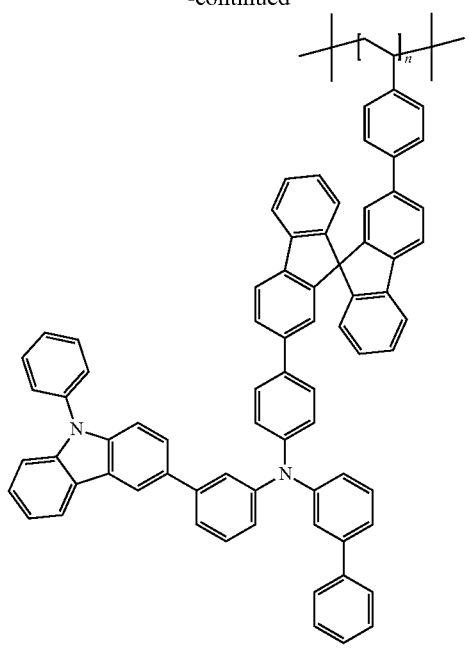
114
-continued
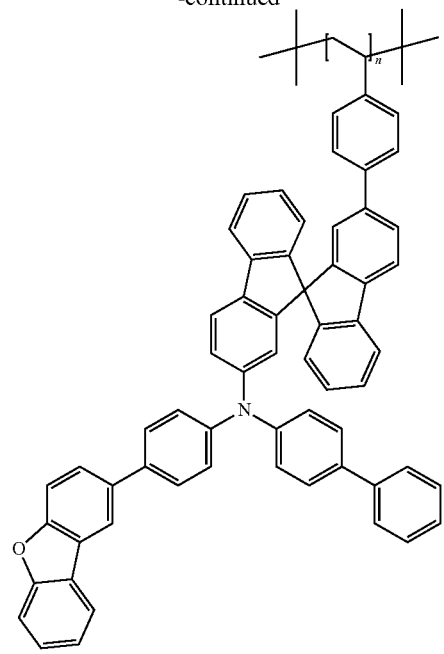
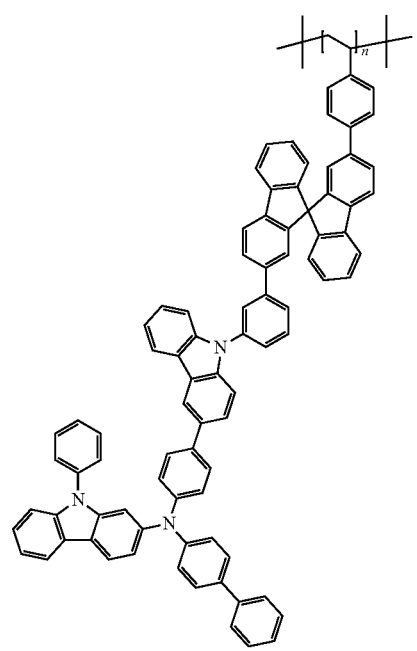

115
-continued
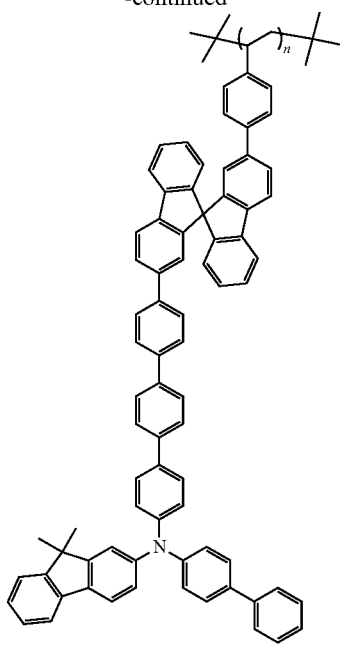
116
-continued
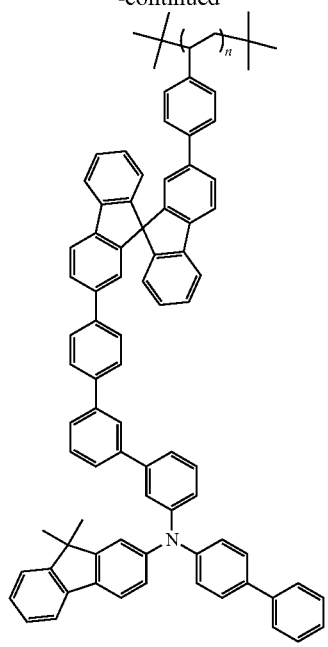
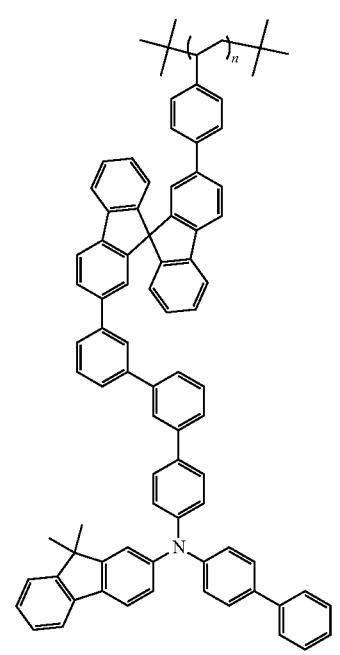
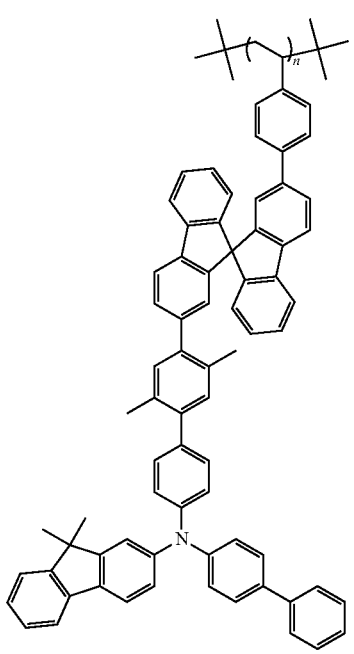

117
-continued
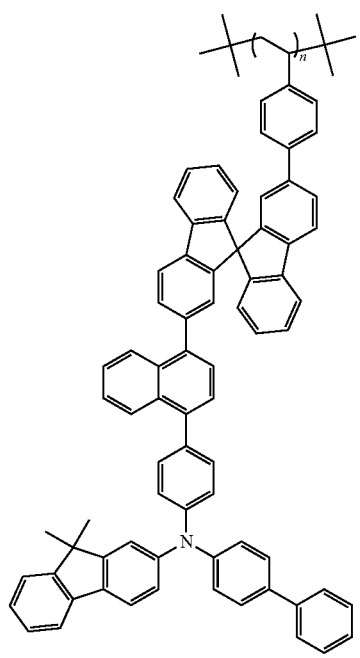
118
-continued
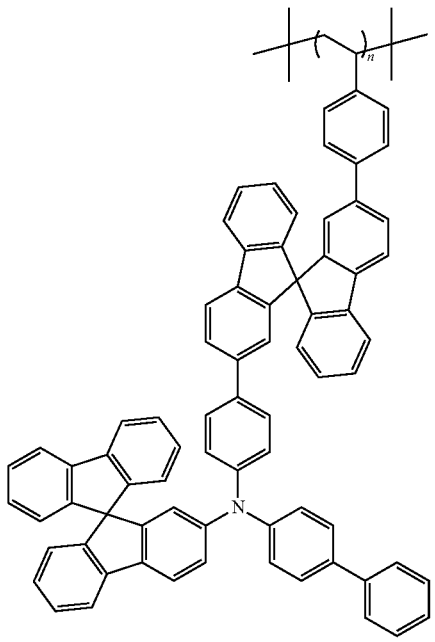
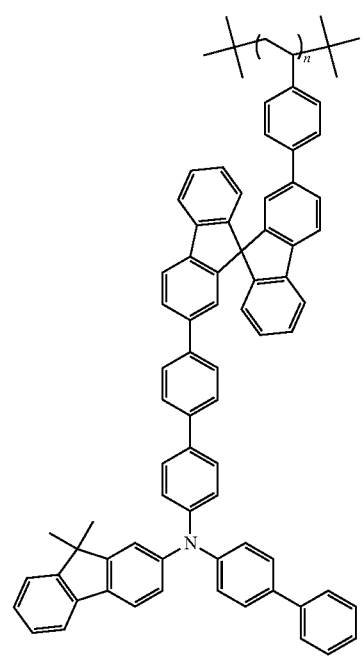
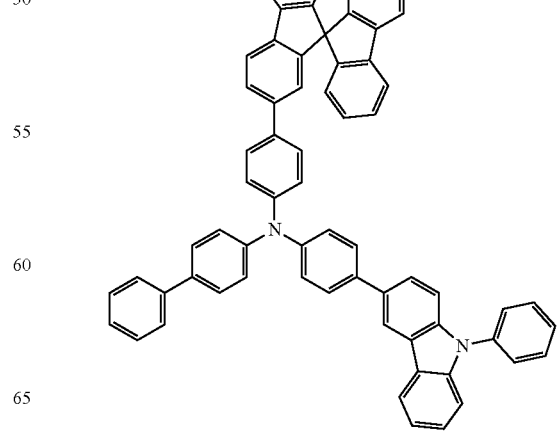

119
-continued
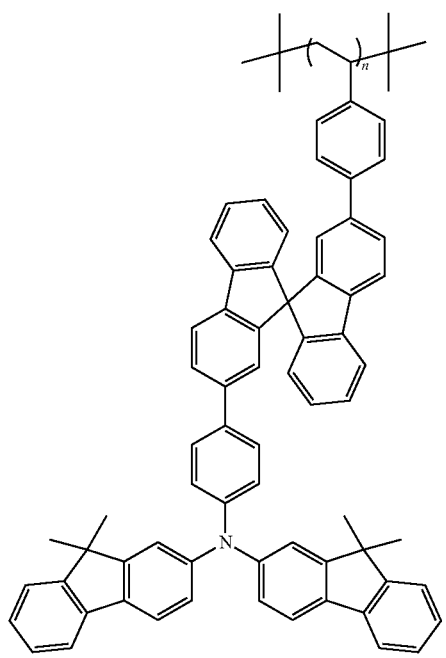
120
-continued
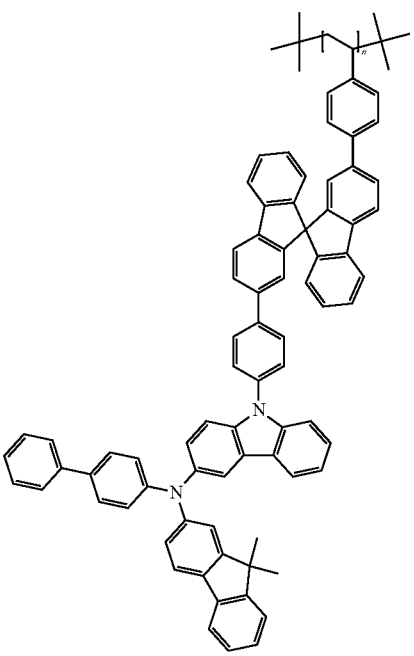
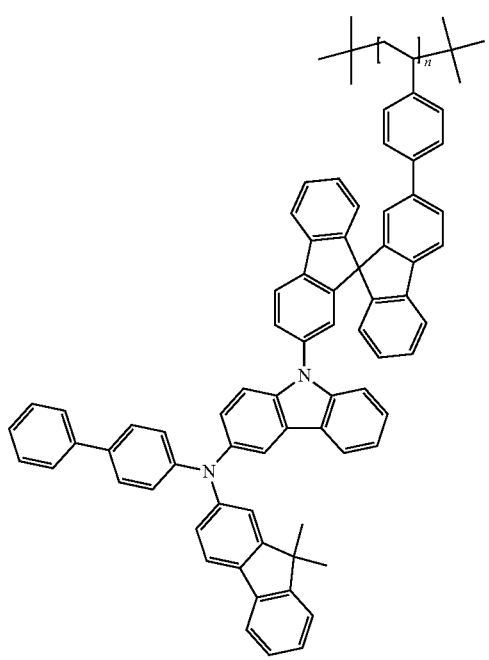
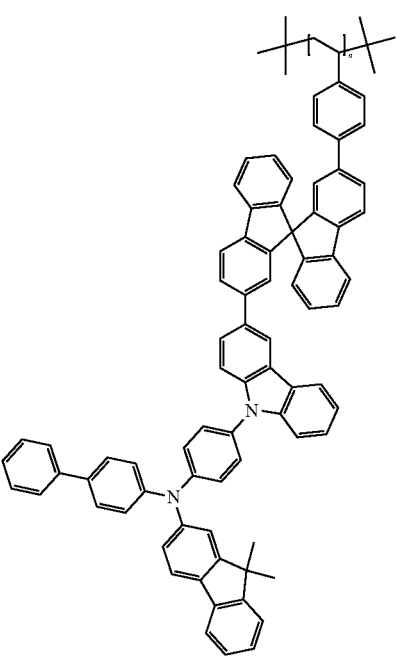

121
-continued

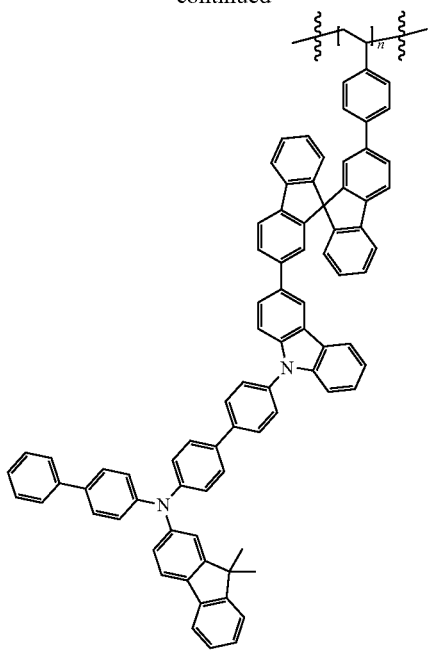

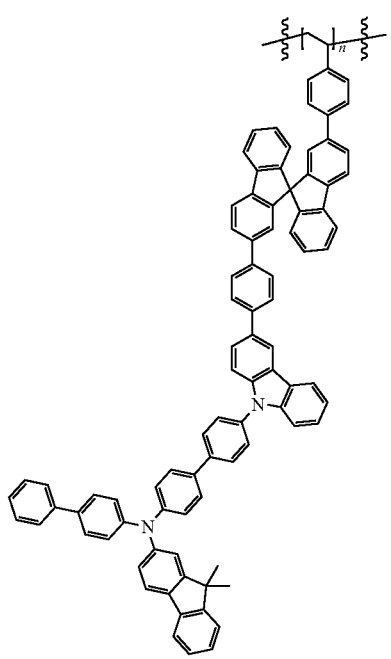

in the structures, n is, as a repetition number of the unit, an integer of 1 to 10,000.

6. The polymer of claim 1, which has a number average molecular weight of 5,000 g/mol to 1,000,000 g/mol.

7. The polymer of claim 1, which has molecular weight distribution of 1 to 10.

122

8. A monomer represented by the following Chemical Formula 2:

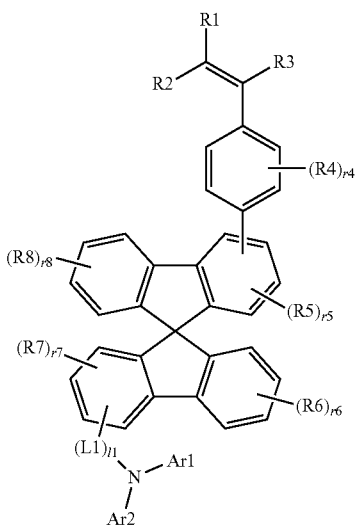

wherein, in Chemical Formula 2,

L1 is a direct bond; a substituted or unsubstituted phenylene group; a substituted or unsubstituted naphthylene group; a substituted or unsubstituted biphenylene group; a substituted or unsubstituted divalent fluorenyl group; or a substituted or unsubstituted divalent carbazolyl group;

l1 is an integer of 1 to 10;

Ar1 and Ar2 are the same as or different from each other, and each independently a substituted or unsubstituted aryl group; or a substituted or unsubstituted heteroaryl group;

R1 to R8 are the same as or different from each other, and each independently hydrogen; deuterium; a halogen group; a hydroxyl group; a cyano group; a substituted or unsubstituted alkyl group; a substituted or unsubstituted cycloalkyl group; a substituted or unsubstituted alkoxy group; a substituted or unsubstituted aryl group; or a substituted or unsubstituted heteroaryl group;

r4, r6 and r8 are each independently an integer of 1 to 4;

r5 and r7 are each independently an integer of 1 to 3;

when r4 is 2 or greater, the two or more R4s are the same as or different from each other;

when r5 is 2 or greater, the two or more R5s are the same as or different from each other;

when r6 is 2 or greater, the two or more R6s are the same as or different from each other;

when r7 is 2 or greater, the two or more R7s are the same as or different from each other;

when r8 is 2 or greater, the two or more R8s are the same as or different from each other; and when l1 is 2 or greater, the two or more L1s are the same as or different from each other.

9. A coating composition comprising the polymer including the unit represented by Chemical Formula 1 of claim 1.

10. A coating composition comprising the monomer represented by Chemical Formula 2 of claim 8.

11. An organic light emitting device comprising:
a first electrode;
a second electrode provided opposite to the first electrode; and at least one organic material layers provided between the first electrode and the second electrode, wherein the at least one organic material layers includes the polymer including the unit represented by Chemical Formula 1 of claim 1.

12. The organic light emitting device of claim 11, wherein the at least one organic material layer including the polymer including the unit represented by Chemical Formula 1 has solubility of 0.05 wt % or less for cyclohexane, cyclohexanone, or dioxane.

13. The organic light emitting device of claim 11, wherein the at least one organic material layer including the polymer including the unit represented by Chemical Formula 1 is a hole transfer layer, a hole injection layer, or a layer carrying out hole transfer and hole injection at the same time.

14. A method for manufacturing an organic light emitting device, the method comprising:

preparing a first electrode;

forming at least one organic material layers on the first electrode; and forming a second electrode on the at least one organic material layer, wherein the forming of the at least one organic material layers includes forming an organic material layer using a coating composition including the polymer including the unit represented by Chemical Formula 1 of claim 1; and the forming of an organic material layer using the coating composition includes coating the coating composition on the first electrode; and heat treating or light treating the coated coating composition.

15. A method for manufacturing an organic light emitting device, the method comprising:

preparing a first electrode;

forming at least one organic material layer on the first electrode; and forming a second electrode on the at least one organic material layer, wherein the forming of the at least one organic material layer includes forming an organic material layer using a coating composition including the monomer represented by Chemical Formula 2 of claim 8; and the forming of an organic material layer using the coating composition includes coating the coating composition on the first electrode; and heat treating or light treating the coated coating composition.

16. The organic light emitting device of claim 11, wherein the at least one organic material layer including the polymer including the unit represented by Chemical Formula 1 has solubility of 0 wt % or greater for cyclohexane, cyclohexanone, or dioxane.

17. The polymer of claim 1, wherein the unit represented by Chemical Formula 1 is represented by the following Chemical Formula 1-4:

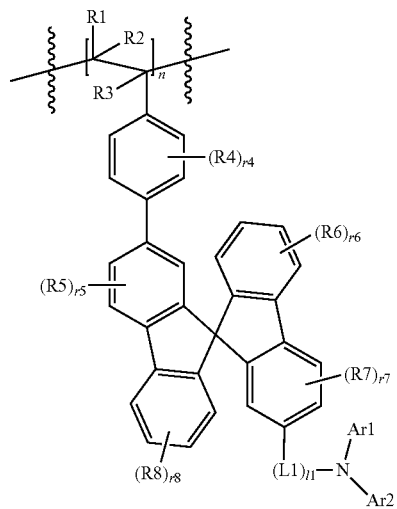

[Chemical Formula 1-4]

in Chemical Formula 1-4,

L1, l1, Ar1, Ar2, n, R1 to R8 and r4 to r8 have the same definitions as in Chemical Formula 1.

18. The monomer of claim 8, which is represented by the following Chemical Formula 2-4:

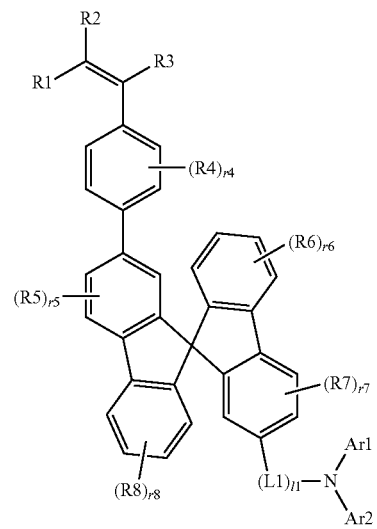

[Chemical Formula 2-4]

in Chemical Formula 2-4,

L1, l1, Ar1, Ar2, n, R1 to R8 and r4 to r8 have the same definitions as in Chemical Formula 2.

19. The polymer of claim 1, wherein L1 is a direct bond, or any one selected from among the following structures:

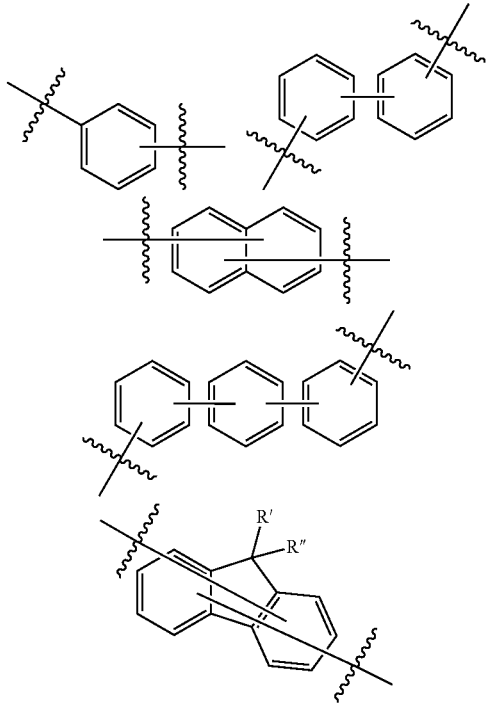
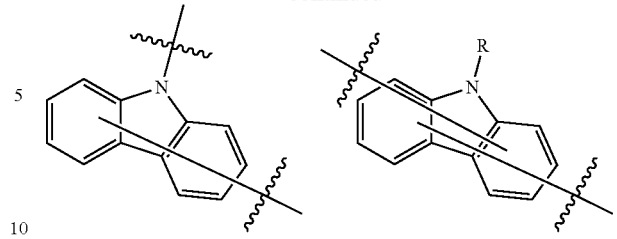

wherein,
R is an aryl group,
R' and R" are the same as or different from each other, and each independently hydrogen; or an alkyl group,

is a site bonding to the spirobifluorene core or N of Chemical Formula 1, and the structures are optionally further substituted with an alkyl group.

* * * * *